US010108776B1

(12) United States Patent
Miller, III et al.

(10) Patent No.: US 10,108,776 B1
(45) Date of Patent: Oct. 23, 2018

(54) TRANSLOCON-ASSOCIATED BIOGENESIS FEATURES AND RELATED METHODS, SYSTEMS AND PRODUCTS

(71) Applicant: CALIFORNIA INSTITUTE OF TECHNOLOGY, Pasadena, CA (US)

(72) Inventors: Thomas F. Miller, III, South Pasadena, CA (US); William M. Clemons, Jr., Pasadena, CA (US); Stephen Marshall, Pasadena, CA (US); Axel Mueller, Pasadena, CA (US); Michiel Niesen, Monrovia, CA (US); Bin Zhang, Houston, TX (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 1100 days.

(21) Appl. No.: 14/301,069

(22) Filed: Jun. 10, 2014

Related U.S. Application Data

(60) Provisional application No. 61/833,250, filed on Jun. 10, 2013, provisional application No. 61/872,103, filed on Aug. 30, 2013.

(51) Int. Cl.
*G06F 19/22* (2011.01)
*A61K 39/00* (2006.01)
*G06F 19/12* (2011.01)

(52) U.S. Cl.
CPC .................... *G06F 19/12* (2013.01)

(58) Field of Classification Search
None
See application file for complete search history.

(56) References Cited

PUBLICATIONS

Schnell et al. Cell, 112, 491-505, 2003.*
Ismail et al. Nat Struct Mol Biol., 2012, 19(10), 1018-1022.*
Restriction Requirement for U.S. Appl. No. 14/301,070, filed Jun. 10, 2014 on behalf of Thomas F. Miller III, dated Jan. 13, 2016. 9 pages.
Non-Final Office Action for U.S. Appl. No. 14/301,070, filed Jun. 10, 2014 on behalf of Thomas F. Miller III, dated Mar. 29, 2016. 12 pages.
Final Office Action for U.S. Appl. No. 14/301,070, filed Jun. 10, 2014 on behalf of Thomas F. Miller III, dated Aug. 19, 2016. 9 pages.
Final Office Action for U.S. Appl. No. 14/301,070, filed Jun. 10, 2014 on behalf of Thomas F. Miller III, dated Aug. 3, 2017. 9 pages.
Abou Elela, S. et al., "Role of the 5.8S rRNA in Ribosome Translocation.", *Nucleic Acids Research*, vol. 25, No. 9, pp. 1788-1794, (1997).
Anderson, H. et al., "Different Positively Charged Amino Acids Have Similar Effects on the Topology of a Polytopic Transmembrane Protein in *Escherichia coli*.", Journal of Biological Chemistry, vol. 267, No. 3, pp. 1491-1495, (1992), 6 pages.

Becker, T. et al., "Structure of Monomeric Yeast and Mammalian Sec61 Complexes Interacting with the Translating Ribosome.", Science, vol. 326, pp. 1369-1373, (2009).
Beckmann, R. et al., "Architecture of the Protein-Conducting Channel Associated with the Translating 80S Ribosome.", Cell, vol. 107, pp. 361-372, (2001).
Beltzer, J.P., et al., "Charged Residues Are Major Determinants of the Transmembrane Orientation of a Signal-Anchor Sequence.", Journal of Biological Chemistry, vol. 266, No. 2, pp. 973-978, (1991).
Berendsen, H.J.C. et al., "Molecular Dynamics with Coupling to an External Bath.", Journal of Chemical Physics, vol. 81, No. 8, pp. 3684-3690, (1984), 8 pages.
Bieker, K.L. et al., "PrlA (SecY) and PrlG (SecE) Interact Directly and Function Sequentially during Protein Translocation in *E. coli*.", Cell, vol. 61, pp. 833-842, (1990).
Bilgin, N. et al., "Kinetic Properties of *Escherichia coli* Ribosomes with Altered Forms of S12.", J. Mol. Biol., vol. 224, pp. 1011-1027, (1992).
Boehlke, K.W. et al., "Cellular Content of Ribonucleic Acid and Protein in *Saccharomyces cerevisiae* as a Function of Exponential Growth Rate: Calculation of the Apparent Peptide Chain Elongation Rate.", Journal of Bacteriology, vol. 121, No. 2, pp. 429-433, (1975).
Bogdanov, M. et al., "To Flip or Not to Flip: Lipid-Protein Charge Interactions are a Determinant of Final Membrane Protein Topology.", J. Cell Biol., vol. 182, No. 5, pp. 925-935, (2008).
Bogsch, E.G. et al., "An Essential Component of a Novel Bacteria Protein Export System with Homologues in Plastids and Mitochondria.", Journal of Biological Chemistry, vol. 273, No. 29, pp. 18003-18006, (1998), 5 pages.
Bonardi, F. et al., "Probing the SecYEG Translocation Pore Size with Preproteins Conjugated with Sizable Rigid Spherical Molecules.", PNAS, vol. 108, No. 19, pp. 7775-7780, (2011), 7 pages.

(Continued)

*Primary Examiner* — Michael L Borin
(74) *Attorney, Agent, or Firm* — Steinfl + Bruno LLP

(57) ABSTRACT

Methods and systems are described to provide computerized trajectory-based methods to represent translocon-associated protein trajectories, provide proteins or protein sequences with desired translocon-associated biogenesis features, screening proteins or protein sequences to provide proteins or protein sequences with desired translocon-associated biogenesis features, screening translocon-associated biogenesis feature determinants to provide proteins or protein sequences with desired translocon-associated biogenesis features, identifying translocon-associated biogenesis feature determinants of a given protein sequence, computer-based protein sequence identification methods, computer-based methods for identifying correlations in a set of protein sequences, computer-based methods for identifying correlations between experimental data and computer-generated data in a protein sequence, and computer-based methods for determining which modifications of a protein sequence do not substantially affect a translocon-associated biogenesis feature of the protein sequence.

17 Claims, 60 Drawing Sheets
Specification includes a Sequence Listing.

(56) References Cited

PUBLICATIONS

Bondar, A.N. et al., "Dynamics of SecY Translocons with Translocation-Defective Mutations.", Structure, 18, pp. 847-857, (2010).
Brodsky, J.L. et al., "BiP and Sec63p are Required for Both Co- and Posttranslational Protein Translocation into the Yeast Endoplasmic Reticulum.", Proc. Natl. Acad. Sci., vol. 92, pp. 9643-9646, (1995).
Buchete, N-V. et al., "Coarse Master Equations for Peptide Folding Dynamics.", J. Phys. Chem. B, vol. 112, No. 19, pp. 6057-6068, (2008), 13 pages.
Chandler, D., "Roles of Classical Dynamics and Quantum Dynamics on Activated Processes Occurring in Liquids.", Journal of Statistical Physics, vol. 42, Nos. 1/2, pp. 49-67, (1986).
Chandler, D., "Interfaces and the Driving Force of Hydrophobic Assembly.", Nature Publishing Group, vol. 437, pp. 640-647, (2005), 9 pages.
Chauwin, J-F. et al., "Strong Precursor-Pore Interactions Constrain Models for Mitochondrial Protein Import.", Biophysical Journal, vol. 74, pp. 1732-1743, (1998).
Cheng, Z. et al., "Slow Translocon Gating Causes Cytosolic Exposure of Transmembrane and Lumenal Domains During Membrane Protein Integration.", Nat. Structural & Molecular Biology, vol. 13, No. 10, pp. 930-936, (2006).
Chuang J. et al., "Anomalous Dynamics of Translocation.", Physical Review E, vol. 65, pp. 011802-1-011802-8, (2001), 8 pages.
Crowley, K.S. et al., "Secretory Proteins Move Through the Endoplasmic Reticulum Membrane via an Aqueous, Gated Pore.", Cell, vol. 78, pp. 461-471, (1994).
Crowley, K.S. et al., "The Signal Sequence Moves Through a Ribosomal Tunnel into a Noncytoplasmic Aqueous Environment at the ER Membrane Early in Translocation.", Cell, vol. 73, pp. 1101-1115, (1993).
Denzer, A. et al., "Transmembrane Orientation of Signal-Anchor Proteins is Affected by the Folding State but not the Size of the N-Terminal Domain.", The EMBO Journal, vol. 14, No. 24, pp. 6311-6317, (1995).
Devaraneni, P.K. et al., "Stepwise Insertion and Inversion of a Type II Signal Anchor Sequence in the Ribosome-Sec61 Translocon Complex.", Cell, 146, pp. 134-147, (2011).
Dill, K.A. et al., "Principles of Protein Folding—A Perspective from Simple Exact Models.", Protein Science, 4, pp. 561-602, (1995).
Do, H. et al., "The Cotranslational Integration of Membrane Proteins into the Phospholipid Bilayer is a Multistep Process.", Cell, vol. 85, pp. 369-378, (1996).
Dowhan, W. et al., "Lipid-Dependent Membrane Protein Topogenesis.", Annu. Rev. Biochem., vol. 78, pp. 515-540, (2009), 30 pages.
Drew, D. et al., "Green Fluorescent Protein as an Indicator to Monitor Protein Overexpression in *Escherichia coli*.", FEBS Letters 507, pp. 220-224, (2001).
Duong, F. et al., "Sec-Dependent Membrane Protein Biogenesis: SecYEG, Preprotein Hydrophobicity and Translocation Kinetics Control the Stop-Transfer Function.", The EMBO Journal, vol. 17, No. 3, pp. 696-705, (1998).
Egea, P.F. et al., "Lateral Opening of a Translocon Upon Entry of Protein Suggests the Mechanism of Insertion into Membranes.", PNAS, vol. 107, No. 40, pp. 17182-17187, (2010).
Elston, T.C., "Models of Post-Translational Protein Translocation.", Biophysical Journal, vol. 79, pp. 2235-2251, (2000).
Erlandson, K.J. et al., "A Role for the Two-Helix Finger of the SecA ATPase in Protein Translocation.", vol. 455, pp. 984-988, (2008).
Frauenfeld, M. et al., "Cryo-EM Structure of the Ribosome-SecYE Complex in the Membrane Environment.", Nature Structural & Molecular Biology, vol. 18, No. 5, pp. 614-621, (2011), 9 pages.
Fujita, H. et al., "Positive Charges of Translocating Polypeptide Chain Retrieve an Upstream Marginal Hydrophobic Segment from the Endoplasmic Reticulum Lumen to the Translocon.", Mol. Biol. Cell, vol. 21, pp. 2045-2056, (2010).
Garrison, J.L. et al., "A Substrate-Specific Inhibitor of Protein Translocation into the Endoplasmic Reticulum.", Nature, vol. 436, pp. 285-289, (2005).
Go, N. et al., "Respective Roles of Short- and Long-Range Interactions in Protein Folding.", Proc. Natl. Acad. Sci., vol. 75, No. 2, pp. 559-563, (1978).
Gobas, F.A. et al., "A Novel Method for Measuring Membrane-Water Partition Coefficients of Hydrophobic Organic Chemicals: Comparison with 1-Octanol-Water Partitioning.", J. Pharm. Sci., vol. 77, No. 3, pp. 265-272, (1988).
Goder, V. et al., "Molecular Mechanism of Signal Sequence Orientation in the Endoplasmic Reticulum.", The EMBO Journal, vol. 22, No. 14, pp. 3645-3653, (2003).
Goder, V. et al., "Topogenesis of Membrane Proteins: Determinants and Dynamics.", FEBS Lett. 504, pp. 87-93, (2001).
Goder, V. et al., "Sec61p Contributes to Signal Sequence Orientation According to the Positive-Inside Rule.", Mol. Biol. Cell, vol. 15, pp. 1470-1478, (2004).
Goldschmidt, L. et al., "Toward Rational Protein Crystallization: A Web Server for the Design of Crystallizable Protein Variants.", Protein Science, vol. 16, pp. 1569-1576, (2007).
Gumbart, J. et al., "Molecular Dynamics Studies of the Archaeal Translocon.", Biophysical Journal, vol. 90, pp. 2356-2367, (2006).
Gumbart, J. et al., Structural Determinants of Lateral Gate Opening in the Protein Translocon. Biochemistry, vol. 46, No. 39, pp. 11147-11157, (2007).
Gumbart, J. et al. "Free-Energy Cost for Translocon-Assisted Insertion of Membrane Proteins.", PNAS, vol. 108, No. 9, pp. 3596-3601, (2011).
Haider, S. et al., Simulations of a Protein Translocation Pore: SecY, Biochemistry, vol. 45, No. 43, pp. 13018-13024, (2006).
Hanke, A. et al., Stretching Single Polypeptides: The Effect of Rotational Constraints in the Backbone. EPL, 92,53001-p1-53001-p6, (2010), 6 pages.
Harley, C.A. et al., "Transmembrane Protein Insertion Orientation in Yeast Depends on the Charge Difference Across Transmembrane Segments, Their Total Hydrophobicity, and its Distribution.", J. Biol. Chem., vol. 273, No. 38, pp. 24963-24971, (1998), 10 pages.
Hedin, L.E. et al., "Membrane Insertion of Marginally Hydrophobic Transmembrane Helices Depends on Sequence Context.", J. Mol. Biol., 396, pp. 221-229, (2010).
Heinrich, S.U. et al., "The Sec61p Complex Mediates the Integration of a Membrane Protein by Allowing Lipid Partitioning of the Transmembrane Domain.", Cell, vol. 102, pp. 233-244, (2000).
Heritage, D. et al., "Translocon Pores in the Endoplasmic Reticulum are Permeable to a Neutral, Polar Molecule.", J. Biol. Chem., vol. 276, No. 25, pp. 22655-22662, (2001), 9 pages.
Hessa, T. et al., "Membrane Insertion of a Potassium-Channel Voltage Sensor.", Science, vol. 307, p. 1427, (2005), 2 pages.
Hessa, T. et al., "Recognition of Transmembrane Helices by the Endoplasmic Reticulum Translocon.", Nature, vol. 433, pp. 377-381, (2005).
Hessa, T. et al., "Molecular Code for Transmembrane-Helix Recognition by the Sec61 Translocon.", Nature, vol. 450, pp. 1026-1030, (2007), 7 pages.
Hessa, T., et al., "Stop-Transfer Efficiency of Marginally Hydrophobic Segments Depends on the Length of the Carboxyterminal Tail.", The EMBO Journal, vol. 4, No. 2, pp. 178-183, (2003).
Higy, M. et al., "Probing the Environment of Signal-Anchor Sequences During Topogenesis in the Endoplasmic Reticulum.", Biochemistry, vol. 44, No. 6, pp. 2039-2047, (2005), 10 pages.
Hikita, C. et al., "Effects of Total Hydrophobicity and Length of the Hydrophobic Domain of a Signal Peptide on in vitro Translocation Efficiency.", J. Biol. Chem., vol. 267, No. 7, pp. 4882-4888, (1992).
Hizlan, D. et al., "Structure of the SecY Complex Unlocked by a Preprotein Mimic.", Cell Reports 1, pp. 21-28, (2012).
Hoover, J. et al., "DNAWorks: an Automated Method for Designing Oligonucleotides for PCR-Based Gene Synthesis.", Nucleic Acids Research, vol. 30, No. 10, e43, (2002), 7 pages.
Hummer, G., "From Transition Paths to Transition States and Rate Coefficients.", J. Chem. Physics, vol. 120, No. 2, pp. 516-523, (2004).
Huopaniemi, I. et al., "Langevin Dynamics Simulations of Polymer Translocation Through Nanopores.", J. Chem. Phys. 125, 124901, (2006), 8 pages.

(56) References Cited

OTHER PUBLICATIONS

Jungnickel, B. et al., "A Posttargeting Signal Sequence Recognition Event in the Endoplasmic Reticulum Membrane.", Cell, vol. 82, pp. 261-270, (1995).
Junne, T. et al., "The Hydrophobic Core of the Sec61 Translocon Defines the Hydrophobicity Threshold for Membrane Integration.", Mol. Biol. Cell, vol. 21, pp. 1662-1670, (2010).
Junne, T. et al., "Mutations in the Sec61p Channel Affecting Signal Sequence Recognition and Membrane Protein Topology.", J. Biol. Chem., vol. 282, No. 45, pp. 33201-33209, (2007), 10 pages.
Kamerlin, S.CL. et al., "Coarse-Grained (Multiscale) Simulations in Studies of Biophysical and Chemical Systems.", Annu. Rev. Phys. Chem., 62, pp. 41-64, (2011), 27 pages.
Kida, Y. et al., "Function of Positive Charges Following Signal-Anchor Sequences During Translocation of the N-Terminal Domain.", J. Biol. Chem., vol. 281, No. 2, pp. 1152-1158, (2006), 8 pages.
Kim, S.J. et al., "Signal Sequences Control Gating of the Protein Translocation Channel in a Substrate-Specific Manner.", Developmental Cell, vol. 2, pp. 207-217, (2002).
Klauda, J.B. et al., "Update of the CHARMM All-Atom Additive Force Field for Lipids: Validation on Six Lipid Types.", J. Phys. Chem. B, vol. 114, No. 23, pp. 7830-7843, (2010).
Klock, H.E. et al., The Polymerase Incomplete Primer Extension (PIPE) Method Applied to High-Throughput Cloning and Site-Directed Mutagenesis. Methods Mol. Biol., vol. 498, pp. 91-103, (2009).
Krautler, V. et al., "A Fast Shake Algorithm to Solve Distance Constraint Equations for Small Molecules in Molecular Dynamics Simulations.", J. Comput. Chem., vol. 22, No. 5, pp. 501-508, (2001).
Kremer, K. et al., "Dynamics of Entangled Linear Polymer Melts: A Molecular-Dynamics Simulation.", J Chem Phys., vol. 92, No. 8, pp. 5057-5086, (1990).
Krogh, B. et al., "Predicting Transmembrane Protein Topology with a Hidden Markov Model: Application to Complete Genomes.", J. Mol. Biol., 305, pp. 567-580, (2001).
Kyte, J. et al., "A Simple Method for Displaying the Hydropathic Character of a Protein.", J. Mol. Biol., 157, pp. 105-132, (1982).
Lerch-Bader, M. et al., "Contribution of Positively Charged Flanking Residues to the Insertion of Transmembrane Helices into the Endoplasmic Reticulum.", PNAS, vol. 105, No. 11, pp. 4127-4132, (2008).
Lewinson, O. et al., "The Funnel Approach to the Precrystallization Production of Membrane Proteins.", J. Mol. Biol., 377, pp. 62-73, (2008).
Li, M.S. et al., "Folding in Two-Dimensional Off-Lattice Models of Proteins.", Phys. Rev. E, vol. 59, No. 1, pp. 970-976, (1999).
Liebermeister, W. et al., "Ratcheting in Post-Translational Protein Translocation: A Mathematical Model.", J. Mol. Biol., 305, pp. 643-656, (2001).
Lindahl, E. et al., "Membrane Proteins: Molecular Dynamics Simulations.", Current Opinion in Structural Biology, 18, pp. 425-431, (2008).
Luo, K. et al., "Influence of Polymer-Pore Interactions on Translocation.", Phys. Rev. Lett., 99, 148102, (2007), 4 pages.
Luo, K. et al., "Sequence Dependence of DNA Translocation Through a Nanopore.", Phys. Rev. Lett., 100, 058101, (2008), 4 pages.
Mackerell, A.D. et al., "All-Atom Empirical Potential for Molecular Modeling and Dynamics Studies of Proteins.", J. Phys. Chem. B, vol. 102, No. 18, pp. 3586-3616, (1998).
Maifeld, S.V. et al., "Secretory Protein Profiling Reveals TNF-α Inactivation by Selective and Promiscuous Sec61 Modulators.", Chemistry & Biology 18, pp. 1082-1088, (2011).
Matlack, K.E.et al., "BiP Acts as a Molecular Ratchet During Posttranslational Transport of Prepro-α Factor across the ER Membrane.", Cell, vol. 97, pp. 553-564, (1999).

Meindl-Beinker, N.M. et al., "Asn- and Asp-mediated Interactions Between Transmembrane Helices During Translocon-Mediated Membrane Protein Assembly.", The EMBO Reports, vol. 7, No. 11, pp. 1111-1116, (2006).
Moon, C.P. et al., "Side-Chain Hydrophobicity Scale Derived from Transmembrane Protein Folding into Lipid Bilayers.", PNAS, vol. 108, No. 25, pp. 10174-10177, (2011).
Muthukumar, M., "Polymer Translocation Through a Hole.", J. Chem. Physiol., vol. 111, No. 22, pp. 10371-10374, (1999), 5 pages.
Nilsson, I. et al., "Fine-Tuning the Topology of a Polytopic Membrane Protein: Role of Positively and Negatively Charged Amino Acids.", Cell, vol. 62, pp. 1135-1141, (1990).
Ojemalm, K. et al., "Apolar Surface Area Determines the Efficiency of Translocon-Mediated Membrane—Protein Integration into the Endoplasmic Reticulum.", PNAS, vol. 108, No. 31, E359-E364, (2011), 7 pages.
Panja, D. et al., "Anomalous Dynamics of Unbiased Polymer Translocation through a Narrow Pore.", J. Phys. Condens. Matter 19, 432202-432202, (2007), 8 pages.
Park, E. et al., "Preserving the Membrane Barrier for Small Molecules During Bacterial Protein Translocation.", Nature, vol. 473, pp. 239-242, (2011), 6 pages.
Parks, G.D. et al., "Topology of Eukaryotic Type II Membrane Proteins: Importance of N-Terminal Positively Charged Residues Flanking the Hydrophobic Domain.", Cell, vol. 64, pp. 777-787, (1991).
Plath, K. et al., "Signal Sequence Recognition in Posttranslational Protein Transport Across the Yeast ER Membrane.", Cell, vol. 94, pp. 795-807, (1998).
Ramadurai, S. et al., "Lateral Diffusion of Membrane Proteins.", J. Am. Chem. Soc., vol. 131, No. 35, pp. 12650-12656, (2009).
Ramasamy S. et al., "The Glove-like Structure of the Conserved Membrane Protein TatC Provides Insight into Signal Sequence Recognition in Twin-Arginine Translocation.", Structure 21, pp. 777-788, (2013).
Rapoport, T.A., "Protein Translocation Across the Eukaryotic Endoplasmic Reticulum and Bacterial Plasma Membranes.", Nature, vol. 450, pp. 663-669, (2007).
Rapoport, T.A. et al., "Membrane-Protein Integration and the Role of the Translocation Channel.", Trends Cell Biol., vol. 14, No. 10, pp. 568-575, (2004).
Rollauer, S.E. et al., "Structure of the TatC Core of the Twin-Arginine Protein Transport System.", Nature, vol. 492, pp. 210-214, (2012), 6 pages.
Rutkowski, D.T. et al., "Substrate-Specific Regulation of the Ribosome—Translocon Junction by N-Terminal Signal Sequences.", PNAS, vol. 98, No. 14, pp. 7823-7828, (2001).
Rychkova, A. et al., "On the Energetics of Translocon-Assisted Insertion of Charged Transmembrane Helices into Membranes.", PNAS, vol. 107, No. 41, pp. 17598-17603, (2010).
Saaf, A. et al., "Stop-Transfer Function of Pseudo-Random Amino Acid Segments During Translocation Across Prokaryotic and Eukaryotic Membranes.", Eur. J. Biochem. 251, pp. 821-829, (1998).
Sanders, S.L. et al., "Sec61p and BiP Directly Facilitate Polypeptide Translocation into the ER.", Cell, vol. 69, pp. 353-365, (1992).
Schlegel, S. et al., "Revolutionizing Membrane Protein Overexpression in Bacteria.", Microbial Biotechnology, 3(4), pp. 403-411, (2010).
Scott, D.J. et al., "Stabilizing Membrane Proteins Through Protein Engineering.", Current Opinion in Chemical Biology, 17, 427-435, (2013).
Seiser, R.M. et al., "The Fate of Membrane-Bound Ribosomes Following the Termination of Protein Synthesis.", J. Biol. Chem., vol. 275, No. 43, pp. 33820-33827, (2000).
Seppala, S. et al., "Control of Membrane Protein Topology by a Single C-Terminal Residue.", Science, vol. 328, pp. 1698-1700, (2010), 4 pages.
Shan, Y. et al., "Gaussian Split Ewald: A Fast Ewald Mesh Method for Molecular Simulation.", J. Chem. Phys., 122, pp. 054101-1-05401-13, (2005), 14 pages.
Shaw, A.S. et al., "Evidence for the Loop Model of Signal-Sequence Insertion into the Endoplasmic Reticulum.", Proc. Natl. Acad. Sci. USA, vol. 85, pp. 7592-7596, (1988).

(56) References Cited

OTHER PUBLICATIONS

Shaw, D.E. et al., "Atomic-Level Characterization of the Structural Dynamics of Proteins.", Science, vol. 330, pp. 341-346, (2010), 7 pages.

Simon, S.M. et al., What drives the translocation of proteins? Proc. Natl. Acad. Sci. USA, vol. 89, pp. 3770-3774, (1992).

Smith, M.A. et al., "Modeling the Effects of prl Mutations on the *Escherichia coli* SecY Complex.", J. Bacteriol., vol. 187, pp. 6454-6465, (2005), 13 pages.

Sonoda, Y. et al., "Tricks of the Trade used to Accelerate High-Resolution Structure Determination of Membrane Proteins. ", FEBS letters 584, pp. 2539-2547, (2010).

Sriraman, S. et al., "Coarse Master Equation from Bayesian Analysis of Replica Molecular Dynamics Simulations.", J. Phys. Chem. B, vol. 109, No. 14, pp. 6479-6484, (2005).

Staple, S. H. et al., Model for Stretching and Unfolding the Giant Multidomain Muscle Protein Using Single-Molecule Force Spectroscopy. Phys. Rev. Lett. 101, pp. 248301-1-248301-4, (2008), 4 pages.

Sung, W. et al., "Polymer Translocation through a Pore in a Membrane.", Phys. Rev. Letters, vol. 77, No. 4, pp. 783-786, (1996).

Tian, P., "Size, Motion, and Function of the SecY Translocon Revealed by Molecular Dynamics Simulations with Virtual Probes.", Biophys. J., vol. 90(8), pp. 2718-2730, (2006).

Tsukazaki, T. et al., "Conformational Transition of Sec Machinery Inferred from Bacterial SecYE Structures.", Nature, vol. 455, pp. 988-991, (2008), 5 pages.

Tuckerman, M. et al., "Reversible Multiple Time Scale Molecular Dynamics.", J. Chem. Phys., vol. 97, No. 3, pp. 1990-2001, (1992), 13 pages.

Tyedmers, J. et al., "Polypeptide-Binding Proteins Mediate Completion of Co-Translational Protein Translocation into the Mammalian Endoplasmic Reticulum.", The EMBO Reports, vol. 4, No. 5, pp. 505-510, (2003).

Vaes, W.H.J. et al., "Understanding and Estimating Membrane/Water Partition Coefficients: Approaches to Derive Quantitative Structure Property Relationships.", Chem. Res. Toxicol., vol. 11, No. 8, pp. 847-854, (1998).

Van Den Berg, B. et al., "X-ray Structure of a Protein-Conducting Channel.", Nature, vol. 427, pp. 36-44, (2004).

Von Heijne, G., "The Distribution of Positively Charged Residues in Bacterial Inner Membrane Proteins Correlates with the Trans-Membrane Topology.", The EMBO Journal, vol. 5, No. 11, pp. 3021-3027, (1986).

Von Heijne, G., "Control of Topology and Mode of Assembly of a Polytopic Membrane Protein by Positively Charged Residues.", Nature, vol. 341, pp. 456-458, (1989).

Wagner, S. et al., "Rationalizing Membrane Protein Overexpression.", Trends in Biotechnology, vol. 24, No. 8, pp. 364-371, (2006).

Wahlberg, J.M. et al., "Multiple Determinants Direct the Orientation of Signal-Anchor Proteins: The Topogenic Role of the Hydrophobic Signal Domain.", J. Cell Biol., vol. 137, No. 3, pp. 555-562, (1997).

Weeks, J.D. et al., "Role of Repulsive Forces in Determining the Equilibrium Structure of Simple Liquids.", J. Chem. Phys., vol. 54, No. 12, pp. 5237-5247, (1971), 12 pages.

Wei, D. et al., "Unforced Translocation of a Polymer Chain through a Nanopore: The Solvent Effect.", J. Chem. Phys., vol. 126, pp. 204901-1-204901-8, (2007), 8 pages.

Wimley, W.C. et al., "Solvation Energies of Amino Acid Side Chains and Backbone in a Family of Host-Guest Pentapeptides.", Biochemistry, vol. 35, No. 16, pp. 5109-5124, (1996).

Yang, Z.R. et al., "RONN: The Bio-Basis Function Neural Network Technique Applied to the Detection of Natively Disordered Regions in Proteins.", Bioinformatics, vol. 21, No. 16, pp. 3369-3376, (2005).

Zhang B. et al., "Hydrophobically Stabilized Open State for the Lateral Gate of the Sec Translocon.", PNAS, vol. 107, No. 12, pp. 5399-5404, (2010).

Zhang B. et al., "Long-Timescale Dynamics and Regulation of Sec-Facilitated Protein Translocation.", Cell Reports 2, pp. 927-937, (2012).

Zhang, B. et al., "Direct Simulation of Early-Stage Sec-Facilitated Protein Translocation.", J. Am. Chem. Soc., 134, pp. 13700-13707, (2012).

Zimmer, J. et al., "Conformational Flexibility and Peptide Interaction of the Translocation ATPase SecA.", J. Mol. Biol., 394, pp. 606-612, (2009).

Zimmer, J. et al., "Structure of a Complex of the ATPase SecA and the Protein-Translocation Channel.", Nature, vol. 455, 936-943, (2008), 10 pages.

Notice of Allowance for U.S. Appl. No. 14/301,070, filed Jun. 10, 2014 on behalf of Thomas F. Miller III. dated Apr. 9, 2018. 14 pages.

* cited by examiner

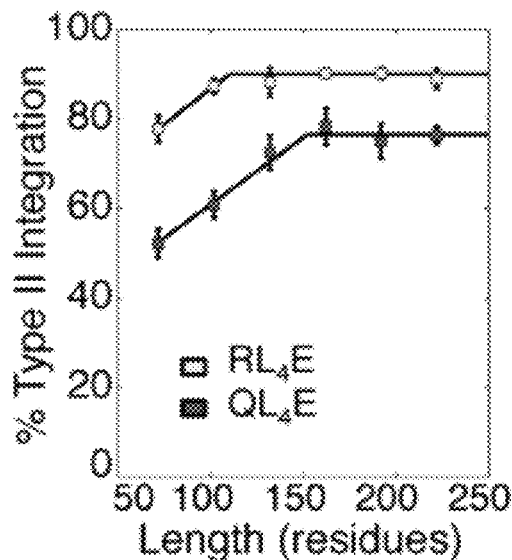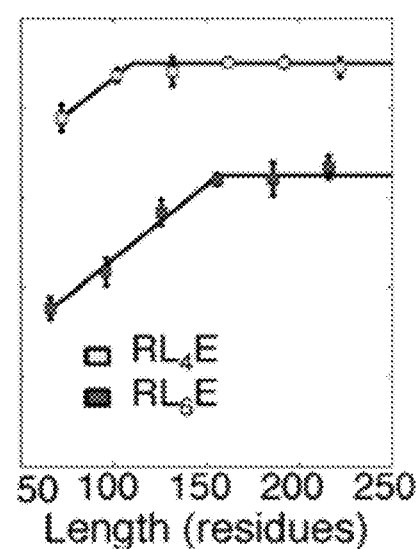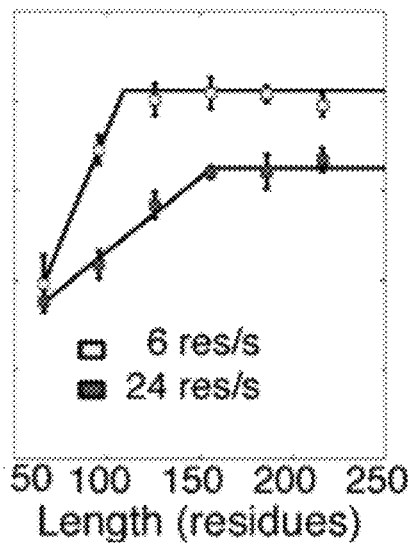

FIG. 4A
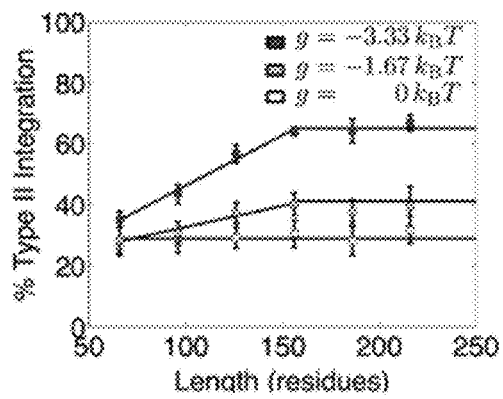
FIG. 4B
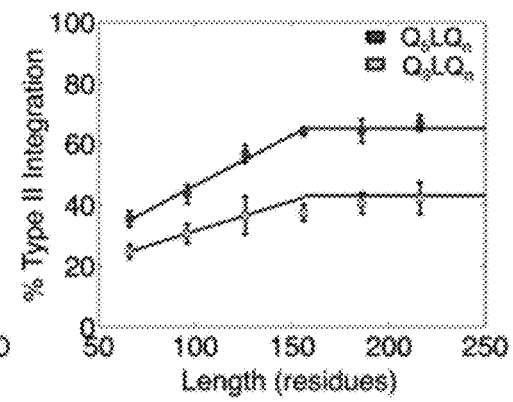
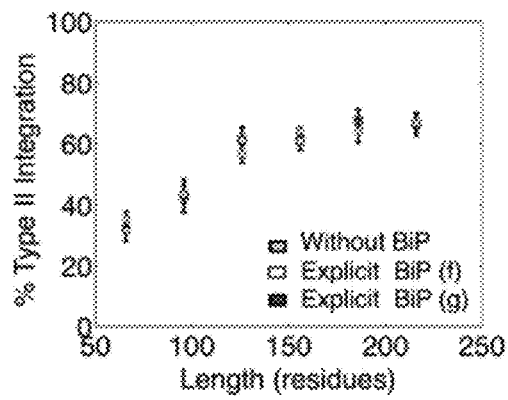
FIG. 4C

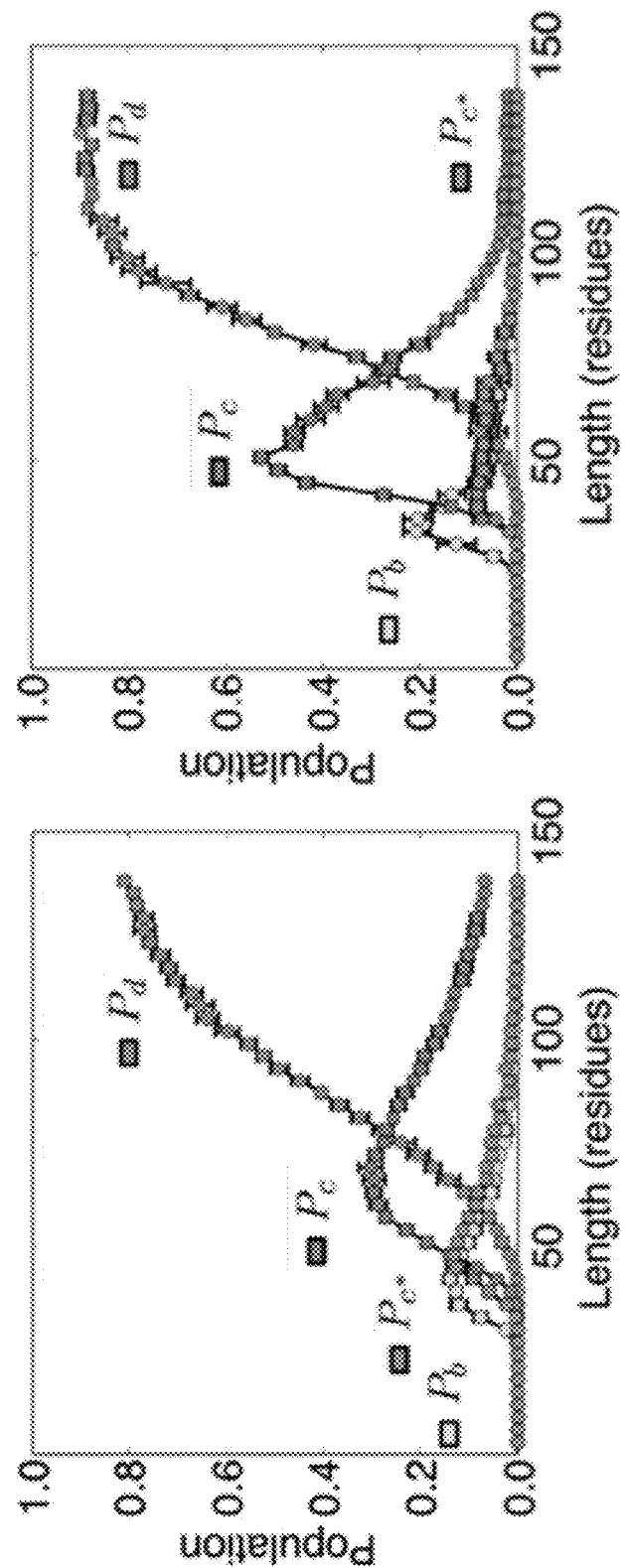

FIG. 9G
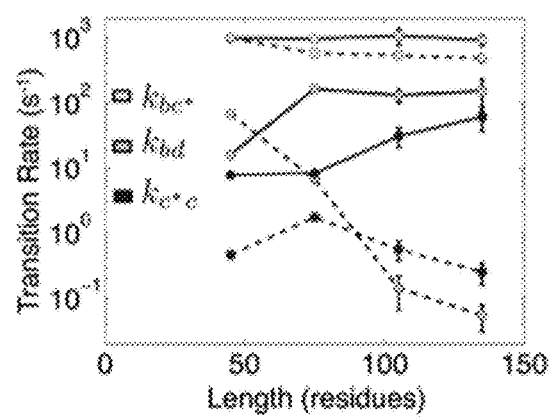
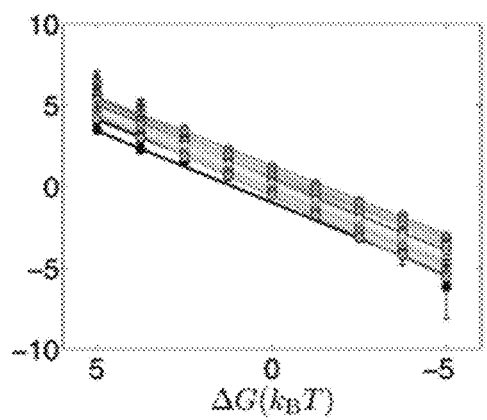
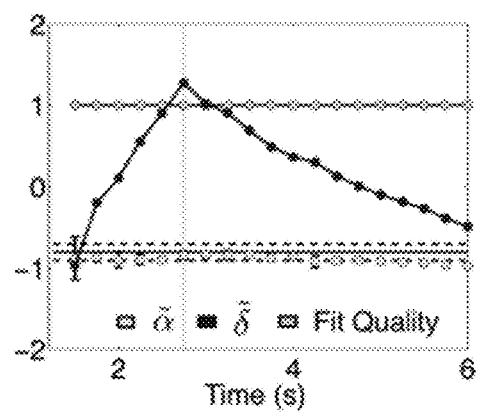
FIG. 9H
FIG. 9I

FIG. 18A

| Construct | Wt/Aatail* | Std Error | Net Charge | # Pos | # Neg |
|---|---|---|---|---|---|
| BpTatC | 0.266 | 0.042 | -3 | 4 | 7 |
| CjTatC | 0.037 | 0.003 | -2 | 2 | 4 |
| DrTatC | 0.119 | 0.012 | -1 | 2 | 3 |
| EcTatC | 0.988 | 0.111 | -5 | 4 | 9 |
| SaTatC | 0.667 | 0.047 | 2 | 2 | 0 |
| VcTatC | 1.230 | 0.143 | -7 | 1 | 8 |
| WsTatC | 0.393 | 0.041 | -3 | 0 | 3 |
| MtTatC Med | 0.469 | 0.060 | 3 | 5 | 2 |
| MtTatC FL | 0.050 | 0.007 | -1 | 5 | 6 |
| MtTatC GGP | 0.053 | 0.005 | 0 | 0 | 0 |
| MtTatC KATRIN | 0.094 | 0.010 | 2 | 2 | 0 |
| MtTatC Min | 0.174 | 0.025 | 0 | 0 | 0 |

| Ribosome | | | | Translocon | |
|---|---|---|---|---|---|
| x | y | x | y | x | y |
| -2 | -2.5 | -11 | -5.5 | -2.0 | -2.0 |
| -2 | -3.5 | -11 | -4.5 | -1.0 | -1.5 |
| -2 | -4.5 | -11 | -3.5 | 0.0 | -0.95 |
| -2 | -5.5 | -11 | -2.5 | 1.0 | -1.5 |
| -2 | -6.5 | -11 | -1.5 | 2.0 | -2.0 |
| -2 | -7.5 | -11 | -0.5 | -2.0 | 2.0 |
| -2 | -8.5 | -11 | 0.5 | -1.0 | 1.5 |
| -3 | -8.5 | -11 | 1.5 | 0.0 | 0.95 |
| -4 | -8.5 | -11 | 2.5 | 1.0 | 1.5 |
| -5 | -8.5 | -11 | 3.5 | 2.0 | 2.0 |
| -6 | -8.5 | -11 | 4.5 | | |
| -7 | -8.5 | -10 | 4.5 | | |
| -8 | -8.5 | -9 | 4.5 | | |
| -9 | -8.5 | -8 | 4.5 | | |
| -10 | -8.5 | -7 | 4.5 | | |
| -11 | -8.5 | -6 | 4.5 | | |
| -11 | -7.5 | -5 | 4.5 | | |
| -11 | -6.5 | -4 | 4.5 | | |

FIG. 19

|  |  | R | E | L | Q | V | P | X | Ribosome | LG$_n$ | LG$_\sigma$ | LG$_c$ |
|---|---|---|---|---|---|---|---|---|---|---|---|---|
| $\varepsilon_{ij}/\varepsilon$ | R | 1 | 1 | 1 | 1 | 1 | 1 | 1 | 1 | 1.5 | 1.5 | 1.5 |
| | E |  | 1 | 1 | 1 | 1 | 1 | 1 | 1 | 1.5 | 1.5 | 1.5 |
| | L |  |  | 1 | 1 | 1 | 1 | 1 | 1 | 1.5 | 1.5 | 1.5 |
| | Q |  |  |  | 1 | 1 | 1 | 1 | 1 | 1.5 | 1.5 | 1.5 |
| | V |  |  |  |  | 1 | 1 | 1 | 1 | 1.5 | 1.5 | 1.5 |
| | P |  |  |  |  |  | 1 | 1 | 1 | 1.5 | 1.5 | 1.5 |
| | X |  |  |  |  |  |  | 1 | 1 | 1.5 | 1.5 | 1.5 |
| $r_d/\sigma$ | R | 0 | 0 | 0 | 0 | 0 | 0 | 0 | 0 | 0 | 1.0 | 0 |
| | E |  | 0 | 0 | 0 | 0 | 0 | 0 | 0 | 0 | 1.0 | 0 |
| | L |  |  | 0 | 0 | 0 | 0 | 0 | 0 | 0 | 1.0 | 0 |
| | Q |  |  |  | 0 | 0 | 0 | 0 | 0 | 0 | 1.0 | 0 |
| | V |  |  |  |  | 0 | 0 | 0 | 0 | 0 | 1.0 | 0 |
| | P |  |  |  |  |  | 0 | 0 | 0 | 0 | 1.0 | 0 |
| | X |  |  |  |  |  |  | 0 | 0 | 0 | 1.0 | 0 |
| $r_a/\sigma$ | R | $2^{1/6}$ | $2^{1/6}$ | $2^{1/6}$ | $2^{1/6}$ | $2^{1/6}$ | $2^{1/6}$ | $2^{1/6}$ | $2^{1/6}$ | 2.5 | 2.5 | 2.5 |
| | E |  | $2^{1/6}$ | $2^{1/6}$ | $2^{1/6}$ | $2^{1/6}$ | $2^{1/6}$ | $2^{1/6}$ | $2^{1/6}$ | 2.5 | 2.5 | 2.5 |
| | L |  |  | $2^{1/6}$ | $2^{1/6}$ | $2^{1/6}$ | $2^{1/6}$ | $2^{1/6}$ | $2^{1/6}$ | 2.5 | 2.5 | 2.5 |
| | Q |  |  |  | $2^{1/6}$ | $2^{1/6}$ | $2^{1/6}$ | $2^{1/6}$ | $2^{1/6}$ | 2.5 | 2.5 | 2.5 |
| | V |  |  |  |  | $2^{1/6}$ | $2^{1/6}$ | $2^{1/6}$ | $2^{1/6}$ | 2.5 | 2.5 | 2.5 |
| | P |  |  |  |  |  | $2^{1/6}$ | $2^{1/6}$ | $2^{1/6}$ | 2.5 | 2.5 | 2.5 |
| | X |  |  |  |  |  |  | $2^{1/6}$ | $2^{1/6}$ | 2.5 | 2.5 | 2.5 |

FIG. 20

|     | R   | E    | L    | Q   | V    | P   | X        |
|-----|-----|------|------|-----|------|-----|----------|
| $q$ | 2.0 | -2.0 | 0.0  | 0.0 | 0.0  | 0.0 | 0.0      |
| $g/\varepsilon$ | 4.0 | 4.0 | -4.0 | 2.0 | -2.0 | 0.0 | variable |

FIG. 21

TRANSLOCON-ASSOCIATED BIOGENESIS FEATURES AND RELATED METHODS, SYSTEMS AND PRODUCTS

CROSS REFERENCE TO RELATED APPLICATIONS

The present application claims priority to U.S. Provisional Application No. 61/833,250 entitled "Method and Software for the Prediction and Refinement of Integral Membrane Protein Insertion into Cell Membranes and Protein Translocation Across Cell Membranes" filed Jun. 10, 2013, and to U.S. Provisional Application No. 61/872,103 entitled "Computational Algorithm for Designing Enhanced Expression of Integral Membrane Proteins" filed Aug. 30, 2013, each of which is incorporated herein by reference in its entirety. The present application is also related to U.S. patent application Ser. No. 14/301,070 filed on even date herewith, entitled "Translocon-Associated Biogenesis Features and Related Methods, Systems and Products", which is incorporated herein by reference in its entirety.

STATEMENT OF GOVERNMENT GRANT

This invention was made with government support under N00014-10-1-0884 awarded by the Office of Naval Research and 5DP1GM105385 awarded by the National Institutes of Health. The government has certain rights in the invention.

FIELD

The present disclosure relates to protein biogenesis and in particular to translocon-associated biogenesis features (TABFs) and related methods, systems and products.

BACKGROUND

Correct control of protein biogenesis has been a challenge in the field of biological molecule analysis, especially when aimed in particular, at protein expressed through the co-translational translocation pathway.

Whether for fundamental biology studies, medical applications or drug design, several methods are commonly used for the prediction of protein biogenesis, in particular for proteins, such as membrane proteins, that are intricately involved with a hydrophobic, or membrane micro-environment.

In particular, to date, there are several prediction software tools to determine a proteins structure, function, and ability to fold and insert properly into membrane micro-environment.

However, achievement of accurate prediction and control of protein biogenesis is still challenging.

SUMMARY

Provided herein are methods allowing in several embodiments prediction and/or control of translocon-associated protein biogenesis through control of translocon associated biogenesis features (TABFs) for proteins expressed in homologous or heterologous biological system in vitro or in vivo, and related, computer-based methods and systems as well as recombinant proteins.

According to a first aspect, a computerized trajectory-based method to represent translocon-associated protein trajectories is provided, comprising: i) representing, by a processor, amino and/or nucleic acids corresponding to a protein and an associated translocon as a plurality of coarse grain particles; ii) representing, by a processor, confinement and driving force effects of an active protein inserter; iii) representing, by a processor, interactions between the coarse grain particles; iv) calculating, by a processor, evolution of a chain of the coarse grain particles corresponding to the protein in the translocon as a function of time; v) based on steps i)-iv), building, by a processor, translocon-associated protein trajectories; and vi) providing, by a processor, spatial representation of the translocon-associated protein trajectories to a user.

According to a second aspect, a computer-based method to provide a protein or protein sequence with a desired translocon-associated biogenesis feature is provided, comprising: i) establishing a desired translocon-associated biogenesis feature of a protein sequence, the desired translocon-associated biogenesis feature selected from a) desired protein topology, b) desired partitioning between protein integration and protein secretion and c) desired protein expression level; ii) providing the protein or protein sequence with an initial set of translocon-associated biogenesis feature determinants; iii) representing by a computer one or more initial trajectories of the protein or protein sequence with the initial set of translocon-associated biogenesis feature determinants, the one or more trajectories determining an initial translocon-associated biogenesis feature of the protein or protein sequence with the initial translocon-associated biogenesis feature determinants; iv) comparing the initial translocon-associated biogenesis feature of the protein or protein sequence with the desired translocon-associated biogenesis feature of the protein or protein sequence; v) if the initial translocon-associated biogenesis feature of the protein or protein sequence is different from the desired translocon-associated biogenesis feature of the protein or protein sequence, modifying the initial set of translocon-associated biogenesis feature determinants, thus providing the protein or protein sequence with a modified set of translocon-associated biogenesis feature determinants; vi) representing by a computer one or more modified trajectories of the protein or protein sequence with the modified set of translocon-associated biogenesis feature determinants, the one or more modified trajectories determining a modified translocon-associated biogenesis feature of the protein or protein sequence with the modified translocon-associated biogenesis feature determinants; and vii) repeating steps iv)-vi) with the modified translocon-associated biogenesis feature in place of the initial translocon-associated biogenesis feature until the desired translocon-associated biogenesis feature is obtained, thus obtaining a set of translocon-associated biogenesis feature determinants suitable to be used for production of the protein or protein sequence with the desired translocon-associated biogenesis feature.

According to a third aspect, a computer-based method of screening proteins or protein sequences to provide proteins or protein sequences with a desired translocon-associated biogenesis feature is provided, comprising: i) establishing a desired translocon-associated biogenesis feature of a protein or protein sequence, the desired translocon-associated biogenesis feature selected from a) desired protein topology, b) desired partitioning between protein integration and protein secretion and c) desired protein expression level; ii) providing proteins or protein sequences, each having an associated set of translocon-associated biogenesis feature determinants; iii) for each protein or protein sequence, representing by a computer a trajectory of the protein or protein sequence, the trajectory determining a translocon-associated biogenesis feature of the protein or protein sequence; iv) for each protein or protein sequence, comparing the translocon-associated biogenesis feature of the protein or protein sequence with the desired translocon-associated biogenesis feature of the protein or protein sequence; and v) screening proteins or protein sequences for which the desired translocon-associated biogenesis feature has been determined in step iii) from proteins or protein sequences for which the desired translocon-associated biogenesis feature has not been determined in step iii).

According to a fourth aspect, a computer-based method of screening translocon-associated biogenesis feature determinants to provide proteins or protein sequences with a desired translocon-associated biogenesis feature is provided, comprising: i) establishing a desired translocon-associated biogenesis feature of a protein or protein sequence, the desired translocon-associated biogenesis feature selected from a) desired protein topology, b) desired partitioning between protein integration and protein secretion and c) desired protein expression level; ii) providing a protein or protein sequence, and multiple sets of associated translocon-associated biogenesis feature determinants; iii) for each set of translocon-associated biogenesis feature determinants, representing by a computer a trajectory of the protein or protein sequence, the trajectory determining a translocon-associated biogenesis feature of the protein or protein sequence; iv) for each set of translocon-associated biogenesis feature determinants, comparing the translocon-associated biogenesis feature of the protein or protein sequence with the desired translocon-associated biogenesis feature of the protein or protein sequence; and v) screening sets of translocon-associated biogenesis feature determinants for which the desired translocon-associated biogenesis feature has been determined in step iii) from sets of translocon-associated biogenesis feature determinants for which the desired translocon-associated biogenesis feature has not been determined in step iii).

According to a fifth aspect, a computer-based method for identifying translocon-associated biogenesis feature determinants of a given protein sequence is provided, comprising: i) providing a protein sequence with an associated set of translocon-associated biogenesis feature determinants; ii) establishing one or more desired translocon-associated biogenesis features of the protein sequence, the desired translocon-associated biogenesis features selected from a) desired protein topology, b) desired partitioning between protein integration and protein secretion and c) desired protein expression level; iii) providing one or more modified versions of the protein sequence by changing the translocon-associated biogenesis feature determinants associated with the protein sequence; iv) for each modified version of the protein sequence, representing by a computer a trajectory of the modified version of the protein sequence, the trajectory determining a translocon-associated biogenesis feature of the modified version of the protein sequence; and v) if the translocon-associated biogenesis feature of the modified version of the protein sequence matches one of the desired translocon-associated biogenesis features of the protein sequence, identifying the translocon-associated biogenesis feature determinants bringing to the desired translocon-associated biogenesis features of the protein sequence.

According to a sixth aspect, a computer-based protein sequence identification method is provided, comprising: i) providing a set of constraints on translocon-associated biogenesis feature determinants to be associated to a protein sequence; ii) providing a plurality of protein sequences, each having translocon-associated biogenesis feature determinants matching the set of constraints; iii) establishing a desired translocon-associated biogenesis feature of a protein sequence, the desired translocon-associated biogenesis feature selected from a) desired protein topology, b) desired partitioning between protein integration and protein secretion and c) desired protein expression level; iv) for each protein sequence, representing by a computer a trajectory of the protein sequence, the trajectory determining a translocon-associated biogenesis feature of the modified version of the protein sequence; and v) identifying the protein sequence bringing to the desired translocon-associated biogenesis feature.

According to a seventh aspect, a computer-based method for identifying correlations in a set of protein sequences is provided, comprising: i) providing a set of protein sequences, each protein sequence being associated to translocon-associated biogenesis feature determinants; ii) for each protein sequence, representing by a computer a trajectory of the protein sequence, the trajectory determining a translocon-associated biogenesis feature of the modified version of the protein sequence, the translocon-associated biogenesis feature being a protein topology, a partitioning between protein integration and protein secretion, or a protein expression level; and iii) for each protein sequence, comparing the translocon-associated biogenesis feature with the translocon-associated biogenesis feature determinants bringing to the translocon-associated biogenesis feature to determine possible correlations between translocon-associated biogenesis features and translocon-associated biogenesis feature determinants.

According to an eighth aspect, a computer-based method for identifying correlations between experimental data and computer-generated data in a protein sequence is provided, comprising: i) providing a protein sequence; ii) representing by a computer a plurality of trajectories of the protein sequence, each trajectory being determined in accordance with a distinct set of computer-executed parameters, each trajectory determining a translocon-associated biogenesis feature of the protein sequence, the translocon-associated biogenesis feature being a protein topology, a partitioning between protein integration and protein secretion, or a protein expression level; iii) correlating the translocon-associated biogenesis features determined in step ii) with experimentally obtained translocon-associated biogenesis features; and iv) identifying which of the translocon-associated biogenesis features determined in step ii) best correlate with the experimentally obtained translocon-associated biogenesis features.

According to a ninth aspect, a computer-based method for determining which modifications of a protein sequence do not substantially affect a translocon-associated biogenesis feature of the protein sequence is provided, comprising: i) providing a protein sequence; ii) representing by a computer a trajectory of the protein sequence, the trajectory determining a translocon-associated biogenesis feature of the protein sequence, the translocon-associated biogenesis feature being a protein topology, a partitioning between protein integration and protein secretion, or a protein expression level; iii) providing a plurality of modified versions of the protein sequence; iv) for each modified version, representing by a computer a trajectory of the modified version of the protein sequence, the trajectory determining a translocon-associated biogenesis feature of the modified version of the protein sequence; v) comparing the translocon-associated biogenesis feature of the protein sequence with the translocon-associated biogenesis features of the modified versions of the protein sequence; and vi) based on the comparison, determining which modifications of the protein sequence do not substantially affect the translocon-associated biogenesis feature of the protein sequence.

Further aspects of the present disclosure are provided in the specification, claims and drawings of the present application.

The methods and systems and related engineered proteins herein described allow in some embodiments predicting and/or refining biogenesis of membrane proteins, and in particular integral membrane protein insertion into cell membranes.

The methods and systems and related engineered proteins herein described allow in some embodiments predicting and/or refining protein translocation across cell membranes.

The methods and systems and related engineered proteins herein described allow in some embodiments increasing expression of integral membrane proteins or other protein expressed through a co-translational translocation pathway.

The methods and systems and related engineered proteins herein described allow in some embodiments predicting and/or refining biogenesis of secretory proteins that are translocated via the Sec cotranslational pathway, as well as integral membrane proteins that are integrated via the Sec pathway.

The methods and systems and related engineered proteins herein described allow in some embodiments predicting and/or refining biogenesis of proteins that undergo post-translocation integration/secretion via the Sec translocon.

The methods and systems and related engineered proteins herein described can be used in connection with applications wherein control of translocon associated protein biogenesis in in vivo or in vitro biological systems, is desired. Exemplary applications comprise laboratory applications, fundamental biological studies, diagnostics and medical applications, agriculture, food, biotechnology and pharmaceutical industries, as well as academic laboratories and other applications related to proteins (such as eukaryotic or bacterial secretory or membrane proteins and in particular integral membrane proteins), which are identifiable by a skilled person.

The details of one or more embodiments of the present disclosure are set forth in the description below. Other features, objects, and advantages will be apparent from the description and from the claims.

BRIEF DESCRIPTION OF DRAWINGS

FIGS. 3A-3F show charts illustrating CG Simulation Results for Integral Membrane Protein Topogenesis. In particular, FIGS. 3A-3C show charts illustrating fraction of type II integration as a function of protein MDL, with data sets that vary with respect to FIG. 3A SP charge distribution, FIG. 3B hydrophobicity, and FIG. 3C ribosomal translation rate. FIG. 3D shows a chart illustrating a fraction of CG trajectories that follow the type II loop pathway (light grey), type II flipping pathway (dark grey), and the type III pathway for membrane integration (white). FIG. 3E shows a chart illustrating the distribution of arrival times for CG trajectories at state f of type II integration via the loop pathway (light grey) and the flipping pathway (dark grey). FIG. 3F shows a chart illustrating an MDL dependence of the fraction of CG trajectories that follow each integration mechanism. Unless otherwise specified, error bars throughout the paper represent the SD of the mean. See also FIGS. 4A-4I.

FIGS. 4A-4I show charts and schematics illustrating additional CG Simulation Results for Protein Topogenesis, related to FIGS. 3A-3F. FIGS. 4A-4B show charts illustrating testing the sensitivity of SP orientation to hydrophobic patches in the mature domain of protein nascent chain. In particular, FIG. 4A shows a chart illustrating the MDL dependence of the fraction of CG trajectories that undergo type II integration, obtained using various values for the water-membrane transfer FE of the L-type CG bead in the protein mature domain (i.e., the CG bead representing the hydrophobic patch). The protein nascent chain SP sequence of RL6E is employed; the blue data set reported here is identical to that reported for the RL6E sequence in FIG. 3B. These results indicate that the simulation method exhibits significant dependence of the SP orientation to hydrophobic patches in the mature domain. FIG. 4B shows a chart illustrating the MDL dependence of the fraction of CG trajectories that undergo type II, obtained with different spacing between the SP and the hydrophobic patch in the mature domain. The dark grey data set was obtained using the mature domain sequence Q5LQn, as in the main text; this data set is identical to the dark grey data set in part FIG. 4A. The light grey data set was obtained by changing the mature domain sequence to Q9LQn. See text in Additional Validation and Predictions for Protein Topogenesis subsection Hydrophobic Patches in the Mature Domain for discussion. FIG. 4C shows the effect of explicit BiP binding on CG simulations of protein topogenesis. In CG simulations of protein topogenesis, the fraction of type II integration is plotted as a function of MDL for several sets of simulations. The first set (dark grey, filled) employs explicit BiP binding, and the CG trajectories undergoing type II integration are terminated only upon reaching state g (FIG. 2). The second set (dark grey, open) differs only in that CG trajectories undergoing type II integration are terminated upon reaching state f (FIG. 2). The third set (light grey) does not include explicit BiP binding, and the CG trajectories undergoing type II integration are terminated upon reaching state f. All data sets are obtained using the same insertion rate and SP sequence; the light grey data set is identical to that reported for the RL6E sequence in FIG. 3B. FIG. 4D shows a chart illustrating the analysis of the membrane integration mechanism upon increasing the length of the nascent chain N-terminal domain length. For two data sets, the fraction of CG trajectories that pass through each of the kinetic pathways in FIG. 2 is presented. The RL6E data set is identical to that presented in FIG. 3D. The Q3-RL6E data set is obtained in the same way, except that the protein nascent chain sequence is modified to include three additional Q-type CG beads at its N terminus. Comparison of the two data sets indicates that increasing the N-terminal domain length leads to a substantial decrease in the relative fraction of trajectories that undergo type II integration via the flipping mechanism. FIG. 4E shows a chart illustrating testing the effect of charged-residue mutations on the translocon. The figure plots type II integration fraction as a function of MDL. The light grey data set corresponds to the protein topogenesis results in FIG. 3A for the RL4E SP sequence. The dark grey data set is obtained using the same protein sequences and removing the positive charge on the lumenal side of the translocon LG (see FIG. 2); the negatively charged CG bead on the cytosolic side of the translocon LG is left unchanged. See the section 'Additional Validation and Predictions for Protein Topogenesis', subsection 'Charged-Residue Mutations on the Translocon' of the paper *Long-Timescale Dynamics and Regulation of Sec-Facilitated Protein Translocation*, B. Zhang and T. F. Miller, Cell Reports 2, 927-937 and S1-S24, Oct. 25 2012 (1), which paper is incorporated herein by reference in its entirety, for discussion. FIG. 4F shows testing the effect of negatively-charged N-terminal residues on SP orientation. The figure plots type II integration fraction as a function of MDL. The light and dark grey data set corresponds to the protein topogenesis results in FIG. 3A for the RL4E and QL4E SP sequences, respectively. Also shown are results for which the SP sequence includes either one (EL4E) or three (E3L4E) negatively-charged N-terminal CG beads. See the section 'Additional Validation and Predictions for Protein Topogenesis', subsection 'Positive versus Negative N-Terminal Charges on the Nascent Protein' of the paper *Long-Timescale Dynamics and Regulation of Sec-Facilitated Protein Translocation*, B. Zhang and T. F. Miller, Cell Reports 2, 927-937 and S1-S24, Oct. 25 2012, which paper is incorporated herein by reference in its entirety, for discussion. FIGS. 4G-4H show schematics illustrating testing the effect of distant charged-residue mutations on the nascent-protein mature domain. In particular, FIG. 4G shows a schematic representation of the CG bead sequences for Proteins 1 and 2, which have three TM domains and which differ only with respect to the charge distribution in the third. On the other hand, FIG. 4H shows a schematic illustrating the possible overall topologies for the two multispanning proteins. FIG. 4I shows a schematic illustrating the fraction of CG insertion trajectories that lead to the Ncyt/Cexo topology for Protein 1 (light grey) and Protein 2 (dark grey). See the section 'Additional Validation and Predictions for Protein Topogenesis', subsection 'Charged-Residue Mutations on the Nascent-Protein Mature Domain: A Multispanning Protein Example' of the paper *Long-Timescale Dynamics and Regulation of Sec-Facilitated Protein Translocation*, B. Zhang and T. F. Miller, Cell Reports 2, 927-937 and S1-S24, Oct. 25 2012, which paper is incorporated herein by reference in its entirety, for discussion.

FIG. 6A shows a chart illustrating stop-transfer efficiency as a function of H-domain hydrophobicity. FIG. 6B shows charts illustrating dependence of stop-transfer efficiency upon (B1) slowing ribosomal translation rate from 24 res/s to 6 res/s, (B2) including explicit lumenal BiP binding, (B3) increasing the CTL from 75 residues to 105 residues, and (B4) replacing the hydrophobic beads in the protein C-terminal domain with hydrophilic beads; in each subpanel, the dashed line corresponds to the sigmoidal fit of the data in FIG. 6A. FIG. 6C shows a chart illustrating equilibrium transition rates between the states in FIG. 5 as a function of H-domain hydrophobicity. For each color, the forward rate is indicated with the solid line, and the reverse rate is indicated with dashed line. FIG. 6D shows a chart illustrating dependence of stop-transfer efficiency on CTL and the ribosomal translation rate, obtained for protein sequences with H-domain transfer FE of $\Delta G=-1.25 k_B T$. Error bars represent the SD of the mean. See also FIGS. 7A-7H.

FIGS. 7A-7B show charts illustrating testing the effects of hydrophobic patches in the C-terminal domain on H-domain stop-transfer efficiency. In particular, FIG. 7A shows a chart illustrating the dependence of stop-transfer efficiency on the peptide CTL, ribosomal translation rate, and mature domain sequence. The results reported with filled data points are identical to those reported in FIG. 6D. The results reported with open data points correspond to the same calculations with the simulation method, except that hydrophobic patches in the C-terminal domain of the protein nascent chain are removed. Specifically, the V-type beads in the C-terminal domain of the protein sequence used to construct FIG. 6D are substituted with Q-type CG beads. FIG. 7B shows a nonequilibrium population of the states in FIG. 5 at the time of stop translation for proteins of various CTL. The CG trajectories used to make this figure employed protein sequences without hydrophobic patches and a ribosomal translation rate of 24 res/s; the results correspond exactly to the open-red data points in part A. Comparison of the nonequilibrium populations in this figure with the results obtained for proteins that include hydrophobic patches (FIG. 9E) reveals enhancement of Pc. See the section 'Additional Validation and Predictions for Stop-Transfer Efficiency', subsection 'Hydrophobic Patches in the C-Terminal Domain' of the paper *Long-Timescale Dynamics and Regulation of Sec-Facilitated Protein Translocation*, B. Zhang and T. F. Miller, Cell Reports 2, 927-937 and S1-S24, Oct. 25 2012, which paper is incorporated herein by reference in its entirety, for discussion.

FIG. 7C shows a chart illustrating testing the effect of charged-residue mutations flanking the nascent-protein H-domain. The figure plots stop-transfer efficiency as a function of H-domain hydrophobicity. The black dashed line is the sigmoidal fit to the data presented in FIG. 6A. The solid line data set is obtained using the same protein sequences, except that the three CG beads in the C-terminal domain that directly flank the nascent protein H-domain are mutated from being hydrophilic and neutral (Q-type) to being hydrophilic and positively charged (R-type).

FIG. 7D shows a chart illustrating dependence of the average translocation time for secreted proteins on H-domain hydrophobicity. The protein sequences and stop-transfer simulation protocols employed here are the same as those used to construct FIG. 6A.

FIGS. 7E-7F show charts illustrating a comparison of the stop-transfer efficiency versus H-domain hydrophobicity from experiment (Hessa et al., 2005) (2) and simulation (from FIG. 6A); data points obtained from experiment and simulation are reported in dark grey and light grey, respectively. The experimental results are obtained using the Lep protein sequence, which has a CTL of 71 residues and a hydropathy profile. The CG simulation results are obtained using proteins with a similar CTL of 75 residues (25 beads). Experimentally, stop-transfer efficiency is measured as a function of the number of Leu residues (n) in the 19-residue H-domain sequence, $Ala_{19-n} Leu_n$. Assuming the additivity of the transfer FE between residues, the water-membrane transfer FE for the H-domain is thus $\Delta G = (19-n)\Delta G_{Ala}^{wat-mem} + n\Delta G_{Leu}^{wat-mem}$. In the absence of water-membrane transfer FE values for the amino acid residues, experimental data points in FIG. 7E are instead plotted using available water-octanol transfer FE values (Wimley et al., 1996) (i.e., $\Delta G_{Leu}^{wat-mem} \approx \Delta G_{Leu}^{wat-oct} = -1.25$ kcal/mol and $\Delta G_{Ala}^{wat-mem} \approx \Delta G_{Ala}^{wat-oct} = 0.5$ kcal/mol). Sigmoidal fits are included to guide the eye. FIG. 7E shows an agreement between the simulation and the experiment is reasonable, given the simplicity of the simulation method and the uncertainty in determining the experimental water-membrane transfer FE for the H-domain. For example, a difference of only 0.15 kcal/mol in the residue water-octanol transfer FE values and the water-membrane transfer FE values would lead to the improved comparison between theory and experiment shown in FIG. 7F. Previous work suggests that residue transfer FE differences of this magnitude are to be expected (Gobas et al., 1988; Moon and Fleming, 2011; Vaes et al., 1998).

FIGS. 7G-7H show the effect of explicit BiP binding on CG simulations of stop-transfer efficiency. In particular, FIG. 7G shows stop-transfer efficiency as a function of H-domain hydrophobicity, for CG simulations that either include (dark grey) or do not include (light grey) explicit BiP binding. All data sets are reported using the same insertion rate and CTL; the light grey data set is identical to that reported in FIG. 6A, and the dark grey data set is identical to that reported in panel B2 of FIG. 6B. FIG. 7H shows the dependence of stop transfer efficiency on CTL, insertion rate, and explicit BiP binding. The data sets that are reported with filled symbols do not include explicit BiP binding; these two data sets are identical to the results presented in FIG. 6D. The data sets that are presented with open symbols correspond to simulations that differ only in that they include explicit BiP binding. For the CG simulations of stop-transfer efficiency, including explicit BiP binding leads to reduced stop-transfer efficiency, since backsliding along the secretion pathway is inhibited. However, qualitative features of the CG simulation results are unaffected by inclusion of explicit BiP binding. See in the section 'Explicit Modeling of Lumenal BiP' in the above mentioned paper for discussion.

FIG. 8A shows the coordinate system for the simulation method. CG beads for the ribosome and translocon are shown in dark grey and light grey, respectively; the membrane is shown using a rectangular shape. The coordinates are reported in distance units of σ=8 Å. FIG. 8B shows regions of the simulation method used in defining intermediates states for protein translocation and membrane integration. Region A (grey) encloses the cytosolic region; region B (white) includes the translocon channel; region C consists of the hydrophobic interior of the membrane; region D (light grey) includes the lumenal region. Each region is defined as a rectangle with the indicated vertex position. All coordinates are reported in the coordinate system described in the left panel; CG bead positions are described in FIG. 19.

FIGS. 9A-9I show schematics and charts illustrating an analysis of kinetic pathways from the CG Simulations of stop-Transfer Efficiency, related to FIG. 5 and FIGS. 6A-6D. In particular, FIGS. 9A-9D show a schematic of minor pathways observed for cotranslational TMD partitioning.

More in particular, FIG. 9A shows a schematic for pathway PI, the protein nascent chain partitions into the membrane directly from state d (i.e., with the H-domain on the lumenal side of the membrane), and then the H-domain backslides into the membrane without passing through the translocon. States d and f are defined as in FIG. 5. Trajectories are determined to have passed through the PI pathway if neither state b nor state c* is visited along the transition from d to f.

FIG. 9B shows a schematic for pathway PII, the H-domain transits to the lumenal side of the membrane from state c without re-entering the translocon channel, and the C-terminal domain translocates across the membrane bilayer without passing through the translocon channel. States c and e are defined as in FIG. 5. Trajectories are determined to have passed through the PII pathway if neither state b nor state c* is visited along the transition from c to e.

FIG. 9C shows a chart illustrating as a function of CTL, the percentage of CG trajectories that undergo membrane integration (light grey, open) versus secretion (dark grey, open), as well as the percentage that follow the PI (light grey, closed) and PII (dark grey, closed) pathways. A protein nascent chain sequence was used for which the H-domain transfer FE is $\Delta G = -1.25 k_B T$; the ensemble of trajectories analyzed here corresponds to the light grey data set in FIG. 6D. Membrane integration via the PI pathway is most often observed at long CTL, since a longer CTL provides more opportunities for the C-terminal tail to partition through the translocon LG. H-domain secretion via the PII pathway is most often observed at short CTL, since short C-terminal domains create a smaller energetic barrier to direct translocation through the membrane (i.e., with short C terminus, the H-domain is less stably anchored in the membrane). Note that throughout the full range of CTL considered here, neither of these pathways is the dominant mechanism for protein translocation or membrane integration.

FIG. 9D shows a chart illustrating as a function of H-domain hydrophobicity, the percentage of CG trajectories that undergo membrane integration (light grey, open) versus secretion (dark grey, open), as well as the percentage that follow the PI (light grey, closed) and PII (dark grey, closed) pathways. A protein nascent chain sequence for which the CTL is 75 residues was employed; the ensemble of trajectories analyzed here corresponds to the data in FIG. 6A.

FIGS. 9E-9F show charts illustrating non-equilibrium populations of the states in FIG. 4 at the time of stop-translation for proteins of various CTL, obtained from over 2000 CG trajectories for co-translational TMD partitioning. These results are obtained using the same protein nascent chain sequences described in the Direct Simulation of Cotranslational TMD partitioning section of the main text, with H-domain hydrophobicity $\Delta G = -1.25 k_B T$. The CG trajectories employ a ribosomal translation rate of either 24 res/s (FIG. 9E) or 6 res/s (FIG. 9F). Three observations from this figure pertain to the discussion in the Kinetic and CTL Effects in TMD partition Section of the main text. First, at longer CTL (>75 residues), slowing ribosomal translation leads to an enhancement of Pd with respect to Pc. Second, at shorter CTL (<75 residues), slowing translation does not lead to enhancement of Pd with respect to Pc. Third, at both insertion rates, Pd increases monotonically, such that longer CTL always correspond to more population in state d at the time at which translation ends.

FIG. 9G shows a chart illustrating equilibrium transition rates between the states in FIG. 5 as a function of CTL for the protein nascent chain. For each color, the forward rate is indicated with the solid line, and the reverse rate is indicated with dashed line. As is described in connection with FIG. 6C, the transition rates are calculated from long, equilibrium CG trajectories for which the protein C terminus is fixed at the ribosome exit channel. First, note that the forward and reverse transition rates between states b and c* are fast in comparison to the other transitions and relatively independent of CTL. Second, note that the forward transition rate $k_{bd}$ increases with CTL, whereas the reverse transition rate $k_{db}$ (grey, dashed) dramatically decreases with increasing CTL. This decreased backsliding of the H-domain from state d into state b is of relevance to the discussion in the Kinetic and CTL Effects in TMD partitioning section of the main text. State b is destabilized relative to state d at long CTL because of crowding in the ribosome-translocon junction. A similar trend is seen in the forward and reverse rates between states c and c*.

FIGS. 9H-9I show charts illustrating numerical validation of a simulation method for TMD partitioning, obtained from the ensemble of CG trajectories used to obtain FIG. 6A. In particular, FIG. 9H shows a chart illustrating the left-hand side of Equation S5 of the paper *Long-Timescale Dynamics and Regulation of Sec-Facilitated Protein Translocation*, B. Zhang and T. F. Miller, Cell Reports 2, 927-937 and S1-S24, Oct. 25 2012, which paper is incorporated herein by reference in its entirety, is plotted at various times t during the TMD partitioning and for proteins with a range of H-domain hydrophobicity, $\Delta G$. The set of data points that correspond to each time t (indicated by color) is then fit to the linear function $-\beta \alpha \Delta G + \delta$ (see FIG. 9I). The linear fit parameters $\alpha$ and $\delta$ (white and black, respectively) obtained at each time t, as well as the R-squared measure of quality of the linear fit (grey), are plotted. The solid line at −0.80 corresponds to the value for a obtained by directly fitting the data in FIG. 6A with Equation 1. Dashed lines indicate the threshold of 95% certainty in this direct fit. The vertical red line at t=2.75s corresponds to the time at which translation of the protein nascent chain completes. Reference can also be made to the section 'Analytical Model for TM Partitioning' of the above mentioned paper, incorporated herein by reference in its entirety.

In particular, FIG. 11A shows ribbons diagram of the structure of AaTatC (pdbid 4HTS). TMDs as defined in the text are numbered loops are the stretches of amino acids connecting the TMDs. Helices are numbered. FIG. 11B shows a topology representation of TatC as used in the expression studies with a GFP C-terminal tag. FIG. 11C shows representative experimental flow cytometry data used to determine expression levels. The bottom panel shows the fluorescence of the gated cell population. The grey peak represents the GFP negative population (AaTatC no GFP). The light grey peak shows low to medium expression of GFP, while the black peak shows high levels of GFP. FIG. 11D shows sequence alignment of AaTatC and MtTatC (SEQ ID NO:1; SEQ ID NO: 2). TMs that are swapped in the chimeras are highlighted. For this and subsequent figures, AaTatC is shaded dark grey and MtTatC is shaded light grey. FIG. 11E shows the relative expression of the two proteins. Here and in subsequent figures, error bars represent standard deviation.

FIG. 12A shows a map of pETKatGFP, a PIPE cloning vector based on pET33. Parts that are modified from the original vector are highlighted in dark gray. The multiple cloning site was replaced by a chloramphenicol resistance gene and the suicide gene ccdB, which are flanked by TEV and 3C protease sites to allow for common primers to clone into each vector. Immediately after the 3C site is the gfp gene with an octa-histidine tag. FIG. 12B shows a map of pETKatN9, which is similar to FIG. 12A without the C-terminal GFP tag and a N-terminal nona-histidine tag instead. FIG. 12C shows a representative flow cytometry result of AaTatC, AaTatC+GFP, and MtTatC+GFP. The top panel shows side scatter plotted versus forward scatter to give an indication of the size of the examined bacteria. The red lines indicate the gated region with cells outside this line excluded during analysis. The lower panel is a plot of side scatter versus GFP fluorescence.

FIG. 13A shows topology diagrams of representative chimeras at the top; the naming convention is the first two letters refer to the backbone TatC and in parenthesis the swapped regions are indicated (e.g. Mt(AaH1) means: the first TM of MtTatC has been replaced by the equivalent TM of AaTatC. The bottom panel shows a chart illustrating the results of expression trials of various chimeras using the MtTatC backbone. FIG. 13B shows topology diagrams similar to FIG. 13A for chimeras. The convention Aa#/#Mt indicates that a chimera was generated split between the indicated TMs (e.g. Aa3/4Mt has the first half of AaTatC and the second half, starting at TM4 of MtTatC). The bottom panel shows a chart illustrating the results of expression trials of various chimeras using the AaTatC backbone and split chimeras. In the case of swaps versus split chimeras, several resulted in equivalent TM architecture with only the loops being different (e.g. Aa(MtH4-6) has the same TMs as Aa3/4Mt). These are indicated by the same patterns in the bar graph. For these, an unpaired two-tailed student T-test was performed to indicate the level of significance of the difference.

FIG. 14A shows a topology highlighting the chimera where only the AaTatC C-tail is swapped into MtTatC. FIG. 14B shows expression trials focused on the 4/5 loop and the C-tail with additional controls. AaTatC tail swaps are colored dark gray in this and subsequent bar graphs. The asterisks indicate the statistically significant constructs by ordinary one-way ANOVA followed by Dunnett's multiple comparison test to MtTatC. FIG. 14B also shows expression tests comparing various TatC homologs from and their Aa C-tail swap. An unpaired two-tailed student T-test was performed for constructs with and without Aa C-tail and significant differences are indicated by asterisks (* p=0.0003; ** p<0.0001), no asterisk indicates no significant difference.

FIG. 16A shows a chart illustrating the fraction of AaTatC, MtTatC, and Mt(Aa C-tail) simulation trajectories that yield the correct membrane topology, normalized with respect to the AaTatC wild type. FIG. 16B shows a diagram of the desired TABF on the left hand side and a frequently observed misintegrated TABF where translocation of TMD6 leads to an incorrect final topology for the TatC homologs. FIG. 16C shows a chart illustrating a comparison of the fraction of desired TABF, determined by simulation, and the rate of experimentally observed expression. For each of the tested sequences, the ratio for expression of the wild type and its C-tail swap chimera is plotted on the y-axis against the ratio for integration of the wild type and its C-tail swap chimera on the x-axis. For 6 out of tested TatC homologs improved integration corresponds to improved expression. The values, excluding the outlier for Vc, are fit by linear regression with a correlation (R) of 0.5.

FIGS. 18A-18C show charts and schematics illustrating a comparison of TatC homologs. In particular, FIG. 18A shows a sequence alignment of TatC from D*einococcus radiodurans* (Drad) (SEQ ID NO: 6), *Mycobacterium tuberculosis* (Mtub) (SEQ ID NO: 11), *Aquifex aeolicus* (Aaeo) (SEQ ID NO: 3), *Escherichia coli* (Ecol) (SEQ ID NO: 7), *Vibrio cholerae* (Vcho) (SEQ ID NO: 9), *Bordetella parapertussis* (Bpar) (SEQ ID NO: 4), *Campylobacter jejuni* (Cjej) (SEQ ID NO: 5), *Wollinella succinogenes* (Wsuc) (SEQ ID NO: 10), and *Staphylococcus aureus* (Saur) (SEQ ID NO: 8) highlighting charged residues and labeled TMDs in FIG. 18B. The vertical line defines the beginning of the C-tail. FIG. 18B shows a ribbons diagram of the AaTatC structure with helices depicted as cylinders and colored as in FIG. 18A. The glutamate (E165) in TMD4 is shown. FIG. 18C shows a table illustrating properties of the C-tails tested in FIGS. 14A-14B. For each construct the columns correspond to, Wt/AaTail, the value of the ratio of wild type/Aa C-tail with the standard error (see FIG. 17D), the net charge, the sum of the total charges counted for each tail; #Pos, number of Arg and Lys residues; and #Neg, number of Asp or Glu residues.

FIG. 19 shows a table illustrating CG Bead Positions for the Ribosome and the Translocon (Units in σ), related to FIGS. 1, 2 and 5. The CG bead for the ribosomal exit tunnel is located at [−10, −5]. An illustration of the coordinate system is provided in FIGS. 8A-8B.

FIG. 20 shows a table illustrating parameters for the Non-Bonded Interactions (see Equation 2), related to FIGS. 3A-3F and FIGS. 6A-6D.

FIG. 21 shows a table illustrating CG Bead Charges (q) and Water/Membrane Transfer Free Energies (g), Related to FIGS. 3A-3F and FIGS. 6A-6D.

In FIG. 25A he desired TABF for TatC is shown schematically on the left. When applying the simulation method on TatC homologs an undesired TABF, as shown on the right, is frequently observed. The simulation method reveals that introduction of the Aa-tail sequence prevents translocation of the C-terminal loop. Introduction of the Aa-tail improves TABF for (FIG. 25B) MtTatC, (FIG. 25C) DrTatC, (FIG. 25D) VcTatC, (FIG. 25E) BpTatC, (FIG. 25F) CjTatC, and (FIG. 25G) WsTatC.

Figure 1:
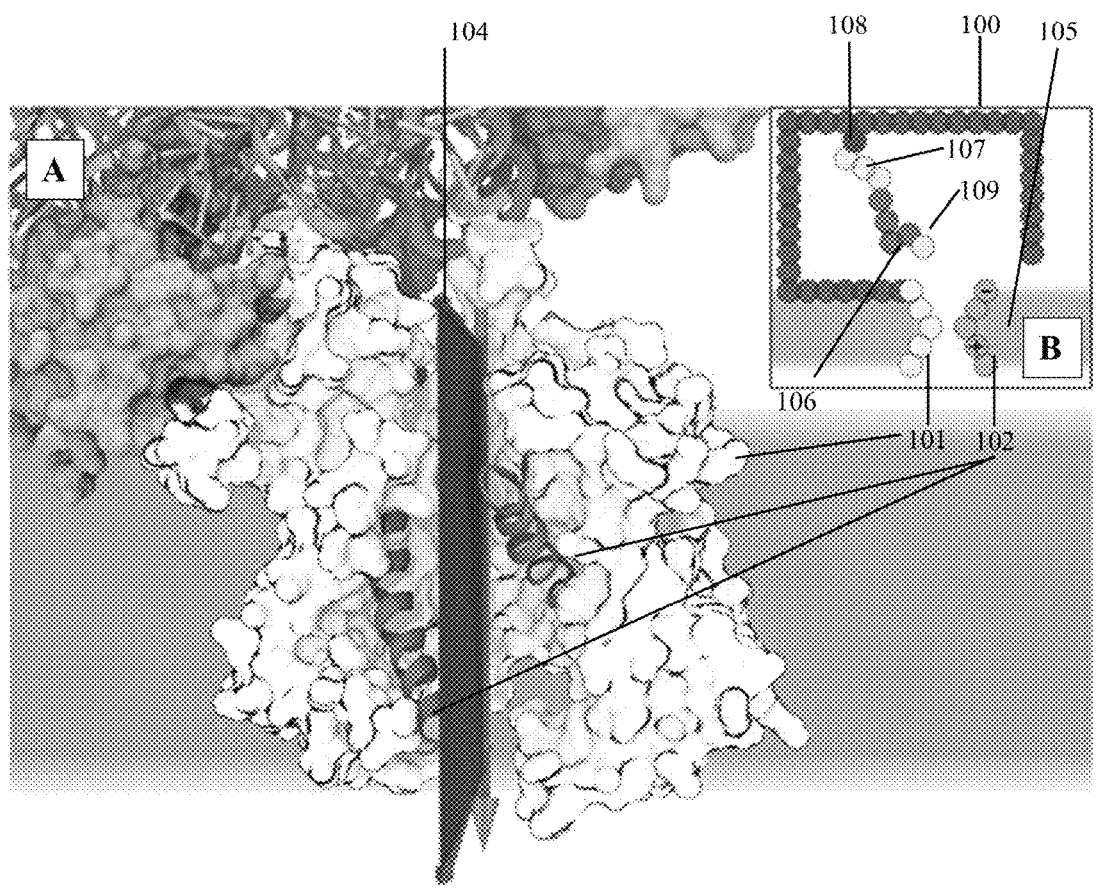
FIG. 1 shows a schematic representation of structural features of the Cotranslational Sec Machinery. The ribosome (100) is shown in complex with the Sec translocon (101-102). The simulation method projects the protein nascent chain dynamics onto the plane (104) that intersects the translocon channel axis and that bisects the lateral gate (LG) helices (102). With reference to inset B of FIG. 1, the simulation method includes beads for the translocon (101-102), the ribosome (100), and the protein nascent chain (106-109). The LG helices are the shaded part of the translocon (102), and the C-terminal bead of the nascent chain (108) is attached to the ribosomal exit tunnel. The lipid membrane (105) is implicitly simulated by a position dependent potential acting on the nascent chain CG particles. The nascent chain is composed of beads for the SP (106, 109) and the mature domain (107).

The "tertiary structure" of a protein refers to the three-dimensional structure of a protein, stabilized by non-covalent interactions among non-adjacent segments of the protein and optionally by one or more additional compounds or ions interacting through covalent or non-covalent interactions with one or more segments of the proteins. Exemplary non-covalent interactions stabilizing the three dimensional structure of the proteins comprise non-specific hydrophobic interactions, burial of hydrophobic residues from water, specific tertiary interactions, such as salt bridges, hydrogen bonds, the tight packing of side chains, chelation and disulfide bonds and additional interactions identifiable by a skilled person. Exemplary covalent interactions among compounds or ions and segments of the protein comprise, N-linked glycosylation, cytochrome C haem attachment and additional interaction identifiable by a skilled person. In some instances, multiple proteins can form a protein complex, also called a multimer, with one or more identifiable three dimensional structures stabilized by non-transitory interactions between the multiple proteins. The three-dimensional structure of the protein complex is also called "quaternary structure" of the complex. Accordingly, the quaternary structure can be stabilized by some of the same types of non-covalent and covalent interactions as the tertiary structure as will be understood by a skilled person. Multimers made up of identical subunits are referred to with a prefix of "homo-" (e.g. a homotetramer) and those made up of different subunits are referred to with a prefix of "hetero-", for example, a heterotetramer, such as the two alpha and two beta chains of hemoglobin. A "cofactor" indicates any molecule that forms non-transitory covalent or non-covalent interactions with a protein in vitro or in vivo. "Non-transitory interactions" as used herein indicates interactions between proteins or related segments—that are detectable by laboratory techniques such as immunoprecipitation, crosslinking and Forster Resonance Energy Transfer (FRET), crystallography, Nuclear Magnetic Resonance (NMR) and additional techniques identifiable by a skilled person.

Proteins can be identified by x-ray crystallography, purification and direct sequencing, immuno precipitation, and a variety of other methods as understood by a person skilled in the art. Proteins can be provided in vitro or in vivo by several methods identifiable by a skilled person.

Embodiments herein described relates to biogenesis of a protein. "Protein biogenesis" indicates a multistep biological pathway leading to the protein synthesis in a biological system, wherein the biological system indicates any system wherein protein expression is performed in connection with a biological membrane or a biomimetic environment. The biological membrane indicates enclosing or separating membrane that acts as a selectively permeable barrier within a biological cell. Exemplary biological membrane comprises the Endoplasmic Reticulum or mitochondrial membranes of eukaryotes and inner membrane of bacteria. The biomimetic environment indicates an amphipathic lipid bilayer or any other amphipathic lipid environment suitable to accommodate segments of a protein Exemplary biomimetic comprise micelles lipid cubic phase o, a proteolyposome and additional biomimetic identifiable by a skilled person. Exemplary biological systems comprise a eukaryotic cell, a prokaryotic cell, an archeal cell, or a cell-free system. A "cell-free" system indicates an in vitro system that contains the basic components required for the multistep biological pathway to take place outside a cellular environment. In some embodiments of biological systems of the disclosure, protein synthesis can occur via a process called translation. During translation, mRNA is read by ribosomes to generate a protein polypeptide chain. This process is performed by an array of components within the cell including ribosomes and transfer RNA (tRNA), which serves as an adaptor by binding amino acids on one end and interacting with mRNA at the other end; the latter pairing between the tRNA and mRNA ensures that an amino acid corresponding to a codon in the mRNA is added to the chain. The term "ribosome" as used herein refers to a minute particle consisting of RNA and associated proteins found in large numbers in the cytoplasm of living cells. Ribosomes bind messenger RNA and transfer RNA to synthesize polypeptides and proteins. Examples include the 80S ribosome in Eukaryotes. Translation usually proceeds in an N- to C-terminal direction with additional amino acids added by the ribosome to the C-terminus as determined by the mRNA sequence which encodes the primary structure of the protein. Once translated, a protein's primary structure can be modified by modifications of the polypeptide chain and/or amino acid monomers identified as posttranslation modifications. Post translational modifications can affect topogenesis and folding of a protein. Exemplary posttranslational modifications comprise protease digestion (e.g. secreted proteins containing signal sequences which can be cleaved), attachment of functional groups (such as acetate, phosphate, various lipids and carbohydrates), changes in the chemical nature of an amino acid (e.g. citrullination), formation of intrapolypeptide bonds (e.g. formation of disulfide bridges) and additional modification of the covalent bonds in the polypeptide chain and/or amino acid residues not performed by the ribosome The term "protein folding" as used herein indicates the creation of secondary, tertiary, and quaternary structure during and after translation. Protein folding is driven a wide array of forces such as the non-specific hydrophobic interactions and the burial of hydrophobic residues from water and specific tertiary interactions, such as salt bridges, hydrogen bonds, the tight packing of side chains, and disulfide bonds. Protein folding occurs by creating non-covalent interactions that increase the stability of the protein. The term "topogenesis" refers to the establishment of the topology of a protein. The term "topology" refers to the orientation of segments in regards to the membrane such that a given segment is either on the same side of the membrane as the inserter, the opposite side of the membrane as the inserter, or within the interior of the membrane. Topology can be determined by x-ray crystallography, NMR, FRET, crosslinking studies, and additional techniques identifiable by a skilled person. Folding of the protein can result in one or more tertiary structure depending on the primary structure, posttranslational modifications, biological environment where the folding occurs. Typically a specific tertiary structure is associated to one or more biological functions of the proteins detectable with techniques identifiable by a skilled person. Exemplary functions comprise catalysis, binding of one or more ligand, transport across the membrane and additional functions identifiable by a skilled person. Typically a protein expressed in a biological system that provides the native environment of the protein folds to form a native structure associated with one or more tertiary structures and a topology which characterizes a functionality of the protein in the native environment. Accordingly a native structure when formed gives the protein the ability to perform one or more required functions in the native environment. An example would be an enzyme that when folded to a tertiary structure and/or resulting in a topology that differ from the ones of the native structure, has a diminished capacity to perform its catalytic activity.

The term "express" as used herein in reference to "protein expression" indicates the production of a protein in a biological system with one or more defined topologies associated with a stabilized tertiary and/or quaternary structure of the protein. "Expression level" indicates the amount of an expressed protein that achieves a defined topology. Expression of a protein is typically associated with translocation of the protein to an appropriate destination in the cell or outside of the cell. For proteins that are membrane proteins or secretory proteins translocation typically comprises movement of the protein with respect to the biological membrane and includes passage of the protein or segments therefore through and/or into the membrane.

The term "co-translational translocation pathway" as used herein relates to a process where translocation of a protein across the membrane or integration into the membrane begins while the protein is still being synthesized on the ribosome through interaction of the nascent protein with a translocon. The term "post-translational translocation pathway" as used herein relates to a process where translocation of a protein across the membrane or integration into the membrane begins after the protein has been synthesized (e.g. by ribosome) through interaction of the protein with a translocon with the assistance of a SecA protein. The term "translocation" is intended to mean any translocon-associated process, such as any process mediated by the translocon, and in particular changes in the position of at least one protein segment relative to a membrane due to interaction of the protein or segments thereof with the translocon.

The term "translocon", as used herein, indicates a protein complex that forms a channel in the biological membrane through which insertion of membrane proteins and translocation of a secreted proteins occur. Translocons comprise an internal core pore structure and lateral gates helices. The "lateral gate" and "lateral gate helices" indicate the area of the translocon, which opens to allow interaction between the core of the translocon and lipids in the membrane, facilitating transfer of protein segments into the membrane. A translocation process results in the protein crossing a hydrophobic lipid bilayer all or in part. Accordingly a translocon can be used to integrate nascent proteins into the membrane itself (membrane proteins) by passing segments of the protein typically comprising secondary structures such as alpha helices of the protein (e.g. nascent chain in a co-translational translocation pathway) through the lateral gate into the membrane. Eukaryotes can also have translocons associated with the chloroplast and the mitochondria. In prokaryotes, a translocon transports polypeptides across the plasma membrane or integrates membrane proteins. Known translocons include the heterotrimeric Sec61 protein complex in eukaryotes or SecYEG protein complex in bacteria. The major structural components of the translocon are transmembrane helices (TM), alpha helices that lie in the membrane or at least partially cross the membrane. TMs are composed mainly of hydrophobic resides. "Transmembrane segments" or TMS" indicates segments that are primarily composed of transmembrane helices. Transmembrane helices can be connected by structured or unstructured segments herein called loops. "non-TM segment" indicates segments of membrane protein that are not part of a transmembrane helix. The translocon pore can open to allow passage of material across the membrane. The lateral gate of the translocon can also open to allow material to pass laterally from the interior of the channel into the membrane.

A "protein inserter" is defined as any molecular machine and in particular any protein or protein complexes (possibly comprising a nucleic acid moiety), that interacts with the protein to be translocated, provides confinement of the protein to be translocated on one side of the translocon while also providing a driving force for the movement of protein to be translocated through the translocon. This driving force comprises the creation of additional amino acids or portions thereof (e.g. side chains or alpha carbon) associated with the protein to be translocated and/or forces of restraint between the C-terminus of the protein to be translocated and/or mechanical forces of pushing the protein to be translocated towards the translocon. In particular, inclusion of a protein inserter in a biological system increases the rate of insertion of a polypeptide to the translocon in a processive fashion, which is detectable by measuring a rate of translocation for a protein undergoing translocation or of a portion thereof, as compared to the rate a same system without the protein inserter. Exemplary protein inserters are the ribosome (for co-translational translocation or membrane integration) or the SecA motor (for post-translational translocation or membrane integration).

The position of the protein inserter can be used as a reference point to identify sides of the membrane comprising the translocon where the side comprising a protein inserter can also be identified as "protein-inserter side of the membrane" while the side opposite to "protein inserter side of the membrane" of the membrane is called and the "Trans-protein-inserter side of the membrane". Accordingly, a protein is inserted into the translocon by a protein-inserter that is positioned at one end of the translocon. Since the translocon spans the membrane, the non-membrane region of space is thus divided into a protein inserter side which is on the same side as the membrane inserter and a trans-protein-inserter side in that which is on the opposite side of the membrane from the protein inserter. Exemplary protein inserter sides comprise cytosolic side of an ER membrane having a luminal side as a trans-protein-inserter side.

In case of protein inserter formed by a ribosome translocating a protein through a translocon in the ER membrane occurs in the cytosolic space, so that in eukaryotic cells the protein inserter side in also indicated as the "cytosolic side of the membrane" and the non-protein inserter side is also indicated as the "luminal side of the membrane".

Proteins that are transported across membranes through a translocon comprise proteins that contain one or more membrane spanning helices such as integral membrane proteins, proteins residing in the ER, periplasmic proteins, and extracellular proteins (e.g. secretory proteins).

Proteins that are transported across membranes through a translocon are targeted to the translocon by a signal sequence which can be a cleavable or not cleavable during or following translocation of the protein. Examples of proteins having a cleavable signal sequence are secretory proteins and type I membrane proteins as will be understood by a skilled person. A cleavable signal sequence typically comprise a hydrophobic stretch of 7-15 predominantly apolar residues, and then anchored in the membrane by a subsequent stop-transfer sequence, a segment of about 20 hydrophobic residues that halts the further translocation of the peptide and acts as a transmembrane anchor. Examples of membrane proteins having a non-cleavable signal sequence (signal anchor sequence) comprise type II and type III membrane proteins. A "signal anchor sequence" as used herein is generally longer than a cleaved signal (about 18-25 mostly apolar amino acids), since it spans the lipid bilayer as a transmembrane helix. A signal anchor sequence lacks a signal peptidase cleavage site and they can be positioned internally within the polypeptide chain. However, like cleaved signals, a signal anchor sequence induces the translocation of their C-terminal end across the membrane.

The term "secretory proteins" as used herein refers to a protein that is targeted to the translocon, passes through the translocon and results in a stabilized tertiary structure having no segment inserted into the membrane. In some instances, targeting of secretory proteins or other proteins (e.g. integral membrane proteins) to the translocon is performed by signal sequence "Signal sequence" or "signal peptide" indicates a protein segment that causes it to be targeted to the translocon. Examples of secretory proteins include collagen and insulin. Secretory proteins may be transiently attached the membrane due the integration of the signal sequence into the membrane. These proteins are distinct from membrane proteins. Cleavage often occurs between the signal sequence and the remainder of the protein ("cleavable signal sequence"). In some instances, however the signal sequence is not cleaved and anchors the protein to the membrane ("signal anchor sequence").

The term "membrane protein" or "integral membrane protein" "IMP" or "transmembrane proteins" as used in the present disclosure indicate a protein including at least one transmembrane domain (TMD) or (TM) which indicates any protein segment which is thermodynamically stable in a membrane, as will be understood by a skilled person. In particular in integral membrane proteins a TMD is typically formed by a single transmembrane alpha helix. The translocon facilitates the insertion of alpha helical transmembrane proteins by movement of TMs trough the lateral gate. "Alpha helical membrane protein" indicates a membrane protein with at least one alpha helix TM.

Three types of membrane proteins can be distinguished based on topology and of the type of a signal sequence presented at the N-terminus or C-terminus of the protein. Type I, Type II, and Type III. The term "Type I" as used herein refers to membrane proteins that are initially targeted to the ER by an N-terminal, cleavable signal sequence. Examples of Type I include Glycophorin and LDL receptor. The term "Type II" as used herein refers to membrane proteins wherein a "signal-anchor sequence" is responsible for both insertion and anchoring. Examples of Type II proteins include Transferrin receptor and galactosyl transferase. The term "Type III" as used herein refers to membrane proteins which translocate their N-terminal end across the membrane. Examples of Type III proteins include Synaptotagmin, neuregulin, and cytochromes P-450.

Both membrane proteins and secretory proteins in some embodiments can be chimaeras, fusion proteins, wild type proteins and non-naturally occurring or engineered proteins. "Chimaera" or "chimera" indicates a protein or protein sequence produced by swapping segments between multiple protein sequences having a different protein primary structure one related to the other. A "fusion protein" indicates a protein or protein sequenced produced by attaching multiple domains or proteins in sequel. "Wild-type" in reference to a protein from a specific species refers to the protein with the same primary structure as what is found in nature in that species. A "non-naturally occurring" or "engineered" protein refers to a protein with a primary structure differing from a wild type protein at least by one amino acid residue.

As the protein to be translocated (e.g. the nascent chain) is inserted into the translocon, segments of the protein to be translocated (e.g. nascent chain) undergo either integration, retention or secretion. "Integration" indicates the partitioning of a protein segment into the membrane during translocon associated biogenesis. "Secretion" indicates the passage of a segment from the protein-inserter side of the membrane to the trans-protein-inserter side of the membrane during translocon associated biogenesis. "Retention" indicates the preservation of a protein segment on the protein-inserter side of the membrane during translocon associated biogenesis. The "degree" to which a particular segment undergoes integration, retention, or translocation occurs refers to the proportion of trajectories which end with that segment being integrated, retained, or translocated.

The term "Translocon Associated Biogenesis Feature" or "TABF", refers to features of a protein that are due to the protein's interaction with a translocon and are detectable from the three dimensional structure of a protein undergoing or having completed translocation. Exemplary TABFS comprise topology of the translocated protein the frequency of any segment of the protein residing within the membrane, and the levels of protein expression.

In experimental settings TABF topology of the translocated protein and the frequency of any segment of the protein residing within the membrane, can be detected by topological mapping methods including tagging of the translocated protein with a label such as a fluorescent protein or a catalytic domain, substituted cysteine accessibility method, site specific label detection, deuterium exchange mass spectrometry, oxidative labeling and additional techniques identifiable by a skilled person based on the specific translocated protein observed.

In experimental setting TABF the levels of protein expression can be detected by measurement of activity of the protein, measurement of the amount of the protein translocated (e.g. by quantitative mass spectrometry isolation and measurement of the protein, concentration), tagging of the translocated protein with a label such as a fluorescent protein or a catalytic domain, observation of results from polyacrylamide gel electrophoresis or any other chromatographic techniques (e.g. liquid chromatography, gas chromatography, PAGE and additional techniques identifiable by a skilled person) and affinity techniques such as Western blot, immunoprecipitation and additional techniques identifiable by a skilled person.

The term "TABF determinants" indicates any feature of the protein primary structure or the biological environment that can have an effect on TABFs as can be detected in experimental settings and/or modeling settings by comparing the TABFs at issue for a protein at issue before and after a modification of one or more of the TABFs determinants.

TABF determinants can be classified into three types: TABF determinants associated to the primary structure of non-TM segments (non-TM segments TABF determinant), TABF determinants associated to the primary structure of TM segments (TMs) (TM segments TABF determinant), and TABF determinants associated with the biological system where the protein expression occurs and that do not depend on the protein primary structure (biosystem TABF determinants).

In particular, non-TM segments TABF determinants and TM segment TABF determinants (herein also indicated as sequence related or primary structure related TABF determinants) comprise features of the TM segments and non-TM-segment respectively and related residues which can affect one or more TABFs as will be understood by a skilled person Exemplary non-TM segments TABF determinants and TM segments TABF determinant comprise:

number of charged residues in the segment(e.g. number of D, E, K, R and/or H residues in the segment), location of charged residues in a segment (e.g. location relative to the nearest TMS or membrane, other charged residues, or other determinants), length of the segment (e.g. length of a luminal loop or the length of a tail or N-terminal segment), hydrophobicity/polarity of the segment (e.g. the segment hydrophobicity value obtained by summing up the experimentally determined amino acid hydrophobicity values (e.g. by measuring partition of the residues between aqueous and non-aqueous phases) for each residue in the segment), any covalent interactions or non-covalent interactions within a segment or between two more segments (e.g. disulfide bonds formed between two cysteines within a segment or between segments; joint chelation of ions, van der Waals interactions, hydrogen bonds, and ionic interactions between moieties presented on residues within a segment or between moieties presented on residues in different segments), any secondary structure of one or more TM and/or non-TM segments or any combination of secondary structures within a segment (e.g. comprise loops, alpha helices and beta sheets and additional), any covalent or non-covalent interactions of a segment with one or more membrane components such as lipids, cholesterols, membrane proteins and additional component identifiable by a skilled person (e.g. disulfide bonds formed between two cysteines between a segment and a membrane component; van der Waals interactions, hydrogen bonds, and ionic interactions between moieties presented on a segment and moieties presented in the membrane component), any interactions of a segment with one or more cofactors (e.g. loops can form surfaces that interact with chaperons, other proteins, or cofactors non-covalently via ionic-, polar-, van der Waals, or other interactions or covalently such as via disulfide bridges; TM or non-TM segments can form structures that serve as receptors for specific proteins or molecules), presence or absence of structure makers and secondary structure breakers in one or more segments (e.g. a proline in a non-TM alpha-helix as a breaker of the non-TM segment; or alanine in a TM alpha-helix as a maker of the TM alpha helix), any post-translational modifications of one or more segments (e.g. O-, and N-linked glycosylation, phosphorylation, ubiquitination, S-nitrosylation, methylation, N-acetylation, lipidation, proteolysis), interactions between non-TM segments and TM-segments (e.g. a TMS forming a hydrophilic cavity into the membrane into which TMS residues in this area can interact with residues in non-TM loops).

Non-TM segment TABF determinants further comprise inclusion of soluble segments (segments that are stable in a non-membrane environment, e.g. luminal or cytosolic) at any non-TM segment, the C-terminus or the N-terminus (e.g. inclusion of a maltose binding protein domain or a zinc finger motif), and inclusion of amphipathic (possessing both hydrophilic and lipophilic properties) segments into a non-TM segment (e.g. any segment that lies along the membrane interface regions.

TM segment TABF determinants and non-TM segment TABF determinant also comprise residue attributes of one or more residues of a non-TM segment. The term "residue attributes" refers to properties of an amino acid that distinguish the amino acid from other amino acids. Exemplary residues attributes that constitute TABF determinants comprise an amino acid charge, amino acid polarity, amino acid hydrophobicity (e.g., water/membrane transfer free energy), amino acid hydrogen bonding capability, amino acid aromaticity, amino acid size/excluded-volume, amino acid reduction potential, amino acid covalent bonding capability, and chelation ability or ligand binding ability.

In particular, with respect to "charge" of an amino acid residue, all amino acids can carry a charge on their carboxyl and amino groups. In addition their side-chain is either neutral or carries a positive or a negative charge. Arginine (R) and lysine (K) have a side-chain with an amino group that under physiological conditions can be positively charged. Glutamate (E) and aspartate (D) have side-chains with a carboxyl group that is negatively charged under physiological conditions. Histidine (H) has a secondary amine in its ring with a $pK_a$ of 6.5. Hence, histidines may also carry a positive charge but because they are not charged as often as R, K, E, and D, H is not always classified or treated as a charged residue. Non-naturally occurring amino acid can be charged based on the one or more moieties presented on the backbone alpha carbon, amine and/or carboxyl group.

As to the residue attribute "polarity" of an amino acid residue, in addition to charged side chains amino acids can also have side-chains that are neutral but polar. Serine (S), Threonine (T), and Tyrosine (Y) contain —OH as a functional group. Due to the oxygen's high electronegativity, shared electrons are shifted towards the alcohol group and thus producing a polar moment. The amino acids glutamine (Q) and asparagine (N) are also polar due to a terminal amide group. Non-naturally occurring amino acid can have a polarity based on the one or more moieties presented on the backbone alpha carbon, amine and/or carboxyl group.

With respect to the residue attribute "hydrophobicity" of an amino acid refers to the physical value that can be related to the amino acid residue attraction a non-aqueous solvent which is measurable by methods such as octanol/water partition (octanol scale) values (Wimley et al., 1996) and the free energy contribution of replacing a residue in a trans-membrane segment with the residue whose hydrophobicity is being measured (interface scale) (Hessa et al., 2005) (2) (Hessa et al., 2007) (3). Exemplary hydrophobicity values are $\Delta G$ 0.50±0.12 in the octanol scale or $\Delta G$ 0.17±0.06 in the interface scale (for naturally occurring Alanine) as well as $\Delta G$−2.09±0.11 in the octanol scale and/or $\Delta G$−1.85±0.06 (for naturally occurring Tryptophan) The interior of the membrane is hydrophobic so hydrophobic residues are more stable in the membrane than hydrophilic residues. Hydrophobicity generally decreases with increasing polarity and charge.

Residue attribute "hydrogen bonding" relates presence or absence in an amino acid residue of a hydrogen attached to an electronegative atom such as Nitrogen (N), Oxytegen (O) and Fluorine (F) and/or and an atom that has a free electron pair, such as nitrogen, or oxygen in the amino acid. Typical energies for hydrogen bonds range between 4 and 13 kJoule/mol. Intramolecular hydrogen bonds of a polypeptide's backbone carboxy group with the backbone's amide group can provide stability to secondary structure elements.

Residue attribute "aromaticity" refer to presence or absence in the amino acid of a conjugated ring of unsaturated bonds, lone pairs, or empty orbitals that exhibit a stabilization stronger than would be expected by the stabilization of conjugation alone. The following naturally occurring amino acids contain aromatic side-chains: tyrosine (Y), tryptophan (W), phenylalanine (F), and histidine (H).

The residue attribute "excluded volume" is a measurement of the size of a molecule. In case of amino acids excluded volume refers to the volume that is inaccessible by water molecules as will be understood by a skilled person.

Residue attribute "reduction potential" is the measure of the ability of a chemical species to acquire electrons and therefore to be reduced, which can be measured by the amino acid residue tendency to acquire electrons as compared to a reference electrode (e.g. a saturated hydrogen electrode).

Residue attribute "covalent bonding capability" indicates the capability to engage in covalent bonds which is measurable by NMR or Mass spectrometry indicating formation or non-formation of a covalent bond with respect to a reference amino acid. For naturally occurring amino acid, cysteines provides an example of an amino acid residue having a covalent bonding capability in particular through the —SH group of the cys side-chains. It can form disulfide bonds with other cysteines and it can be exploited for crosslinking with other molecules that also contain a —SH group. Other side chains such as for example the primary amine in lysine or the carboxy groups in glutamate and aspartate can also be used to form covalent bonds with non-amino acids. This is often exploited in crosslinking experiments. Posttranslational modifications also utilize the covalent bonding capabilities of various amino acids, e.g., asparagine in the case of N-linked glycosylation.

Residue attribute "chelation ability" or "ligand binding ability" refers to an amino acid ability to reversibly bind ligands or ions. Atoms with free electron pairs have the potential to coordinate ions. The free electron pair of the secondary amide in histidine for example can be employed for this purpose, alone or in combination with additional amino acid residues having chelation ability (e.g. ability to chelate iron and nickel).

TABF determinants associated with the biological system where the protein expression occurs and that do not depend on the nascent protein sequence comprise:

modifications in the primary, secondary, tertiary and/or quaternary structure of one or more proteins forming the translocon in the biological system (e.g. deletion or insertion of one or more residues or a segment, including segments forming the whole protein), modifications in the primary, secondary, tertiary and/or quaternary structure of one or more proteins forming the protein inserter in the biological system (e.g. deletion or insertion of one or more residues or a segment, including segments forming the whole protein), changing the rate at which segments pass through the translocon detectable by measurement of the energy driven inserter expends energy (e.g. the rate at which SecA introduces a polypeptide into the translocon can be measured by the rate at which SecA hydrolyzes ATP), wherein change in said rate can be performed by modulating factors such as additives (e.g. cycloheximide), codon-dependence, mRNA sequence, concentration of components (tRNAs), and changes in the protein inserter machine, changes of the membrane/lipid environment (e.g. addition of fatty acid, lipids, and other hydrophobic molecules to the growth medium, or providing the necessary genes for biosynthesis of molecules of the lipid bilayer, either by plasmids or by integration into the genomic DNA, or changing the biological system in which the translocation occur), changes in temperature of the biological system in which translocation occurs (e.g. detectable by measurement of the average kinetic energy of all molecules in the biological system), changes in pH of the aqueous environment of the biological system in which translocation occurs (e.g. detectable by measurement of the electrical potential of the environment as compared to a reference electrode), changes in the media of the biological system where translocation occurs (e.g. by changing in the composition and/or concentration of nutrients, ranging from minimal media to full media; in addition to buffers, specific amino acids, trace elements, lipids, salts, and additional medium component that are identifiable by a skilled person), changes in pressure of the biological system in which translocation occurs (e.g. detectable by measurement of the force per unit area applied by the molecule in the biological system), changes in applied electric or magnetic fields, of the biological system in which translocation occurs (e.g. detectable by electromagnetic spectrum analyzer), changing the biological system in which expression occurs (e.g. by changing the species in which expression occurs, or by changing the biological system in which translocation occurs from in vitro to in vivo or vice versa), and presence or absence of cofactors (such as Binding Immuno Globulin protein (BiP) or any other cofactors identifiable by a skilled person upon reading of the present disclosure).

Figure 23A:
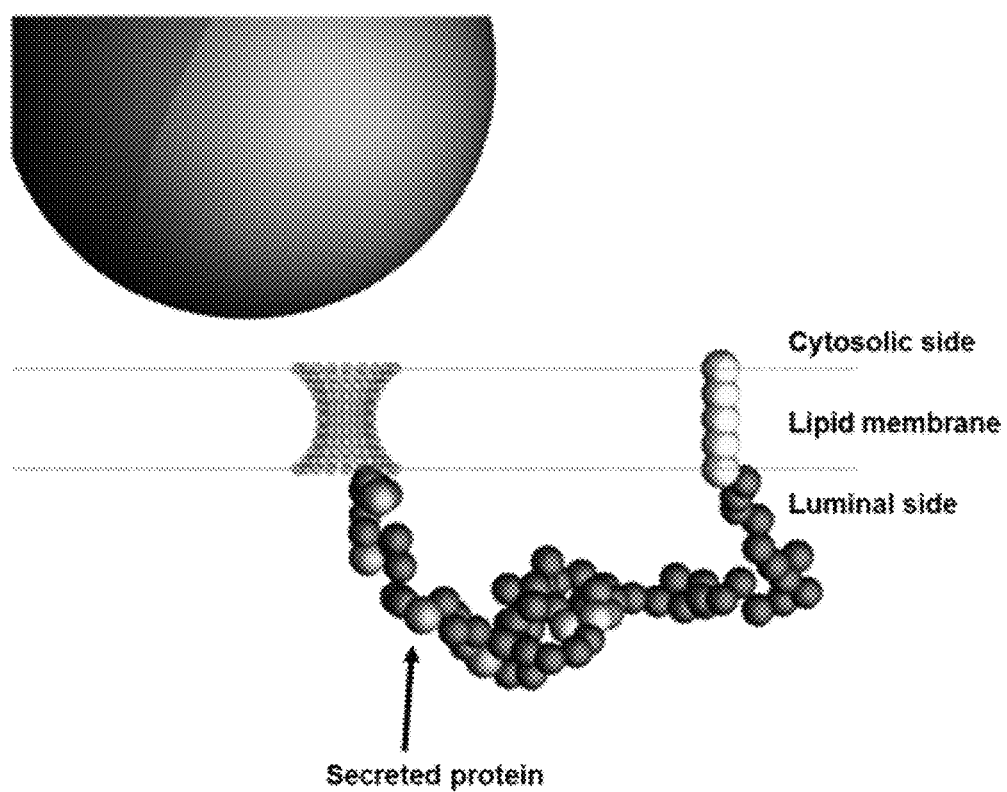
FIG. 23A shows example trajectory data from a 3-dimensional embodiment of the simulation method, corresponding to a configuration in which the mature domain of the protein was secreted.
Figure 23B:
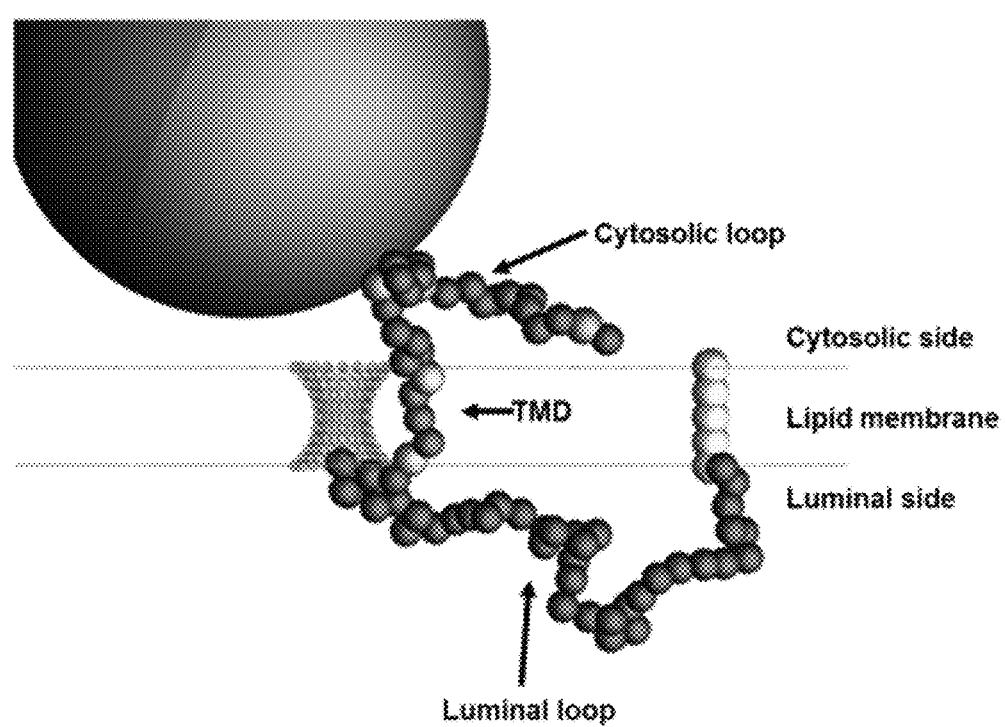
FIG. 23B shows trajectory data from a 3-dimensional embodiment of the simulation method, corresponding to a configuration in which a segment of the mature domain was integrated into the membrane.
Figure 23C:
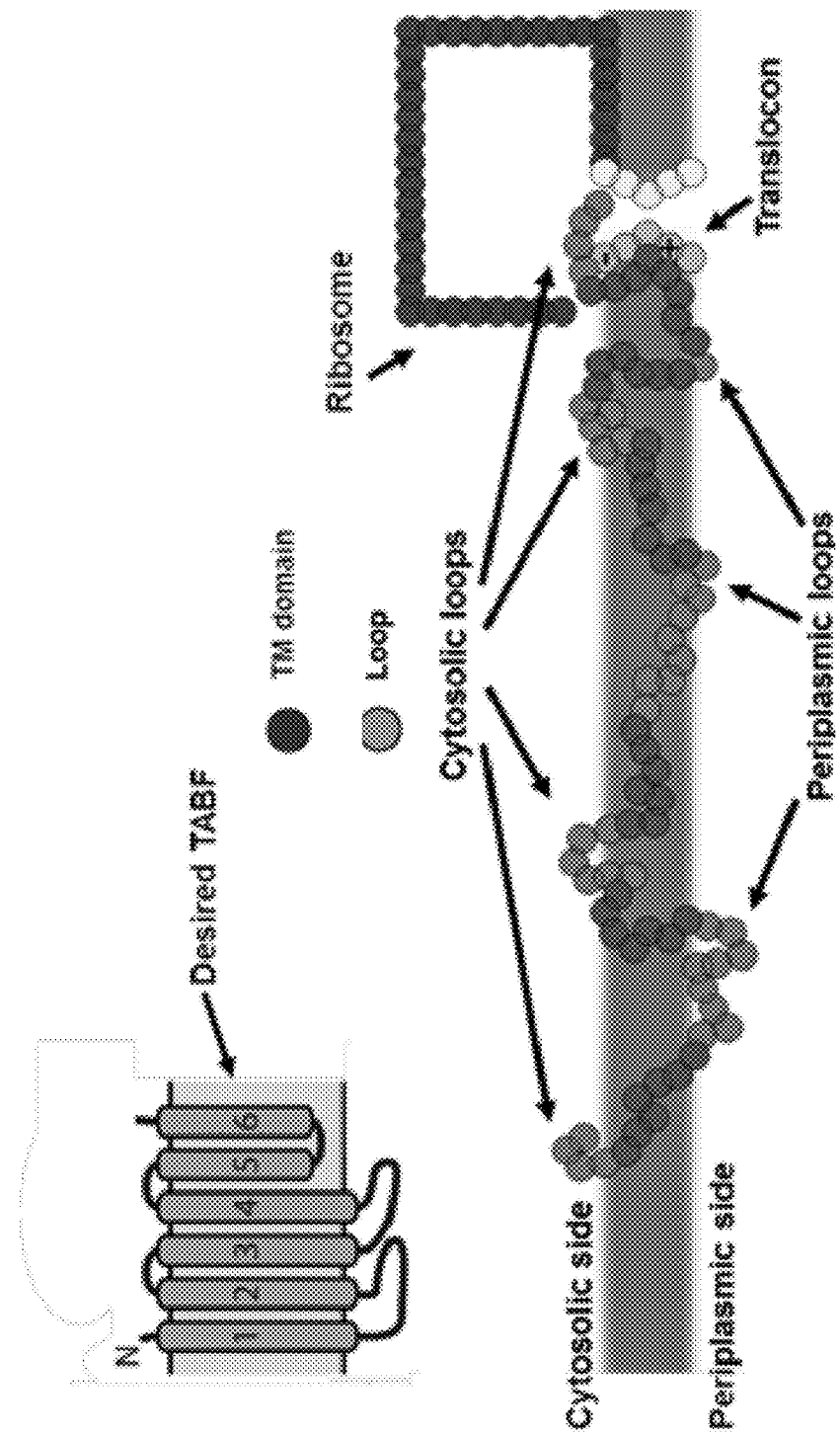
FIG. 23C shows example trajectory data from a 2-dimensional embodiment of the simulation method, used to simulate the translocon in *E. coli*. The desired TABF is shown schematically for reference, this trajectory exhibits the desired TABF, as can be determined by comparing of the CG particle coordinates to the desired TABF, in this case a multispanning topology with 6 TMDs and with the N-terminal loop retained in the cytosolic side, and subsequent loops alternating between the periplasmic and the cytosolic side of the membrane.

In accordance with embodiments of methods and systems herein described, modification of TABF determinants resulting in modification of TABF for one or more proteins can be determined based on a model providing simulated trajectories of a protein with a sequence simulated with coarse-grain particles in a system comprising the protein, the translocon and a protein inserter, where the driving forces of the protein inserter can also be represented by creation of additional CG beads associated with the nascent protein. Forces of restraint between the C-terminus of the nascent protein and/or mechanical forces of pushing the protein to be translocated (e.g. a nascent protein) towards the translocon can also be taken into account.

The term "coarse-grain particles", "CG particles", or "CG beads", as used herein is defined as an entity in the simulation method that has coordinates, interactions, and properties. CG particles can be time-evolved in the simulation approach and are used to describe the protein-inserter, the nascent protein, and the translocon. CG particles represent at least one atom, and can be used to represent groups of atoms if loss is detail is required to make the simulations tractable, as is also done in the example section where one CG particle represents three amino acids. CG particles have a bead type; the bead type of a particle determines the interactions it has in the context of the simulated system.

A "simulation trajectory" as used herein refers to the exact coordinates of the CG particles that are time evolved in the simulation method over the course of the simulation. For each CG particle the simulation trajectory describes the exact location in space at every point in time for the simulated event. For CG beads that can correspond to more than one discrete state (such as the open/closed states of the CG beads for the translocon lateral gate helices), then the trajectory additionally describes the discrete state for the CG beads at every point in time for the simulated event. The trajectory data completely specifies the nascent chain TABF. The simulation data produced by the computational methods described herein can be assessed to determine the TABF for a given amino acid sequence. The coordinates of the protein undergoing or having completed translocation can be obtained from the simulated trajectory, during and after the translocation event at any point in time. The TABFs are fully specified by the coordinates of the protein undergoing or having completed translocation (e.g. a nascent protein in a co-translation translocation pathway). In the case of integration for any segment of the protein, the coordinates of all particles in that segment of the protein will be inside the lipid region, as shown per example in FIG. 5 panel f. In the case of secretion for a segment, the coordinates of all particles in that segment will be in the luminal region, as shown per example in FIG. 5 panel e. In the case of retention for a segment, the coordinates of all particles in that segment will be in the cytosolic region, as shown per example in FIG. 23B for the indicated cytosolic loop segment. TABFs can be determined for all segments comprising the protein, for IMPs the topology is defined by the coordinates of the hydrophilic segments between TMs; that can be either retained, or secreted. TMs can be identified by their localization into the membrane region, and secreted proteins are characterized by all CG particles being localized on the luminal side of the lipid membrane.

The fraction of simulations for a given sequence that exhibit desired TABFs serves as a metric for the propensity of the simulated conditions to lead to the desired TABFs. A desired TABF in the sense of the disclosure indicates a TABF that meets a set of specified requirements or criteria.

The TABF after the translocon-associated biogenesis has been completed can be assessed by considering the coordinates of the protein sequence at a point in time where translocon associated biogenesis has fully completed in the simulation, for example 30 seconds after the last amino acid has exited the ribosomal exit tunnel, as was done in the specific example concerning TatC, or after the nascent protein particles are all at a minimum distance away from the translocon, for example 16 nm as was done in the simulations discussed in connection with the description of FIG. 4. The TABFs of the protein sequence can be assessed over a window in time of at a minimum 1 simulation time-step in length, typically on the order of 100 ns, or by comparing the probability of a segment to be in the cytosol, lumen, or membrane region over a time window comprising multiple simulation steps. The latter approach can reduce noise due to sporadic excursion of loops into the membrane region, or of membrane domains into the cytosol or lumen.

Figures 16A, 16B, 16C:
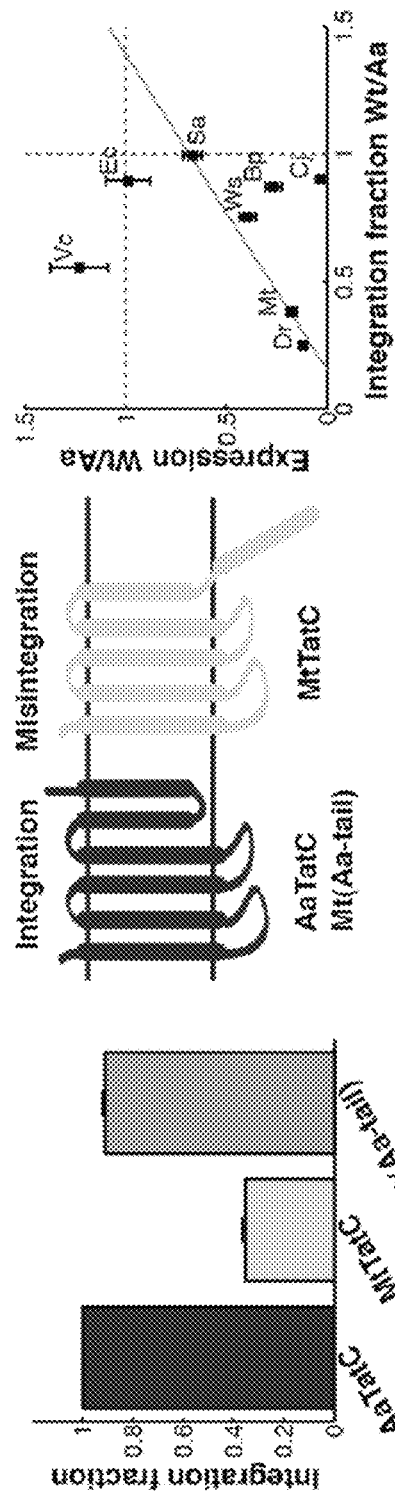
FIGS. 16A-16C show charts and diagrams illustrating mechanistic explanation of C-tail stabilization. In particular.
Figures 17A, 17B:
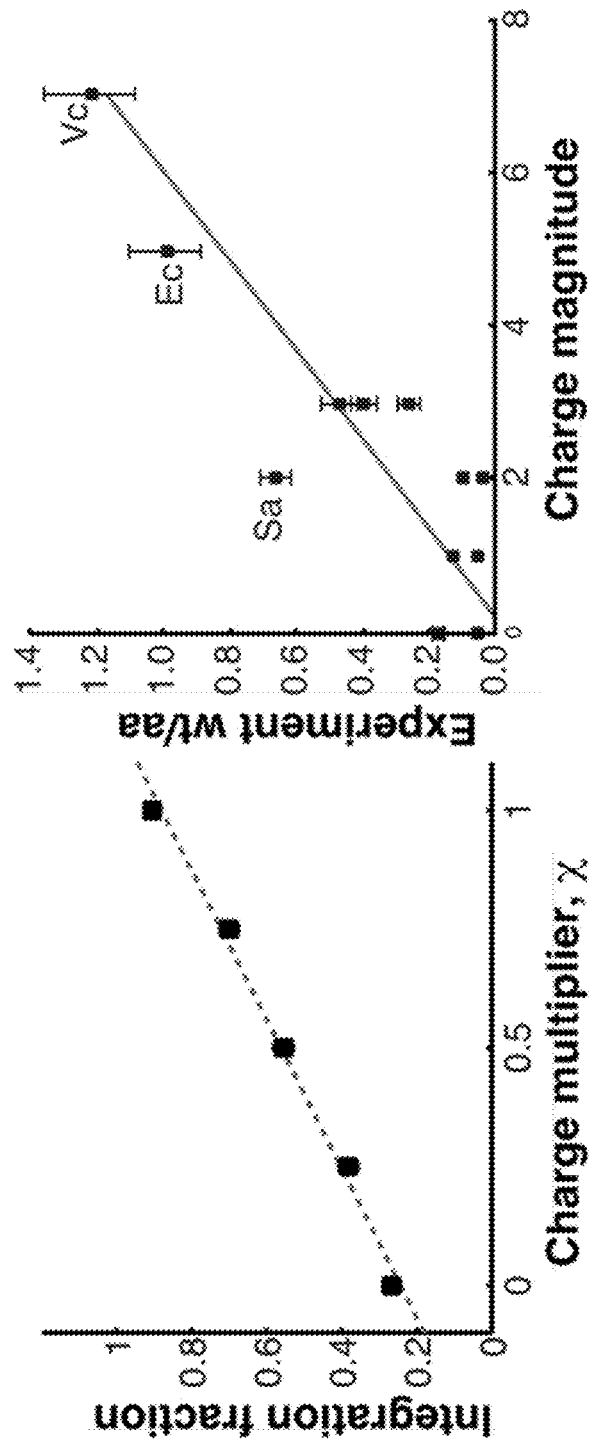
FIG. 17A shows a chart illustrating the fraction of Mt(Aa-tail) simulation trajectories that yield the correct membrane topology, as a function of scaling the C-tail charged residues. The results are normalized with respect to the value for the sequence without any change in C-terminal charge. The values are fit by linear regression with a correlation (R) of 0.98.
FIG. 17B shows a chart illustrating the correlation of the ratio of expression from the wild type relative to that with the Aa C-tail versus the charge magnitude of each homolog (see FIG. 18C below). The values are fit by linear regression with a correlation (R) of 0.88. Error bars calculated from the standard error of the means.

From the simulation trajectory of the TABF protein expression levels, are determined by assessing the fraction of independent translocon-associated protein trajectories that exhibit the topology in which the protein should express. For example, in the case of TatC and YidC, this is the topology in FIG. 25A. The fraction of trajectories that exhibit this topology after completion of translocon-associated biogenesis is found to be predictive of experimentally observed expression levels, as shown in FIG. 16C. In the same manner the effect of changes in TABF determinants on expression levels can be determined, as shown in FIGS. 17A-B.

In embodiments herein described methods and systems can be used to predict and/or control TABF for a protein expressed in homologous or heterologous systems. A heterologous expression is defined as an expression of a protein from one species in an expression system of another species. A homologous expression is defined as an expression of a protein from one species in an expression system of the same species.

In the present disclosure, a computer-based method is described, which uses a coarse-grained (CG) simulation method that enables simulation of the translocon and its associated macromolecular components on timescales beyond the scope of previously employed methodologies. In particular, according to such method, ribosomal translation and membrane integration of nascent proteins can be simulated.

Reference will now be made to a two-dimensional (2D) embodiment of the computer-based method according to the disclosure.

FIG. 1 illustrates the configurational dynamics of the nascent protein chain, conformational gating in the Sec translocon, and the slow dynamics of ribosomal translation. The method according to the disclosure is used to perform minute-timescale CG trajectories to investigate the role of the Sec translocon in governing both stop-transfer efficiency (i.e., propensity of TM to undergo integration into the cell membrane versus secretion across the membrane) and integral membrane protein topogenesis (i.e., the propensity of TM to undergo membrane integration in the Ncyt/Cexo orientation versus the Nexo/Ccyt orientation). These simulations provide a direct probe of the mechanisms, kinetics, and regulation of Sec-facilitated protein translocation and membrane integration. Analysis of the full ensemble of non-equilibrium CG trajectories reveals the molecular basis for experimentally observed trends in integral membrane protein topogenesis and TM stop-transfer efficiency. It demonstrates the role of competing kinetic pathways and slow conformational dynamics in Sec-facilitated protein targeting; and it provides experimentally testable predictions regarding the long-timescale dynamics of the Sec translocon.

A "kinetic pathway" is a notion that can be used to analyze ensembles or sets of simulated trajectories. Suppose that the space associated with all possible configurations/positions for the nascent protein is divided into a collection of subspaces (which can be called "macrostates"). Then, any given trajectory will pass through a series of these macrostates. This series of macrostates followed by the trajectory is the "kinetic pathway" that the trajectory has followed. Depending on how the macrostates are chosen, the different information about the trajectories will be extracted from analyzing the kinetic pathways, such as whether the protein underwent a flipping transition, or whether it first passed into the membrane interior before undergoing secretion across the membrane.

As shown in FIG. 1, the ribosome (100) is shown in complex with the Sec translocon (101) and the lateral gate helix (102). The simulation method projects the protein nascent chain dynamics onto the plane (104) that intersects the translocon channel axis and that bisects the lateral gate (LG) helices (102). The simulation method includes beads for the translocon (101), lateral gate helix (102), the ribosome (100), and the protein nascent chain. The LG helices are shown in (102), the ribosome exit channel is shown at (108), and the lipid membrane is shown at (105). The nascent chain is composed of beads for the signal peptide (106, 110) and the mature domain (107).

A simplification employed in some embodiments of the simulation method is the projection of the nascent protein dynamics onto the plane that passes along the translocon channel axis and between the helices of the LG as shown in FIG. 1. The method can include explicit opening and closing of the translocon LG (see also FIG. 28), which corresponds to the LG helices passing into and out of the plane of the nascent protein dynamics, but the nascent protein is itself confined to the planar subspace.

Coarse-grained representations reduce the cost of calculations and assist in making tractable the minute-timescale trajectories for protein translocation and membrane integration.

Parameterization of the simulation method utilizes molecular dynamics (MD) simulations and transferable experimental data. Free energy calculations and direct MD simulations determine the energetics and timescales of LG opening, including the dependence of the LG energetics on the nascent-protein amino acid sequence; microsecond-timescale all-atom simulations and experimental measurements determine the diffusive timescale for the CG representation of the nascent protein. Experimental amino acid water/membrane transfer free energies determine the solvation energetics of the CG nascent protein residues.

The method employed in accordance with the embodiments of the present disclosure is also described in the paper *Long-Timescale Dynamics and Regulation of Sec-Facilitated Protein Translocation*, B. Zhang and T. F. Miller, Cell Reports 2, 927-937 and S1-S24, Oct. 25 2012, which paper is incorporated herein by reference in its entirety.

The person skilled in the art will understand that the method employed in accordance with the embodiments of the present disclosure has some limitations. In addition to enforcing planar constraints on the motion of the nascent protein, the method provides a coarsened representation for nascent-protein, translocon, and membrane bilayer that includes only simple aspects of electrostatic and hydrophobic driving forces. Potentially important details of residue specific interactions are thus neglected. Backbone interactions along the nascent protein chain are also neglected, such that effects due to the onset of nascent protein secondary structure are ignored, and effects due to translocon conformational changes other than LG motion are not explicitly included. Moreover, the possible roles of membrane-bound chaperones or oligomerization of the translocon channel are not considered. In principle, the simulation method can be modified to incorporate greater accuracy and detail, as well as additional complexity and computational expense. The embodiment described in detail below provides a minimalist description of Sec-facilitated protein translocation and membrane integration.

The protein nascent chain is represented as a freely jointed chain of particles or beads, where each bead represents, according to a specific embodiment of the disclosure, 3 amino acids and has a diameter of 8 Å, the typical Kuhn length for polypeptide chains (Hanke et al., 2010) (4) (Staple et al., 2008) (5). A similar representation is used to describe the Sec translocon, the hydrophobic membrane interior and confinement effects due to the translating ribosome.

The beads are constrained to the plane that lies normal to the lipid bilayer membrane and that bisects the translocon channel interior and the LG helices. CG beads corresponding to the residues of the translating nascent chain evolve subject to overdamped Brownian dynamics, whereas beads representing the Sec translocon (101, 102) and the docked ribosome (100) are fixed with respect to the membrane bilayer. To explicitly incorporate the conformational gating of the translocon LG helices, beads representing the LG helices (102) undergo stochastic transitions between closed-state interactions, which occlude the passage of the nascent chain from the Sec channel to the membrane interior, and open-state interactions, for which the steric barrier to membrane integration is removed. Structural features of the channel and ribosomal confinement are obtained from crystallographic and electron microscopy studies. Exemplary positions for the translocon and ribosome beads are shown in the table of FIG. 19.

Figure 28:
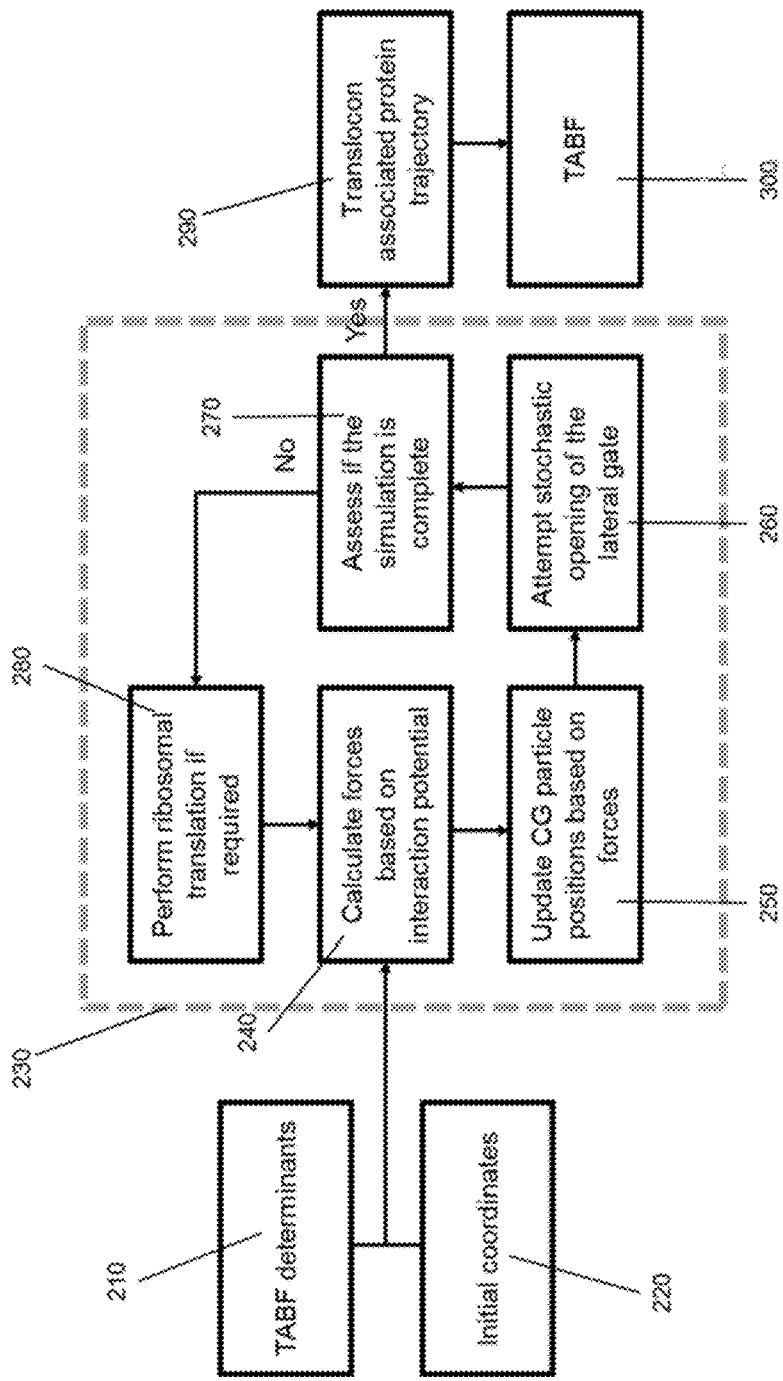

A general mode of operation of the computer-based method of the present disclosure is shown in the diagram of FIG. 28.

In particular, a set of TABF determinants (210) and initial coordinates (220) are input to the computerized system (230) according to the disclosure. Forces of the CG particles (beads) are calculated (240) based on interaction potentials. By way of example, bond interactions, non-bonded interactions, electrostatic interactions and solvation energies are calculated. The protein CG particle positions based on the forces as calculated in (240) are then updated (250), and any stochastic transitions between states of the CG beads (e.g., opening and closing of the lateral gate) are performed, thus providing a trajectory as a function of time. The coordinates of the entire system at any point in time along a trajectory are represented by a matrix of numbers that specify the spatial positions and the state (i.e., LG open or closed) of each CG bead. A full trajectory is thus represented as a time-ordered series of these matrices of numbers. By way of example, such time evolution of the protein can be simulated using Brownian dynamics.

The system can further simulate lateral gate opening corresponding to an opening appearing between the translocon interior and the membrane interior through a stochastic simulation (260). A determination is then made (270) if the simulated protein trajectory is complete. By way of example, the protein trajectory is completed i) following completion of translation/insertion of the full protein sequence (i.e. when the C-terminus of the protein is released from the protein inserter (e.g. the ribosome) at the end of insertion) or ii) prior to completion of translation/insertion of the full protein sequence (i.e. when the C-terminus of the nascent protein is still attached to the protein inserter.

If the simulation is not complete (NO output of step 270), ribosomal translation is performed if required (280), and steps (240-270) are performed again. Once the simulation is complete (YES output of step 270), the translocon associated protein trajectory is generated (290), either by way of graphical representation or as a set of spatial representations as a function of time.

A TABF (300) is determined from the protein trajectory (290). In particular, TABF (300) is determined from the final configuration of the protein (i.e. the spatial distribution of the CG particles) at the end of the simulated trajectory. From this final configuration of the protein, the following can be determined:

(1) The partitioning between protein integration and protein secretion, i.e. whether any given segment of the protein was "secreted" (i.e. passed across the membrane to the lumenal side), was "retained" (i.e. remains on the cytosolic side of the membrane), or was "integrated" (i.e. occupies the spatial region of the membrane).

(2) The topology of the protein, i.e. whether any integrated segment of the protein exhibits (a) a "Type II topology" in which its N-terminal end is in the cytosolic side of the membrane and its C-terminal end is in the lumenal side of the membrane, (b) a "Type III topology" in which its C-terminal end is in the cytosolic side of the membrane and its N-terminal end is in the lumenal side of the membrane, or (c) alternative topologies in which both the N-terminal and C-terminal ends of the segment are on the same side of the membrane.

(3) The expression level of the protein, i.e. the percentage of a given protein to get successfully expressed. In particular, the amount of successful protein expression corresponds to the fraction of simulated trajectories for a given protein that lead to final configurations in which the protein exhibits a "desired" topology, i.e. whether the membrane-integrated segments of the protein traverse the membrane with the intended combination of Type II vs. Type III topologies. Incidentally, the criteria for reaching the desired topology can be applied to all or any subset of the integrated segments. For example, one might require that all of the membrane-spanning protein segments match specified topologies in order for the configuration to qualify as having the desired topology. Alternatively, one might only require that one or a subset of the membrane-spanning segments match specified topologies.

Reference will now be made to some specific embodiments of the methods for evaluating the CG particle potentials, the CG particle time evolution, the lateral gate helices time evolution and the ribosomal translation.

1. CG Particle Interaction Potentials

It should be noted that for each type of interaction potential described there are alternative descriptions possible, as will be apparent to a skilled person. The equations provide a specific example of an embodiment of the claimed simulation method.

CG particles that share a covalent bond are connected using a finite extension nonlinear elastic (FENE) potential (Kremer and Grest 1990) (6);

$$U_{FENE}(r) = -\frac{1}{2}\kappa R_0^2 \ln\left(1 - \frac{r^2}{R_0^2}\right),\qquad\text{[Equation 1]}$$

where $\kappa=7\varepsilon/\sigma^2$, $R_0=2\sigma$ and $\varepsilon=0.833k_BT$. The parameters should be adjusted depending on the extend to which the nascent chain is coarse grained, the parameters provided here are suitable for CG particles representing 3-4 amino acids. $R_0$ corresponds to the maximum length the covalent bond can reach, and $\kappa$ is a force constant.

In general, covalent linkages between atoms or amino-acid residues would correspond to additional linkages between the corresponding CG beads. Additionally, the person skilled in the art will understand that the use of a FENE potential is one example of a potential, which could also include a harmonic potential, quartic potential, Morse potential, rigid-linkages, or many other functional forms that prescribe some energetic penalties upon deviation from particular inter-bead distances.

Short-range, pairwise, non-bonded interactions between pairs of CG particles are described by the Lennard-Jones potential, $$U_{LJ}(r) = \begin{cases} 4\varepsilon\left[\left(\frac{\sigma}{r}\right)^{12} - \left(\frac{\sigma}{r}\right)^{6}\right] + \varepsilon_{cr}, & r_{cl} > r \geq r_{cr} \\ 0, & \text{otherwise,} \end{cases}\qquad\text{[Equation 2]}$$

with $\varepsilon_{cr}$ the value of the Lennard-Jones potential at the right cut-off radius, $r_{cr}$. Values for $\varepsilon$, $r_{cl}$, and $r_{cr}$ depend on the particles involved in the interaction (FIG. 20). For the nonbonding interactions among the beads of the protein nascent chain and between beads of the nascent chain and the ribosome, the LJ parameters correspond to soft-walled, excluded volume interactions (Weeks et al., 1971) (7). Weak attractive interactions account for the affinity of the protein nascent chain for the LG helices of the translocon, as has been observed in crosslinking experiments (Plath et al., 1998) (8). For the open state of the LG, repulsions between the LG and protein nascent chain beads are truncated to allow the peptide to laterally exit the translocon channel. New CG particle types introduced into the simulation method can have any user specified parameter values for the interaction with each other type of CG particle.

Electrostatic interactions are simulated using the Debye-Hückel potential, $$U_{DH}(r) = \frac{\sigma q_i q_j k_B T}{r}\exp\left[-\frac{r}{k}\right],\qquad\text{[Equation 3]}$$

where the Debye length $\kappa=1.4\sigma$, and $q_i$ is the charge of bead i. The Debye length can be modified depending on the electrostatic screening in the simulated system, i.e. changes in the salt concentration, a value of $\kappa=1.4\sigma$ corresponds to electrostatic screening under physiological conditions. When a pair of CG particles does not have strong repulsion, as occurs between the nascent protein and the lateral gate when the lateral gate helices are in the open configuration, the Debye-Hückel potential is capped from bellow to avoid the singularity that would otherwise occur, such that $$U(r) = \begin{cases} U_{DH}(r), & r > \sigma \\ U_{DH}(\sigma), & \text{otherwise} \end{cases}\qquad\text{[Equation 4]}$$

Also in this case, that electrostatic interactions and nonbonding interactions need not only be described using Debye-Huckel or Lennard-Jones potentials. A great variety of other pairwise potentials that incorporates the associated energy scales and lengthscales could also be employed.

Solvation energetics for each CG bead are described using the position-dependent potential energy function $$U_{solv}(x,y) = gS(x;\phi_x,\psi_x)[1-S(y;\phi_y,\psi_y)],\qquad\text{[Equation 5]}$$

$$S(x;\phi_x,\psi_x) = \frac{1}{4}\left(1 + \tanh\frac{x-\phi_x}{b}\right)\left(1 - \tanh\frac{x-\psi_x}{b}\right)\qquad\text{[Equation 6]}$$

where g is the water-lipid transfer free energy of the CG bead, $b=0.25\sigma$ is the switching lengthscale and $\phi$ and $\psi$ indicate the borders of the membrane region. All beads feel a membrane potential with $\phi_x=-2.0\sigma$, $\psi_x=2.0\sigma$, $\phi_y=-1.5\sigma$ and, $\psi_y=1.5\sigma$, hydrophilic beads feel an additional core-membrane potential with $\phi_x=-1.0\sigma$, $\psi_x=1.0\sigma$, $\phi_y=-2.5\sigma$ and, $\psi_y=2.5\sigma$. Additional position dependent potentials acting on specific beads can be implemented, as was done in specific cases presented here, where there are additional position dependent potentials they are described.

2. CG Particle Time Evolution

In the specific examples the time evolution of the nascent chain is simulated using overdamped Brownian dynamics with a first order Euler integrator (Stoer and Bulirsch, 2002) (9), $$x_i(t + \Delta t) = x_i(t) - \beta D\frac{\partial U(x(t))}{\partial x_i}\Delta t + \sqrt{2D\Delta t}\,\eta_i\qquad\text{[Equation 7]}$$

where $x_i(t)$ is a single Cartesian degree of freedom for nascent chain bead i at time t, $U(x(t))$ is the potential energy function for the full system, $\beta=1/k_BT$, D is the diffusion coefficient, and $\eta$ is a random number drawn from a Gaussian distribution with zero mean and unit variance. In the specific embodiments of the method described herein $D=768.0$ nm²/σ, this value of the diffusion coefficient agrees with atomistic simulations, and available experimental data, but the simulation method is robust to variations in this parameter. In the 2-dimensional embodiment of the method each nascent chain CG particle is time-evolved in 2-dimensions, while in the 3-dimensional embodiment of the method each nascent chain particle is time-evolved in 3-dimensions. Although the example described in the present paragraph was found suitable for obtaining translocon-associated protein trajectories, the person skilled in the art will understand that a different description of the dynamics is possible.

3. Lateral Gate Helices Time Evolution

Conformational gating of the translocon lateral gate helices corresponds to the lateral gate helices moving out of the plane of confinement for the CG beads in the 2-dimensional embodiment of the simulation method, allowing the nascent chain to pass into the membrane bilayer. In the 3-dimensional embodiment of the simulation method lateral gate opening corresponds to an opening appearing between the translocon interior and the membrane interior. The rate of stochastic LG opening and closing is dependent on the sequence of the nascent protein CG particles that occupy the translocon channel;

$$k_{open} = \frac{1}{\tau_{LG}} \frac{\exp(-\beta \Delta G_{tot})}{1 + \exp(-\beta \Delta G_{tot})}, \quad \text{[Equation 8]}$$

and, $$k_{close} = \frac{1}{\tau_{LG}} \frac{1}{1 + \exp(-\beta \Delta G_{tot})} \quad \text{[Equation 9]}$$

where the timescale for lateral gate opening and closing events, $\tau_{LG}=500$ ns, and $\Delta G_{tot}$ is the free energy cost associated with LG opening. The free energy cost for LG opening is given by $$\Delta G_{tot} = \Delta E + \sum_{i=1} \Delta G_{TF} + \Delta G_{empty} \chi_{empty}, \quad \text{[Equation 10]}$$

where $\Delta E$ is the difference in interaction energy between the nascent chain beads and the translocon in the open conformation compared to the interaction between the nascent chain beads and the translocon in the closed conformation, $\Delta G_{TF}$ is the water-lipid transfer free energy for nascent chain beads inside the channel, $\Delta G_{empty}=16\varepsilon$ is the free energy cost for opening the LG in the empty channel, and $\chi_{empty}$ is the fraction of the channel that does not contain nascent chain particles. The value for $\Delta G_{empty}$ depends on the translocon that is included in the simulation system; a value of 16E was used here to simulate the translocon for *E. coli* and *S. cerevisiae*. It should be noted that other more general hydrophobic-hydrophilic transfer free energies can be taken into account, where $\Delta G_{TF}$ represents a contribution to the free energy of the LG opening that depends on the position and attributes of the CG beads, such as charge, hydrophobicity and size. Additionally, it should also be noted that while in some embodiments the sum in the above equation is extended over only the CG beads within the channel, other embodiments can take into account contributions of CG beads at other positions as well.

4. Ribosomal Translation

Where applicable, ribosomal translation can be simulated by adding bead to the nascent chain sequentially starting from the N-terminal end of the nascent chain amino acid sequence and continuing to the C-terminal end of the nascent chain amino acid sequence. Translation can be stalled at any point along the nascent chain sequence, or can be continued until the entire nascent chain sequence has been translated, at which point the nascent chain is released from the ribosome. After release the ribosome can be kept present, or can be allowed to dissociate. Dissociation of the ribosome is modeled by removing interactions between the nascent chain CG particles and the CG particles describing the ribosome. Beads that have yet to be translated are not time evolved, and are not interacting with other beads in the system. Various rates of translation have been tested using the simulation method, in a range from 6 res/s to 24 res/s, the rate of translation is system dependent, and can be chosen to be distinct for each CG bead type.

Dissociation of the protein-inserter can be modeled by eliminating interactions associated with the protein-inserter CG beads. In the embodiment of the method where the ribosome is utilized as protein-inserter, ribosomal translation proceeds at a pace of approximately 10-20 amino acid residues per second (res/s) (Bilgin et al., 1992) (10) (Boehlke and Friesen, 1975) (11), although this rate can be reduced approximately 4-fold upon addition of cycloheximide (Abou Elela and Nazar, 1997) (12) (Goden and Spiess, 2003) (13). Exemplary ribosomal translation rates in the range of 6-24 res/s (2-8 beads/s) have been considered in the embodiments of the present disclosure. Other protein-inserters and different translation rates can be simulated using the same embodiment of the method by introducing minimal changes in the parameters of the method, as will be understood by a skilled person.

The binding immunoglobulin protein (BiP) is an essential component of the eukaryotic Sec translocon (Brodsky et al., 1995) (14). However, explicit inclusion of BiP binding within the simulation method gives rise to only modest effects in the calculated results for protein translation and membrane integration. Unless otherwise stated, explicit BiP binding has not been included in the simulations performed by the inventors.

Figure 24:
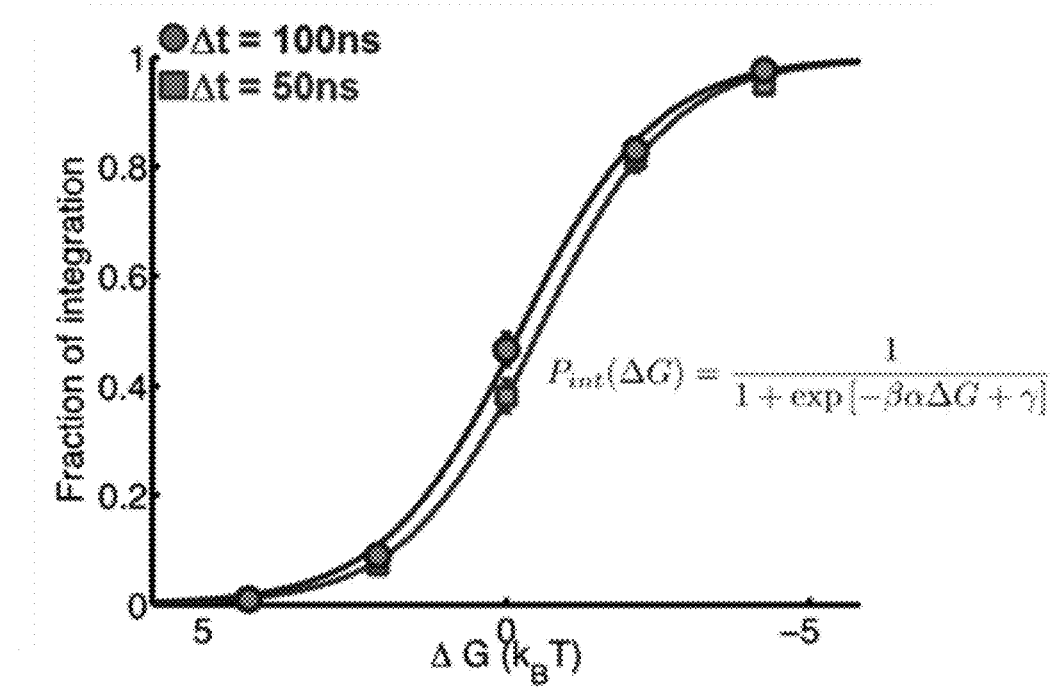
FIG. 24 shows an example application of the 3-dimensional embodiment of the simulation method. The TABF determinant that has been modified is the water-lipid transfer free energy of 9 subsequent amino acids in a 240 amino acid polypeptide sequence. Changing this TABF determinant affects the TABF as determined by analysis of the trajectory. Lower values of the water-lipid transfer free energy lead to an increase integration, while higher values of the water-lipid transfer free energy lead to an increase of secretion. Also shown is that the TABF as determined by the simulation method is robust with respect to changes in the simulation time step parameter.

The simulation methods described herein can be utilized for simulations in 2-dimensions, or in 3-dimensions. Time evolution of the nascent chain, interactions between CG particles, and dynamics of the lateral gate helices are not affected by changes in the dimensionality of the method. The coordinates of the protein inserter and the translocon are altered in order to describe the appropriate geometry in 3-dimensions. Reference can be made, for example, to FIGS. 23A, 23B and 24, which show applications of a 3-dimensional embodiment.

Particles in the simulation methods can represent single atoms, with the corresponding atomistic interaction potentials, or multiple atoms, with corresponding CG interaction potentials as described herein.

In particular, for implementations of the simulation method in which each CG bead corresponds to one or more amino acid residues, then the primary sequence of the nascent protein is reflected in the connectivity of the CG beads into a linear chain. For implementations in which the CG beads correspond to collections of atoms that are smaller than a single amino acid (such as individual atoms, or such as backbone moieties and side-chain moieties), then a branched connectivity of the chain of CG beads can be employed.

The connectivity of the CG beads should reflect the connectivity of the covalent bonds in the underlying protein sequence. For example, for the case in which the CG beads correspond to either backbone or side-chain moieties of the nascent protein, then the nascent protein should be represented in terms of a linear chain of CG beads associated with the backbone residues and with each backbone moiety connected to an additional CG bead that is associated with the corresponding side-chain moiety. As another example, for the case in which the CG beads correspond to individual atoms, then the nascent protein should be represented in terms of a chain of CG beads with linkages that correspond to the connectivity the covalent bonds in the physical protein.

Based on the teachings of the present disclosure, the person skilled in the art can also envision versions of the simulation method in which some segments of the nascent protein are modeled at a more coarsened level (with multiple amino-acid residues per CG bead, for example) whereas other segments of the nascent protein are modeled at a less coarsened level (with only a single amino-acid residue per CG bead, for example).

Some embodiments of the present disclosure can describe implementations for which the constituents of the solvent and membrane environments are represented as spatial fields (as in Equations 5 and 6), as opposed to representing those constituents in terms of CG beads. However, the person skilled in the art will understand that this need not be the case. In particular, the simulation method can be implemented using CG beads so that the constituents of the spatial regions corresponding to "protein-inserter side" and the "trans-protein-inserter side" of the membrane are described in terms of CG beads (e.g., a CG bead for each water molecule or a set of water molecules, a CG bead for each solvated ion or a solvated ion and a set of water molecules, or one CG bead for each atom, thus providing full resolution at the atomic scale). Similarly, further embodiments of the present disclosure can use CG beads to describe the constituents of the spatial regions corresponding to the membrane (e.g., a CG bead for each lipid molecule and each other membrane constituent (such as cholesterol molecules), a CG bead for the head-group of each lipid molecule and other CG beads for all or part of the tail-groups of the lipid molecules, or one CG bead for each atom, thus providing full resolution at the atomic scale).

Additionally, embodiments are provided in the present disclosure where the translocon and the protein inserter (such as the ribosome) are described in terms of CG beads that represent groups of amino-acid residues or groups of nucleic-acid residues (while the description of BiP and other lumenal factors is even more coarse in nature). However, as above, finer-resolution implementations of the simulation method could be straightforwardly employed, by having the CG beads for the translocon and ribosome correspond to smaller groups of atoms, including (i) individual amino-acid residues or nucleic-acid groups, (ii) groups of atoms that correspond to subsets of the amino-acid or the nucleic acids, or (iii) individual atoms in the translocon, protein inserter, and the other co-factors. As above, the connectivity of the CG beads would reflect the connectivity of the atoms in the associated physical biomolecules.

Each simulation yields a simulation trajectory with coordinates of the simulated system. The coordinates fully specify the resulting TABF. Multiple independent trajectories can be simulated for the simulated system an ensemble of initial conditions to provide statistical distributions of the possible resulting TABF of the simulated system. Lumenal co-factors (such as BiP) can be explicitly included in the simulation methods and their effect on TABF can be assessed by analysis of the resulting trajectories.

The simulation method described in the above paragraphs enables simulation of the translocon and its associated molecular components on timescales beyond the scope of previously employed methodologies. The simulation method explicitly describes the configurational dynamics of the nascent protein chain, conformational gating in the Sec translocon, and the slow dynamics of ribosomal translation.

In accordance with the present disclosure, such method can be used to perform minute-timescale CG trajectories to investigate the role of the Sec translocon in governing both stop-transfer efficiency (i.e. propensity of transmembrane domains (TMD [TODO: change throughout]) to undergo integration into the cell membrane versus secretion across the membrane) and integral membrane protein topogenesis (i.e. the propensity of TMD to undergo membrane integration in the ($N_{cyt}/C_{exo}$) orientation versus the ($N_{exo}/C_{cyt}$) orientation).

Computer-based simulations performed with the computerized method according to the present disclosure can provide a direct probe of the mechanisms, kinetics and regulation of Sec-facilitated protein translocation and membrane integration. In particular, analysis of the full ensemble of nonequilibrium CG trajectories reveals the molecular basis for experimentally observed trends in integral membrane protein topogenesis and TMD stop-transfer efficiency; it demonstrates the role of competing kinetic pathways and slow conformational dynamics in Sec-facilitated protein targeting; and it provides experimentally testable predictions regarding the long-timescale dynamics of the Sec translocon.

5. Direct Simulation of Cotranslational Protein Integration

Signal peptide (SP) orientation is a determining factor in integral membrane protein topogenesis. The orientation of N-terminal signals helps to establish the topology of multidomain integral membrane proteins and to dictate whether N-terminal or C-terminal domains undergo translocation across the membrane. Biochemical studies have established the dependence of SP orientation upon a range of factors, including SP flanking charges, SP hydrophobicity, protein mature domain length (MDL), and the ribosomal translation rate. In accordance with the present disclosure, the simulation method described above is employed to directly simulate co-translational protein integration and to determine the molecular mechanisms that give rise to these experimentally observed relations.

Figure 2:
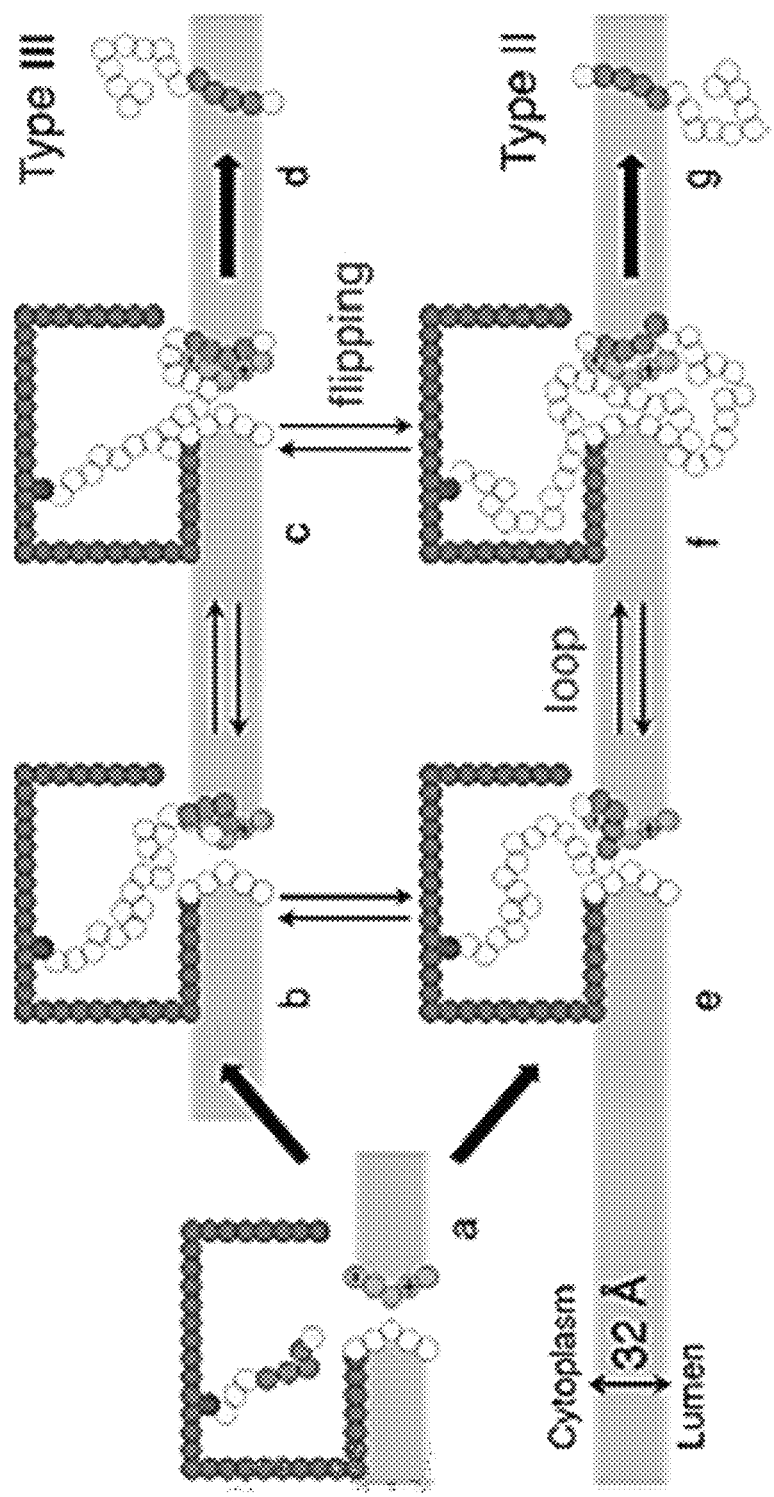
FIG. 2 shows a schematic illustrating kinetic pathways for Type II and Type III Membrane Integration of Signal Anchor Proteins Obtained from Direct CG Simulations. Ribosome and translocon are as in FIG. 1, and the nascent chain consists of a TMD (shaded grey) and two hydrophilic loops flanking the TMD (white). States a-g observed in the mechanism are described in the text.

In particular, the process in which co-translational integration of a signal anchor protein yields either the type II ($N_{cyt}/C_{exo}$) or type III ($N_{exo}/C_{cyt}$) orientation of the uncleaved SP domain is considered. FIG. 2 illustrates the simulation protocol, with the N-terminal SP domain shown in dark and and light colors.

Integration of proteins that vary with respect to both SP sequence and MDL is considered. Three different kinds of SP are being considered: an SP composed of a canonical sequence of CG beads ($RL_4E$), an SP composed of a sequence in which the positive charge on the N-terminal group is eliminated ($QL_4E$), or an SP composed of a sequence with enhanced SP hydrophobicity ($RL_6E$).

To model the hydropathy profile of the engineered protein H1ΔLeu22H1ΔLeu22, proteins that include a hydrophilic mature domain with a hydrophobic patch near the SP are being considered. Specifically, the protein mature domain is modeled using the $Q_5LQ_n$ sequence of CG beads, such that the total peptide length ranges from 30 to 80 beads (90-240 residues [res]). The sensitivity of protein topology to hydrophobic patches on the mature domain is exemplified in FIG. 4A, later described.

CG trajectories of the above described method are continued until the protein nascent chain reaches either type II or type III integration. Depending upon the rate of ribosomal translation and the MDL, each CG trajectory thus ranges from 2 to 20 s of simulation time; the corresponding CPU time required to perform each trajectory is approximately 0.2-10 hrs. Each data point in FIGS. 3A-3C is obtained by averaging the results of at least 600 independent CG trajectories.

FIGS. 3A-3C show the fraction of peptides that are calculated to undergo type II integration as a function of protein MDL. In each case, the panels show that the simulation method predicts a strong dependence of SP topology on the length of the protein mature domain, with a fast rise in the type II integration fraction at short lengths plateauing to a fixed value at longer MDL. The simulation method also finds significant dependence of signal topology on the SP charge distribution (FIG. 3A), SP hydrophobicity (FIG. 3B), and ribosomal translation rate (FIG. 3C). Each of these trends is in striking agreement with known findings. In addition to the crossover from strong to weak dependence of the signal topology with increasing MDL, the experimental study likewise reports type II integration to be reduced with the removal of positively charged N-terminal groups, more hydrophobic SP sequences, and faster protein insertion.

FIGS. 4A-4F provide additional tests and comparisons of the simulation method against protein topogenesis experiments, analyzing factors that include negative N-terminal charges, elongated N-terminal domains, charge mutations on the translocon, and charged patches on the nascent-protein mature domain. In the following paragraphs, the CG computerized simulations will be used to enable the detailed analysis of the insertion dynamics and to determine the mechanistic origin of these various trends.

6. Competition between Kinetic Pathways Governs Topogenesis

Inspection of the ensemble of CG trajectories reveals multiple kinetic pathways by which the protein nascent chain achieves type II or type III integration (FIG. 2). During early-stage protein insertion, the SP typically binds at the lateral gate (LG) in one of two conformations, either with its N terminus buried inside the translocon (state b of FIG. 2) or exposed to the membrane (state e of FIG. 2). Similar conformations have been observed in microsecond-timescale, all-atom MD simulations of early-stage peptide insertion. From state e, further insertion of the nascent chain yields state f, in which the SP assumes the $N_{cyt}/C_{exo}$ orientation. Continued translocation of the mature domain in this orientation eventually leads to type II integration. From state b, further insertion leads to state c, in which the SP assumes the $N_{cyt}/C_{exo}$ orientation. This orientation does not directly facilitate mature domain translocation, without which the protein assumes type III integration. Slow transitions between states c and f are also observed in many trajectories; this conformational change, in which the SP "flips" between type III and type II integration topologies, is found to lie at the heart of many of the trends in FIGS. 3A-3C.

To analyze the flow of trajectories among these competing mechanisms, the CG trajectories are categorized according to the chronology with which they pass through the states a-g in FIG. 2. Through such analysis, it has been found by the inventors that each trajectory is associated with either type III mechanism (a-b-c-d), the type II loop mechanism (a-e-f-g), or the type II flipping mechanism (a-b-c-f-g). It should be emphasized that trajectories need not pass irreversibly through these states. Trajectories that visit state c prior to type II integration are associated with the flipping mechanism, whereas any other trajectory that reaches type II integration is associated with the loop mechanism. All remaining trajectories are associated with the type III mechanism. The definition for state c in terms of the coordinates of the model is later described in the text of the present disclosure.

Figure 3D:
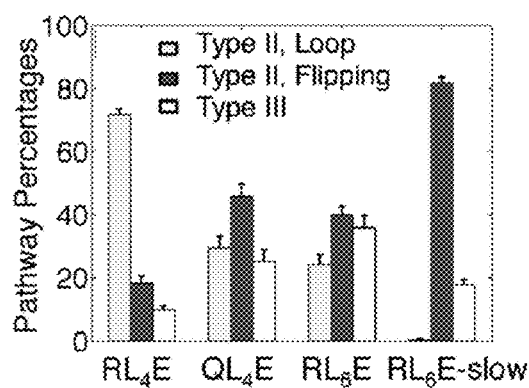

FIG. 3D presents the fraction of trajectories passing through each of these competing mechanisms, and it compares the effect of SP sequence and translation rate on the mechanism of integration. A total exemplary protein nascent chain length of 210 residues is considered for all cases in such figure.

Differences between the $RL_4E$ and $QL_4E$ data sets in FIG. 3D help to explain the shift between the two corresponding data sets in FIG. 3A. For the canonical SP sequence ($RL_4E$), FIG. 3D shows that CG trajectories predominantly follow the type II loop mechanism for integration. However, upon mutating the SP sequence with respect to the number of charged residues ($QL_4E$), the type II flipping mechanism and the type III mechanism become more prevalent. Removal of the N-terminal charge group diminishes the electrostatic stabilization of the SP in the $N_{cyt}/C_{exo}$ orientation. The CG trajectories are thus less likely to visit states e and f, which are on pathway for type II loop integration, in favor of states b and c, which are on pathway for both type II flipping and type III integration. Interestingly, the flipping mechanism allows for significant compensation of the type II integration fraction upon mutation of the charge group. The effect of the SP sequence mutation on the flow of CG trajectories (FIG. 3D) is thus much greater than the corresponding effect on the final branching ratio between type II and type III integration (FIG. 3A). The simulations reveal a competition between electrostatic stabilization and SP reorientation kinetics that contributes to the well-known "positive-inside rule" for integral membrane protein topology. Furthermore, these results suggest that hindering the c→f flipping transition, perhaps via small molecule binding, may lead to a larger effect on the type II integration fraction than is observed with N-terminal charge mutation.

Comparison of the data for the $RL_4E$ and $RL_6E$ sequences in FIG. 3D explains the shift between the two corresponding data sets in FIG. 3A-3F. FIG. 3D shows that increasing the hydrophobicity of the SP reduces the flow of integration trajectories through the type II loop mechanism. As before, this can be attributed to changes in the stability of states along the competing kinetic pathways. Increasing the hydrophobicity of the SP sequence significantly stabilizes SP configurations in state b, which favorably expose the hydrophobic segment to the membrane, instead of configurations in state e, which bury the hydrophobic segment inside the translocon. This effect draws trajectories away from the loop mechanism (FIG. 3D) and leads to decreased type II integration (FIG. 3B).

Differences between the $RL_6E$ and $RL_6E$-slow data sets in FIG. 3D help to explain the shift between the two corresponding data sets in FIG. 3C. Slowing the rate of ribosomal translation in proteins from 24 res/s to 6 res/s causes the CG trajectories to shift almost entirely to a type II flipping mechanism.

These differences are remarkable since they involve no change in the interactions of the system. The shifts in SP topology (FIG. 3C) and integration mechanism (FIG. 3D) with protein translation rate are purely kinetic effects. With slower translation, partially translated protein nascent chains have more time to undergo conformational sampling and are more likely to visit state c; it is therefore expected that panel FIG. 3D shows that type II loop integration decreases in favor of combined type II flipping integration and type III integration. However, the corresponding decrease in type III integration is more surprising.

The decrease in type III integration upon slowing translation arises from the important role of the flipping transition from state c to state f, which enables the nascent chain to reach the more thermodynamically favorable configurations associated with the $N_{cyt}/C_{exo}$ SP orientation.

Figure 3E:
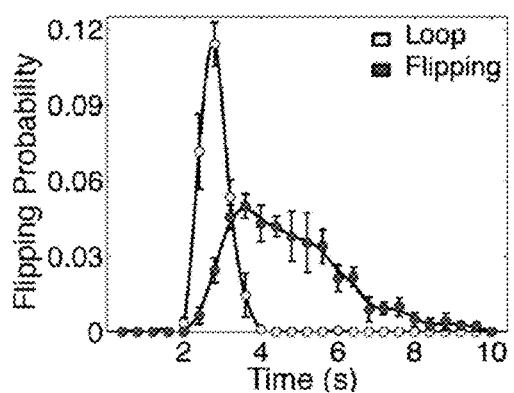

FIG. 3E plots the distribution of arrival times at state f for trajectories that follow either the type II loop mechanism or the type II flipping mechanism. Trajectories complete the loop mechanism relatively quickly, whereas the timescale for flipping persists as long as 10 s. The flipping transition thus introduces a slow timescale for conformational dynamics that couples to the dynamics of ribosomal translation. Slowing ribosomal translation provides more time for the nascent chain to undergo flipping; this purely kinetic effect enhances type II integration in FIG. 3C.

Figure 3F:
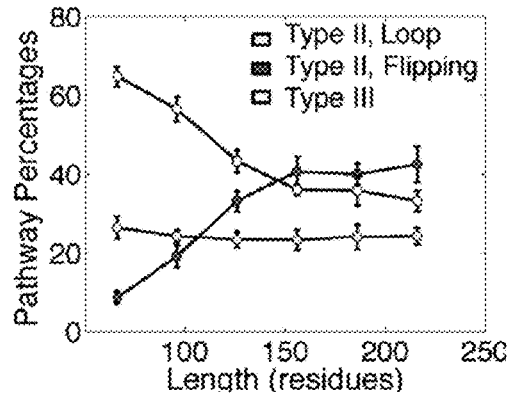

The final trend left to explain in FIGS. 3A-3C is the dependence of the type II integration fraction on the MDL. For every data set, the type II integration fraction increases with MDL before plateauing to a constant value. FIG. 3F elucidates this trend by presenting how the insertion mechanism varies with MDL. The percentage of CG trajectories following each mechanism is calculated as in FIG. 3D.

With increasing MDL (FIG. 3F), the fraction of trajectories following the type II loop mechanism remains relatively unchanged, whereas the prevalence of type II flipping increases at the expense of the type III mechanism. As was seen from FIG. 3E, trajectories commit to the type II loop mechanism relatively early during insertion, prior to the full completion of ribosomal translation; it follows that increasing the MDL will have little effect on the fraction of trajectories following this mechanism. Furthermore, the tradeoff in FIG. 3F between the type II flipping and type III mechanisms occurs for the same reason as was discussed for slowed ribosomal translation. Increasing the MDL in FIG. 3F provides more time for the tethered nascent chain to undergo the slow flipping transition from state c to the thermodynamically favored state f. At long MDL, the crowded environment in the ribosome-translocon junction causes nascent chain configurations in state c to be driven into state d before they can undergo the flipping transition. This causes the fraction of type II flipping trajectories to cease rising in FIG. 3F, such that the relative fraction of type II flipping and type III trajectories approaches a constant value. The results in FIG. 3F correspond to the particular case of the $RL_6E$ SP sequence and the 24 res/s translation rate. However, the trends are general and explain the MDL dependence of the type II integration fraction in FIGS. 3A-3C.

7. Loop Versus Flipping Mechanisms

Observation of competing pathways for type II integration is an unexpected and significant feature of the CG simulations described in the present application. The observed coexistence of the loop and flipping mechanisms in the CG simulations according to embodiments of the present disclosure helps to reconcile experimental findings in prior literature, and it provides a basis for understanding the competing influences of SP hydrophobicity, SP charge distribution, MDL, and ribosomal translation rate in regulating Sec-facilitated type II and type III protein integration.

In assessing the role of the type II flipping mechanism in physiological systems, it is noted that many naturally occurring proteins exhibit longer N-terminal domains and less hydrophobic SP than the protein sequences considered in the present disclosure. Attention is drawn to FIG. 3D, which reveals that decreasing SP hydrophobicity leads to a decrease in the fraction of trajectories undergoing the type II flipping mechanism. Furthermore, CG simulations performed using protein nascent chain sequences with longer N-terminal domains (see FIG. 3C) reveal a corresponding decrease in the fraction of trajectories that exhibit the type II flipping mechanism.

8. Additional Validation and Prediction for Protein Topogenesis

8A. Hydrophobic Patches in the Mature Domain

FIGS. 4A-4B show significant dependence of the CG simulations of protein topogenesis on both the hydrophobicity (FIG. 4A) and the location (FIG. 4B) of hydrophobic patches in the mature domain of the protein nascent chain. The results can be understood from the effect of the hydrophobic patches in the type II flipping pathway for membrane integration, which involves reorientation of the SP from the $N_{exo}/C_{cyt}$ to the opposite topology. The flipping transition is facilitated by the transient opening of the LG, the energetics of which depend on the hydrophobicity of the protein nascent chain beads that occupy the channel interior. The probability of undergoing the flipping transition thus decreases as the hydrophobic patch plays a smaller role in stabilizing the transient opening of the translocon LG, either because the patch is less hydrophobic or because it occupies a more distant region of the mature domain.

It should be emphasized that the SP flipping transition gives rise to a slow timescale in type II membrane integration that leads to characteristic trends in protein topogenesis, and the hydrophobic patches in the mature domain play a significant role in the simulation method of facilitating this flipping transition.

8B—Charged-Residue Mutations on the Translocon

Figure 4D:
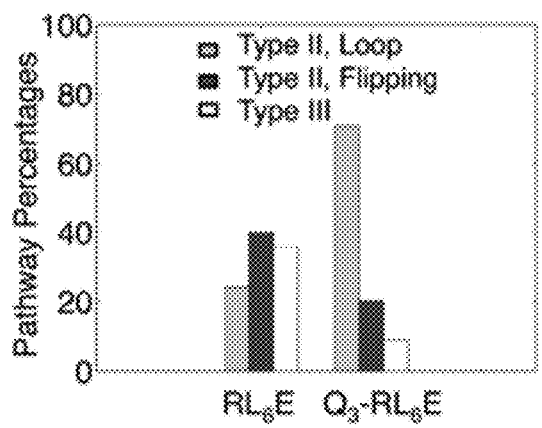
Figure 4E:
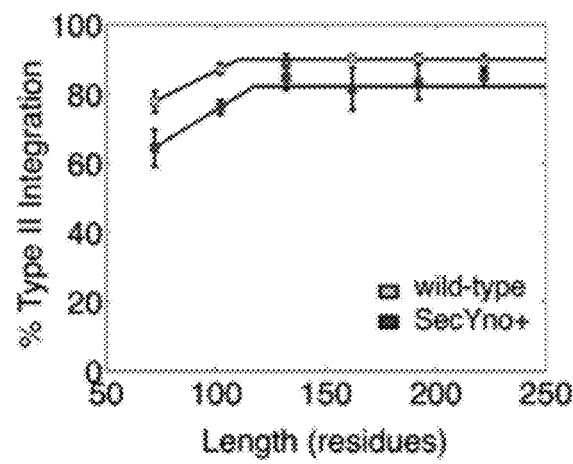

FIG. 4E illustrates that charged residue mutations on the translocon lead to significant changes in integral membrane protein topology. The data set corresponds to the protein topogenesis results presented for the $RL_4E$ SP sequence in FIG. 3A. The data set is obtained using the same protein sequences and removing the positive charge on the lumenal side of the translocon LG (see FIG. 2). The negatively charged CG bead on the cytosolic side of the translocon LG is left unchanged. As is seen in the figure, the charge mutation leads to reduction of type II integration. General features of the nascent-protein length dependence remain unchanged. The plateau value for the type II integration at long MDL is reduced by approximately 10%. These results illustrate the role of charged translocon residues in establishing the "positive-inside rule" for integral membrane protein topogenesis, as it has already been experimentally observed.

8C—Charged-Residue Mutations on the Nascent-Protein Mature Domain (Multispanning Protein Example)

One of the most remarkable recent experimental results on protein topogenesis is that distant C-terminal residues can control the overall topology of a multispanning integral membrane protein. In FIGS. 4G-4I, it is shown that this effect is also captured in the CG model of the present disclosure. The figure presents results from the direct simulation of membrane integration for a multispanning integral membrane protein. Specifically, two different nascent protein sequences are considered, each of which exhibits three hydrophobic TMDs (see FIG. 4G). The distribution of flanking charges for the first two TMDs is identical for the two protein sequences. For Protein 1, the third TMD includes a single positively charged bead at its N-terminal end, whereas for Protein 2, the third TMD includes three positively charged beads at its C-terminal end. In complete detail, the sequence of CG beads for Protein 1 is $RL_4EQ_3L_4RQ_3RL_4Q_{28}$, and the sequence for Protein 2 is $RL_4EQ_3L_4RQ_4L_4R_3Q_{25}$.

Membrane integration of Proteins 1 and 2 is directly simulated using the same membrane topogenesis protocol described above. The CG trajectories are terminated when all of the following criteria are met: (i) ribosomal translation is completed, (ii) all three TMDs span the membrane (see FIG. 4H), and (iii) the first two TMDs at the N-terminal end of the protein have diffused to a distance of 16 nm from the translocon (which is sufficient to ensure that the third TMD has also released from the channel).

FIG. 4I presents the calculated fraction of trajectories that lead to the $N_{cyt}/C_{exo}$ orientation for the two protein sequences. Both protein sequences exhibit a final product that is consistent with the positive-inside rule, despite the fact that this rule is dictated by the third TMD. Consistent with earlier experimental studies, these simulations suggest that overall integral membrane topology can remain undetermined until the final stages of ribosomal translation.

8D—Positive Versus Negative N-Terminal Changes on the Nascent Protein

The results in FIG. 3A emphasize that the simulation method of the present disclosure captures the essential features of the positive-inside rule for protein topogenesis. Specifically, comparison of nascent proteins for which the SP has a positively charged N terminus ($RL_4E$) with those for which the SP has a neutral N terminus ($QL_4E$) indicates that the positive charge leads to a greater fraction of type II integration. This effect is well-established experimentally. A natural question, then, is whether the simulation method also predicts a "negative-outside" bias, for which a negatively charged SP N terminus leads to a greater degree of type III integration. This effect is less clearly established experimentally, with studies both observing and not observing the negative-outside bias on protein topology.

Figure 4F:
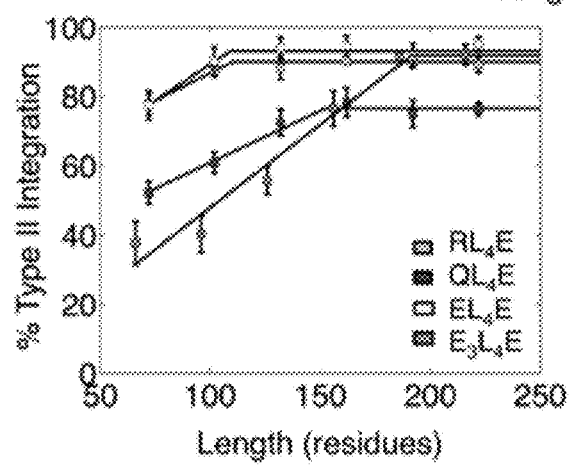
Figure 4G:
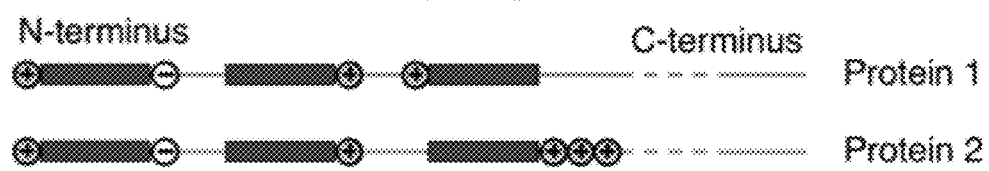
Figure 4H:
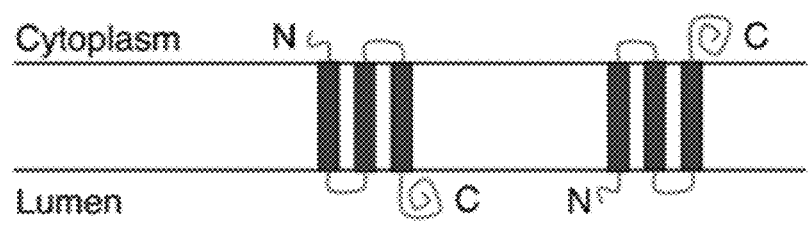
Figure 4I:
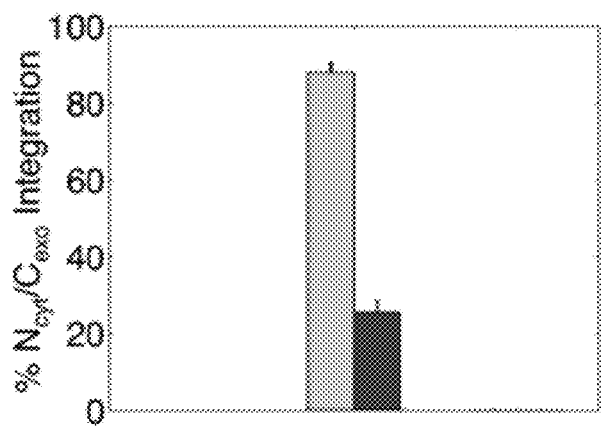

As is seen in panel FIG. 4F, the simulation method also finds mixed results with respect to negative-outside bias. Simulations presented in the figure employ the same protein topogenesis simulation protocol as is used for FIG. 3A. In addition to the results for the SP with an uncharged ($QL_4E$) and a positively charged N terminus ($RL_4E$), results are also included for which the SP exhibits a single negatively charged N-terminal bead ($EL_4E$) or three negatively charged beads ($E_3L_4E$). Remarkably, inclusion of a single negatively charged bead at the SP N terminus ($EL_4E$) is found to have essentially the same effect as a single positively charged bead ($RL_4E$); this result is inconsistent with a negative-outside bias. However, upon inclusion of additional negatively charged beads ($E_3L_4E$), the negative-outside bias is observed for relatively short MDL. The competition of factors associated with negative-outside bias are found to be more complex than those leading to the positive-inside rule, which may help to explain the variation in experimental findings. The inventors further note that detailed molecular interactions of the charged residues with the lipid bilayer, which are greatly simplified in the simulation method, may substantially impact these findings.

9. Regulation of Stop-Transfer Efficiency

In addition to facilitating the translocation of proteins across the phospholipid membrane, the Sec translocon plays a key role in determining whether nascent protein chains become laterally integrated into the membrane. Strong correlations between the hydrophobicity of a TMD and its stop-transfer efficiency have led to the suggestion of an effective two-state partitioning of the TMD between the membrane interior and a more aqueous region. However, models for this process based purely on the thermodynamic partitioning of the TMD do not account for the experimentally observed dependence of stop-transfer efficiency on the length of the protein nascent chain, nor would such models anticipate any change in TMD partitioning upon slowing ribosomal translation. Furthermore, recent theoretical and experimental work point out that the observed correlations between stop-transfer efficiency and substrate hydrophobicity can also be explained in terms of a kinetic competition between the secretion and integration pathways under the substrate-controlled conformational gating of the translocon.

To further elucidate the mechanism of Sec-facilitated regulation of protein translocation and membrane integration, the simulation method according to the present disclosure has been employed to directly simulate cotranslational stop-transfer regulation and to analyze the role of competing kinetic and energetic effects, as detailed in the following paragraphs.

10. Direct Simulation of Co-Translational TMD Partitioning

Figure 5:
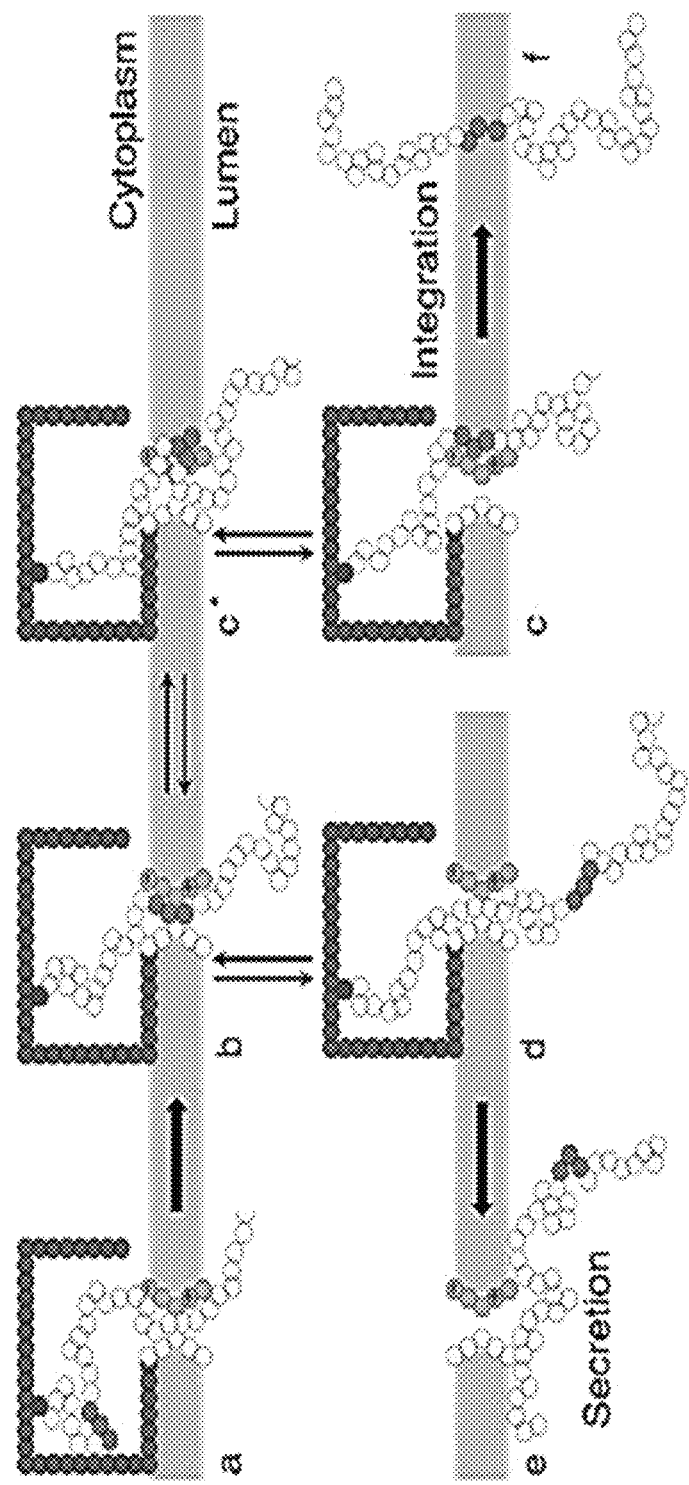
FIG. 5 shows a schematic illustrating kinetic pathways for Cotranslational Protein Translocation and Membrane Integration Obtained from Direct CG Simulations The H-domain of the protein nascent chain is shaded grey. The full N-terminal anchor domain of the protein nascent chain is not shown here; the full system is shown in FIG. 10. States a-f observed in the mechanism are described in the text.

Following recent experimental studies, the cotranslational partitioning of a stop-transfer TMD (i.e., the H-domain) is considered, where the protein nascent chain topology is established by an N-terminal anchor domain. Stop-transfer efficiency is defined as the fraction of translated proteins that undergo H-domain membrane integration, rather than translocation. FIG. 5 illustrates the simulation protocol, with the H-domain shown in dark. See also FIG. 10, which shows the full system including the anchor domain.

Figure 10:
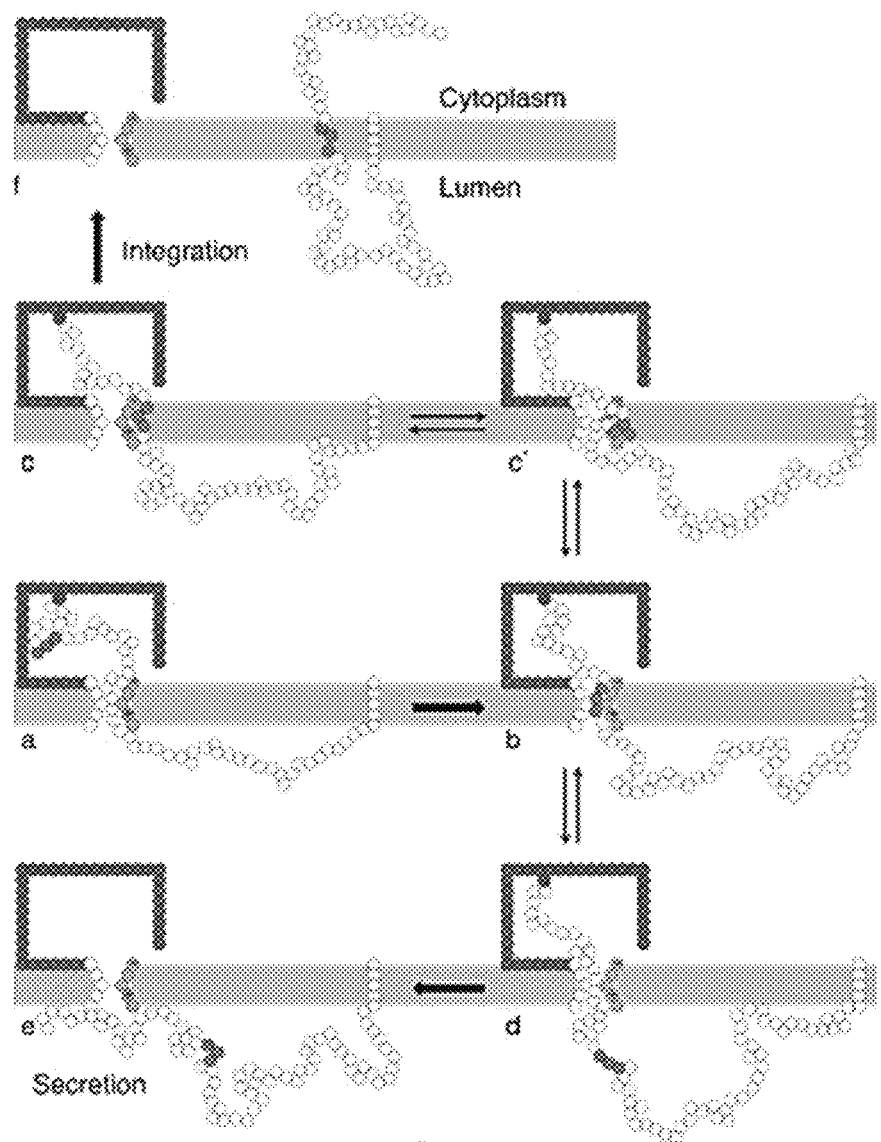
FIG. 10 shows a schematic illustrating kinetic pathways for cotranslational Protein Translocation and Membrane Integration Obtained from Direct CG Simulations. This figure is identical to FIG. 4, except the full N-terminal anchor domain of the protein nascent chain is shown here. The N-terminal anchor TM is fixed in the simulations at a distance of 20 nm from the translocon.

The translated protein sequence is comprised of three components, including the N-terminal anchor domain, the H-domain, and the C-terminal tail domain. In all simulations, the N-terminal anchor domain includes 44 type-Q CG beads that link the H-domain to an anchor TM that is fixed in the $N_{cyt}/C_{exo}$ orientation (FIG. 10). The H-domain is comprised of the sequence $PX_3P$, where the X-type CG beads have variable hydrophobicity. The C-terminal domain includes a hydrophilic sequence of CG beads with periodic hydrophobic patches (poly-$Q_5V$), following the hydrophobicity profile of the dipeptidyl aminopeptidase B (DPAPB) protein studied by Junne and colleagues.

Stop-transfer efficiency is studied as a function of the hydrophobicity of the H-domain, the C-terminal tail length (CTL), and the ribosomal translation rate. For the purposes of an embodiment of the present disclosure, CTL has been considered in the exemplary range of 5-45 beads (15-135 residues), and water-membrane transfer free energies for the H-domain has been considered in the exemplary range of $\Delta G/k_B T=[-5,5]$ $\Delta G/k_B T=[-5,5]$, where $\Delta G\Delta G$ corresponds to the sum over the individual transfer free energies of the CG beads in the H-domain.

CG trajectories are initialized with the H-domain occupying the ribosome-translocon junction, prior to translation of the C-terminal domain (FIG. 5, state a). Each CG trajectory is terminated after full translation of the protein C-terminal domain, either when the H-domain integrates into the membrane and diffuses a distance of 16 nm from the translocon or when both the H-domain and the C-terminal domain fully translocate into the lumenal region. The N-terminal anchor TMD of the protein nascent chain is fixed at a distance of 20 nm from the translocon (FIG. 10). The simulations thus assume that the H-domain membrane integration mechanism does not involve direct helix-helix contacts with the N-terminal anchor TMD. Full details of the simulation protocol are provided in the Extended Experimental Procedures section.

Figure 6A:
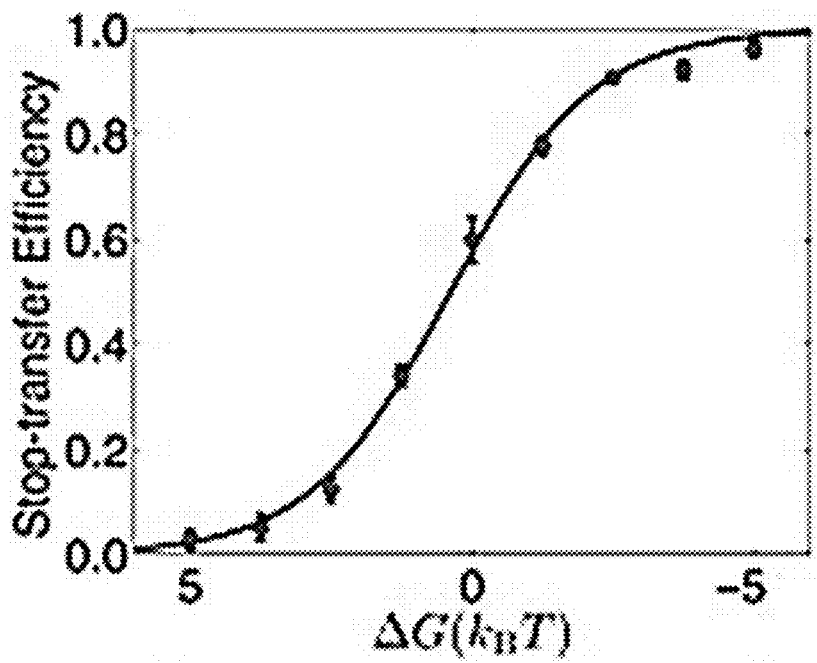
FIGS. 6A-6D, show charts illustrating CG simulation results for TMD partitioning. In particular.
Figure 6B:
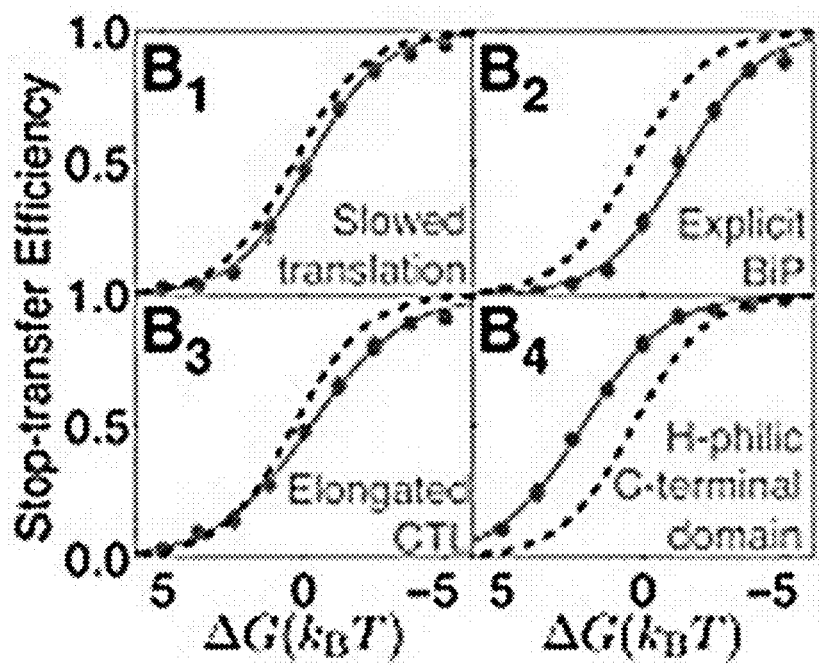
Figure 6C:
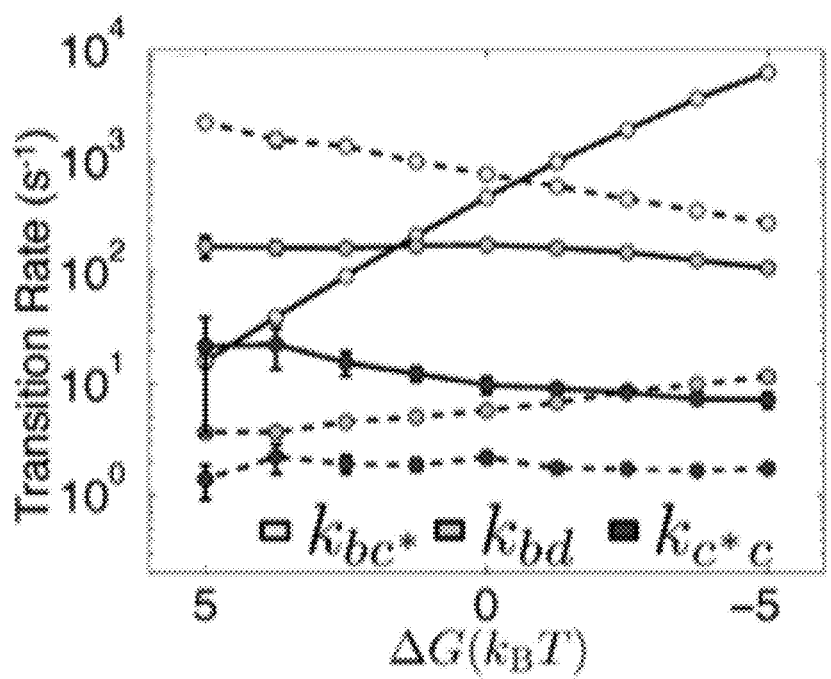
Figure 6D:
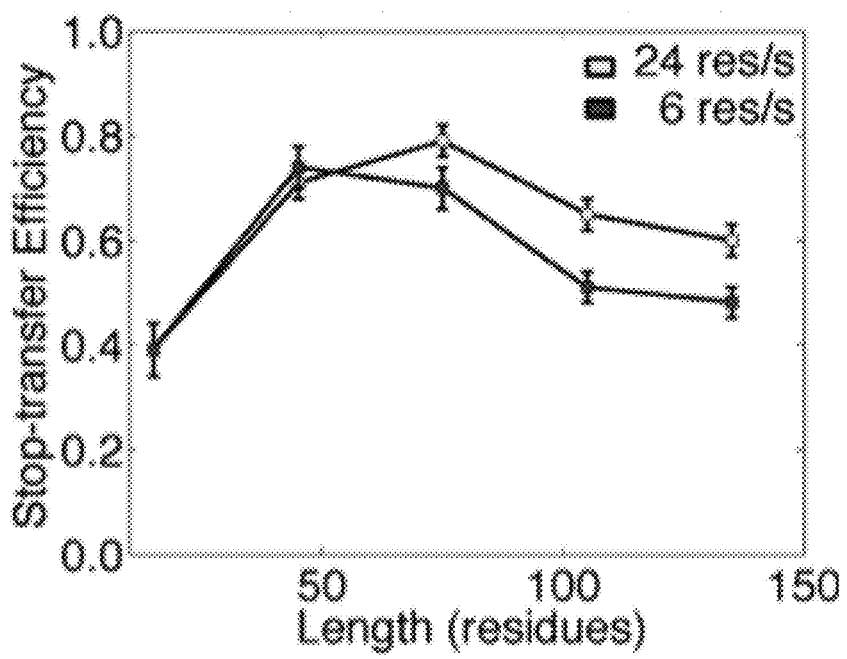
Figures 7A, 7B:
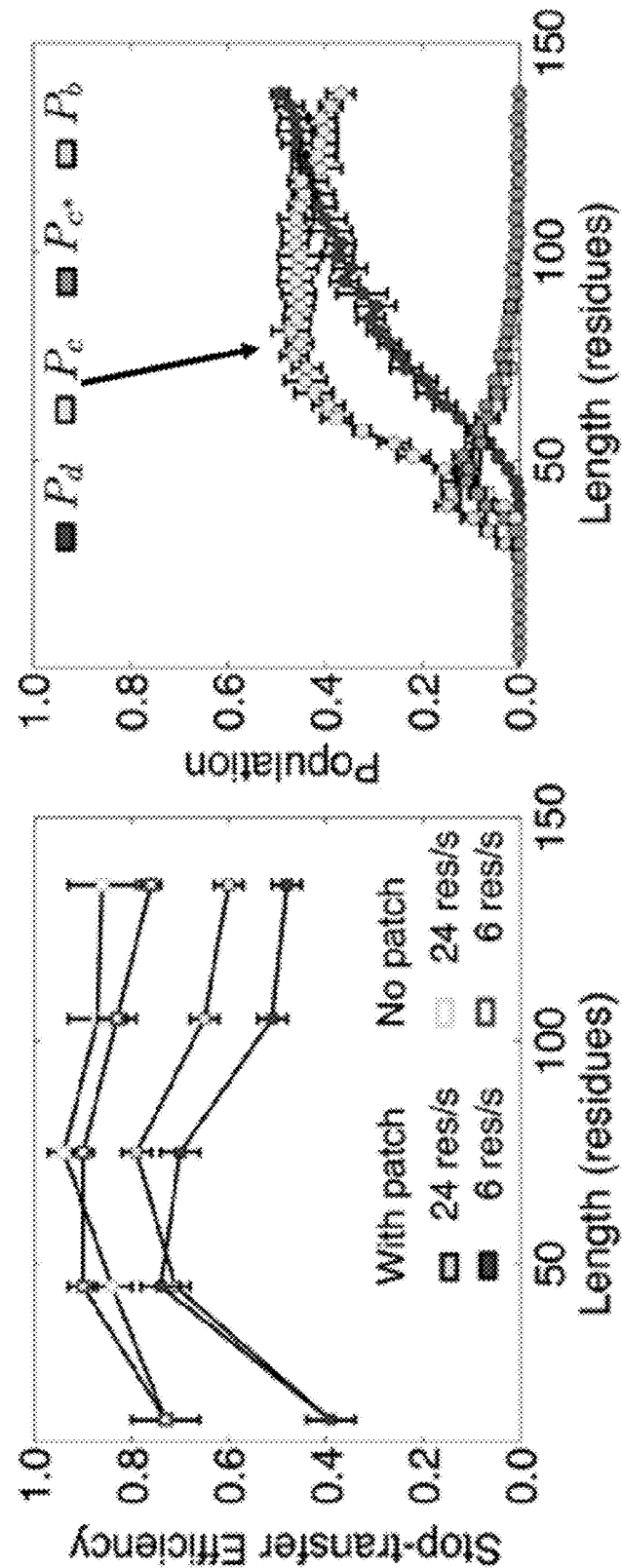
FIGS. 7A-7H show charts illustrating additional CG Simulation Results for Stop-Transfer Efficiency, related to FIGS. 6A-6D.
Figure 7C:
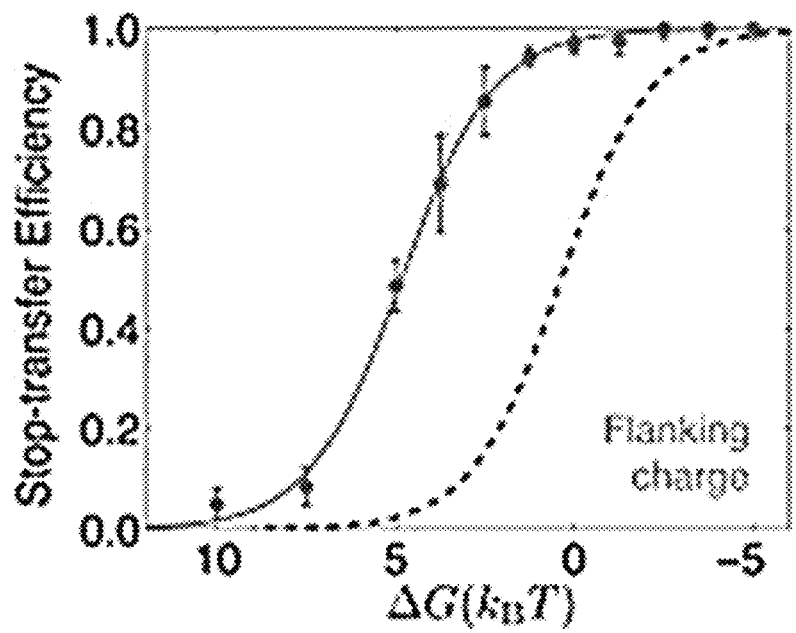

FIGS. 6A-6D present the calculated dependence of stop-transfer efficiency on the hydrophobicity of the H-domain, the length and hydrophobicity of the protein C-terminal domain, and the ribosomal translation rate. Each data point in FIG. 6A, FIG. 6B and FIG. 6D is obtained from over 600 independent nonequilibrium CG trajectories. The simulation times for these trajectories span the range of 3 to 100 s. FIGS. 7A-7C provide additional tests and comparisons of the simulation method against stop-transfer experiments, analyzing factors that include charged residues flanking the H-domain, hydrophobic patches on the C-terminal domain, and changes in protein translocation time.

Figure 7D:
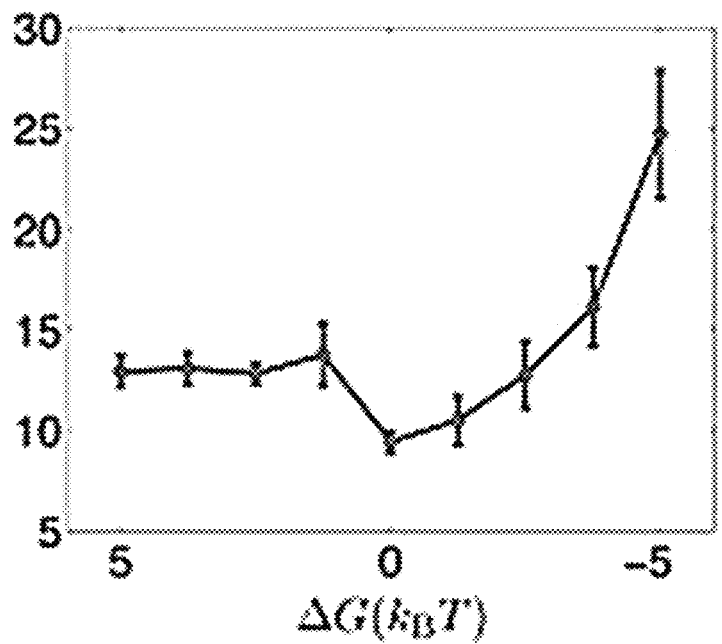
Figures 7E, 7F:
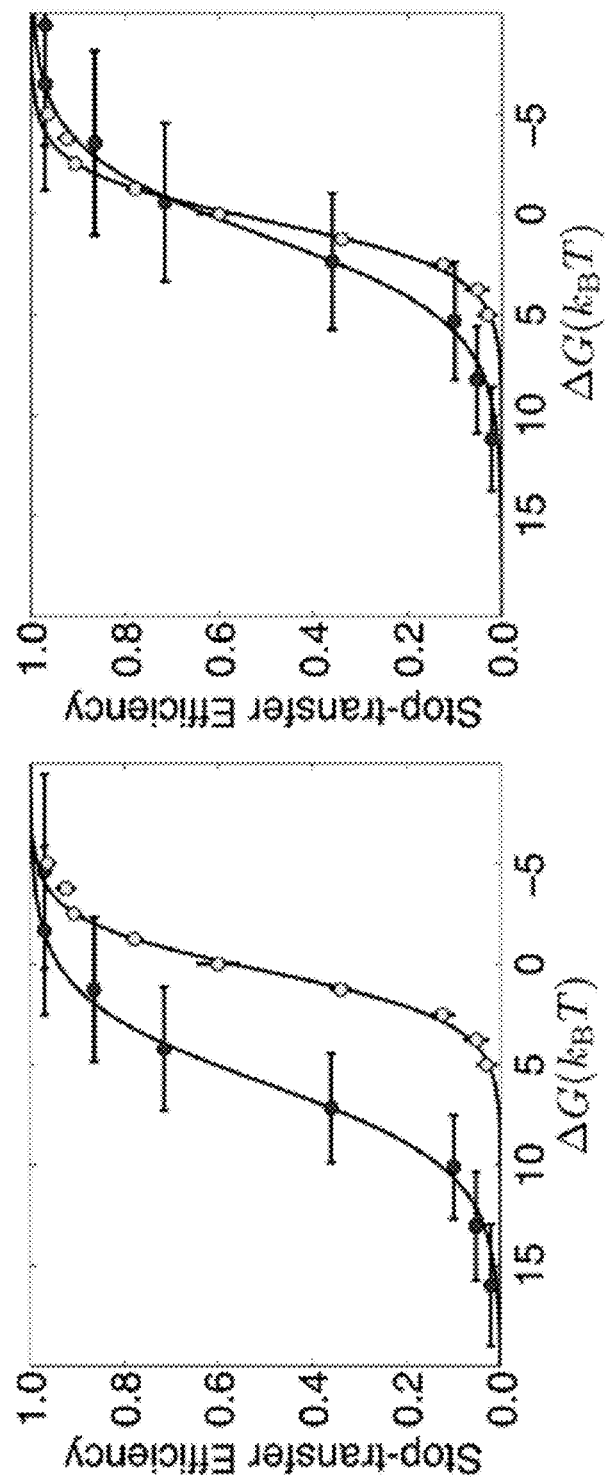
Figures 7G, 7H:
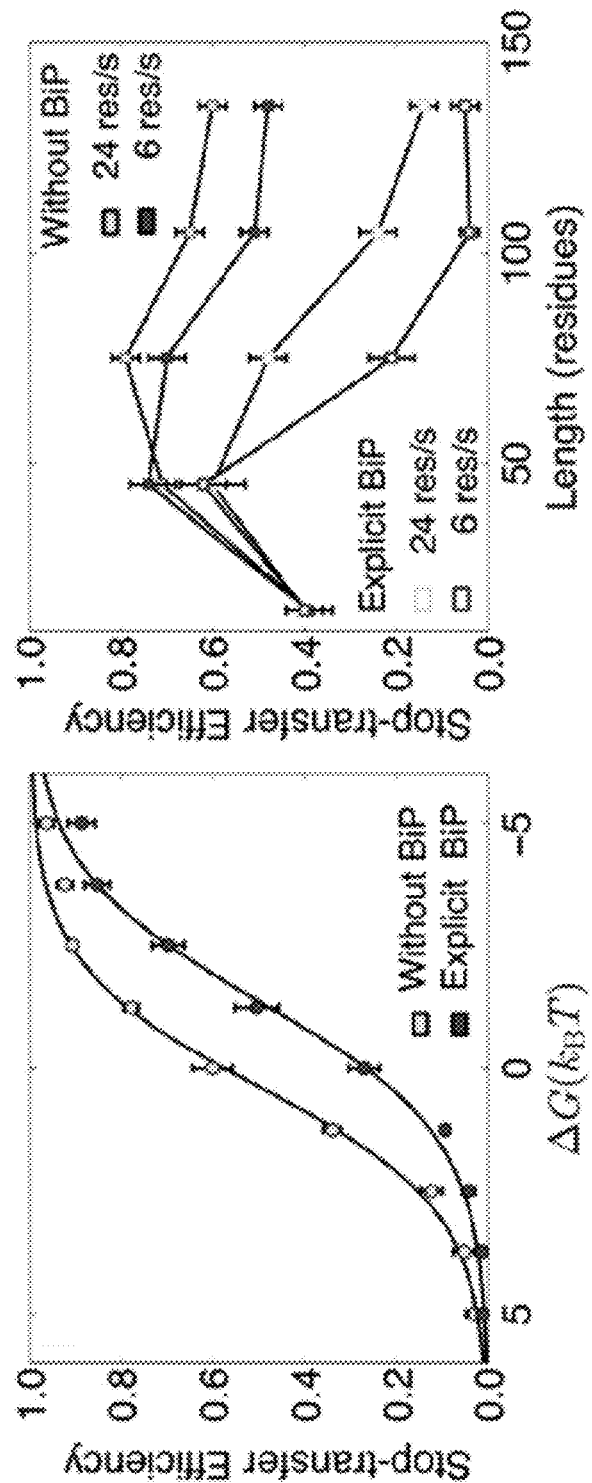

In FIG. 6A, the stop-transfer efficiency is plotted as a function of the H-domain transfer FE, $\Delta G$, for proteins with a CTL of 75 residues. The simulation method recovers the experimentally observed sigmoidal dependence of stop-transfer efficiency on H-domain hydrophobicity. The curve in the figure corresponds to the state population for a system in apparent two-state thermal equilibrium, $$P_I(\Delta G) = (1+\exp[-\beta\alpha\Delta G+\gamma])^{-1}, \quad \text{[Equation 11]}$$

where $\alpha = -0.80$, $\gamma = 0.29$ and $\beta = (k_B T)^{-1}$ is the reciprocal temperature, see also FIGS. 7E-7F. The physical origin of this sigmoidal dependence of the stop-transfer efficiency, as well as the physical interpretation of the parameters $\alpha$ and $\gamma$, is a focus of the following analysis.

Panels B1-B4 of FIG. 6B present the calculated relationship between stop-transfer efficiency and H-domain hydrophobicity in systems for which either the ribosomal translation rate is slowed from 24 res/s to 6 res/s (panel B1), backsliding of the protein nascent chain is inhibited to explicitly model the effect of the lumenal BiP binding (panel B2), the CTL is increased from 75 residues to 105 residues (panel B3), or the hydrophobic patches (V-type beads) in the C-terminal domain are replaced with hydrophilic, Q-type beads (panel B4). In each case, the integration probability preserves the sigmoidal dependence on $\Delta G$, and the best-fit value for the parameter a in each case is remarkably unchanged from the case in FIG. 6A. For the four cases presented in panels B1-B4 of FIG. 6B, fitting the simulation data to Equation 11 yields $\alpha = \{-0.77\pm0.08, -0.74\pm0.009, -0.60\pm0.06, -0.68\pm0.05\}$, and $\gamma = \{0.14\pm0.11, 1.0\pm0.19, -0.15\pm0.09, -1.44\pm0.13\}$.

In each case, the 95% certainty threshold for the sigmoidal fit is also indicated. The cases shown in panels B1-B3 OF FIG. 6B each lead to a decrease in the stop-transfer efficiency for a given value of $\Delta G\Delta G$ (i.e., a rightward shift of the sigmoidal curve with respect to that obtained in FIG. 6A), whereas decreasing the hydrophobicity of the C-terminal domain residues in case of panel B4 of FIG. 6B leads to an increase in stop-transfer efficiency.

11. Origin of Hydrophobicity Dependence in TMD Partitioning

FIG. 5 introduces the primary mechanisms according to which the ensemble of CG trajectories are observed to follow in the simulations. Along the pathway to membrane integration, trajectories pass through configurations for which the H-domain occupies the translocon channel (FIG. 5, state b), the membrane-channel interface across the open LG (state c*), and the membrane region outside of the translocon with the LG closed (state c); upon completion of translation and release of the protein nascent chain, it diffuses into the membrane to reach the integration product (state f). Along the pathway to protein translocation, trajectories also pass through state b, before proceeding to configurations in which the H-domain occupies the lumen with the C-terminal domain threaded through the channel (state d); upon completion of translation, the C-terminal domain is secreted through the channel, yielding the translocation product (state e).

Figure 8A:
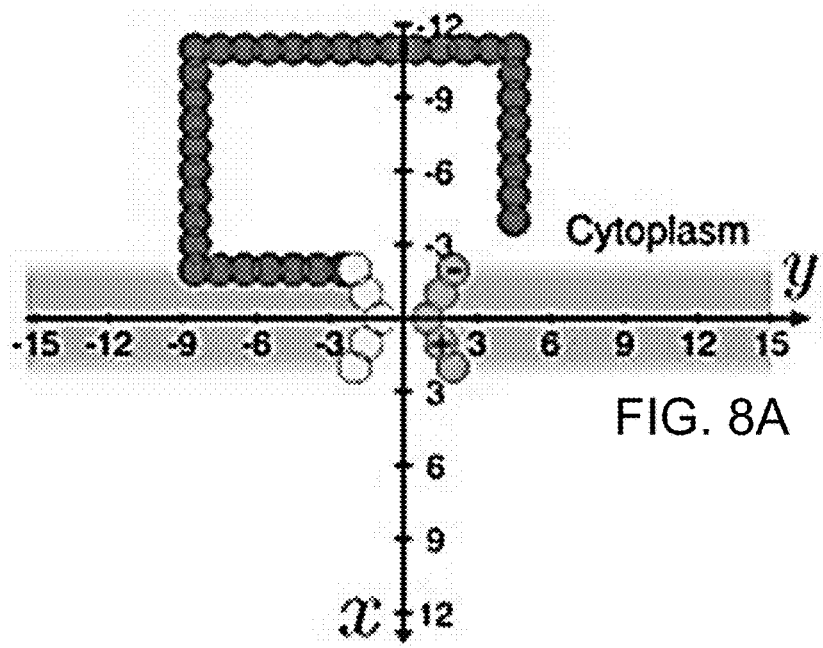
FIGS. 8A-8B show schematic illustrating coordinate System and Regions of the simulation method, related to FIG. 1, FIG. 2, and FIG. 5.
Figure 8B:
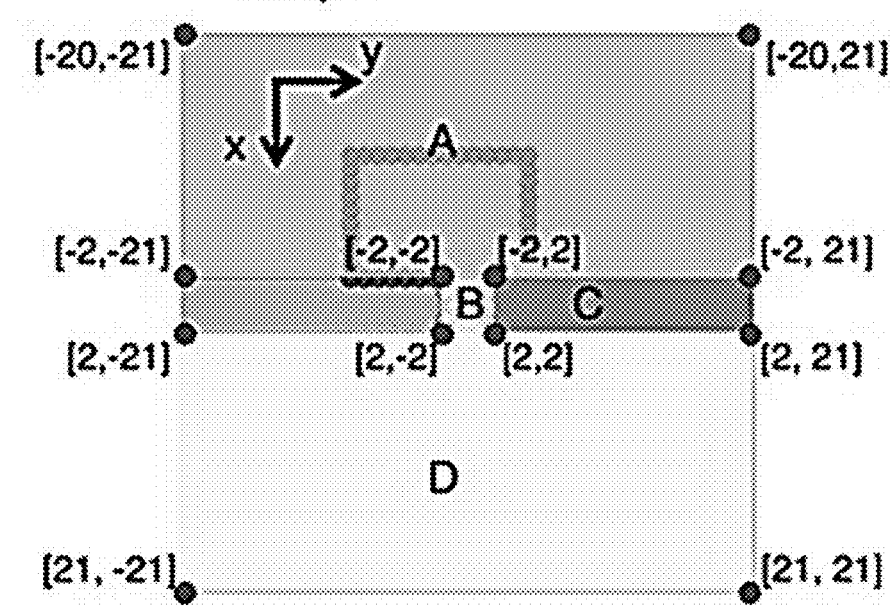
Figure 9A:
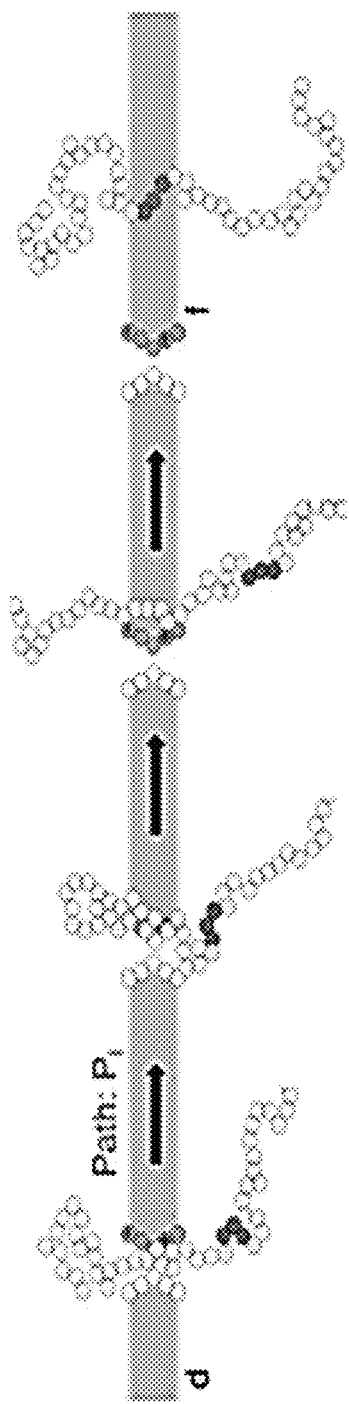
Figure 9B:
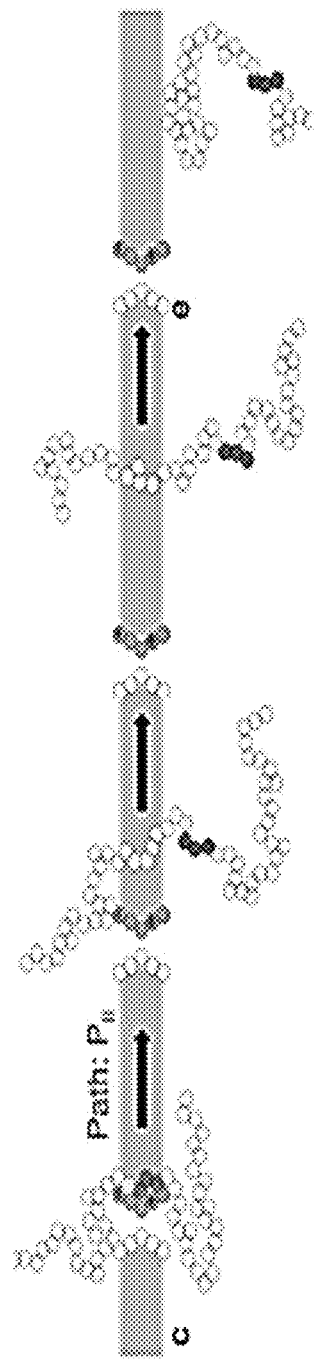
Figures 9C, 9D:
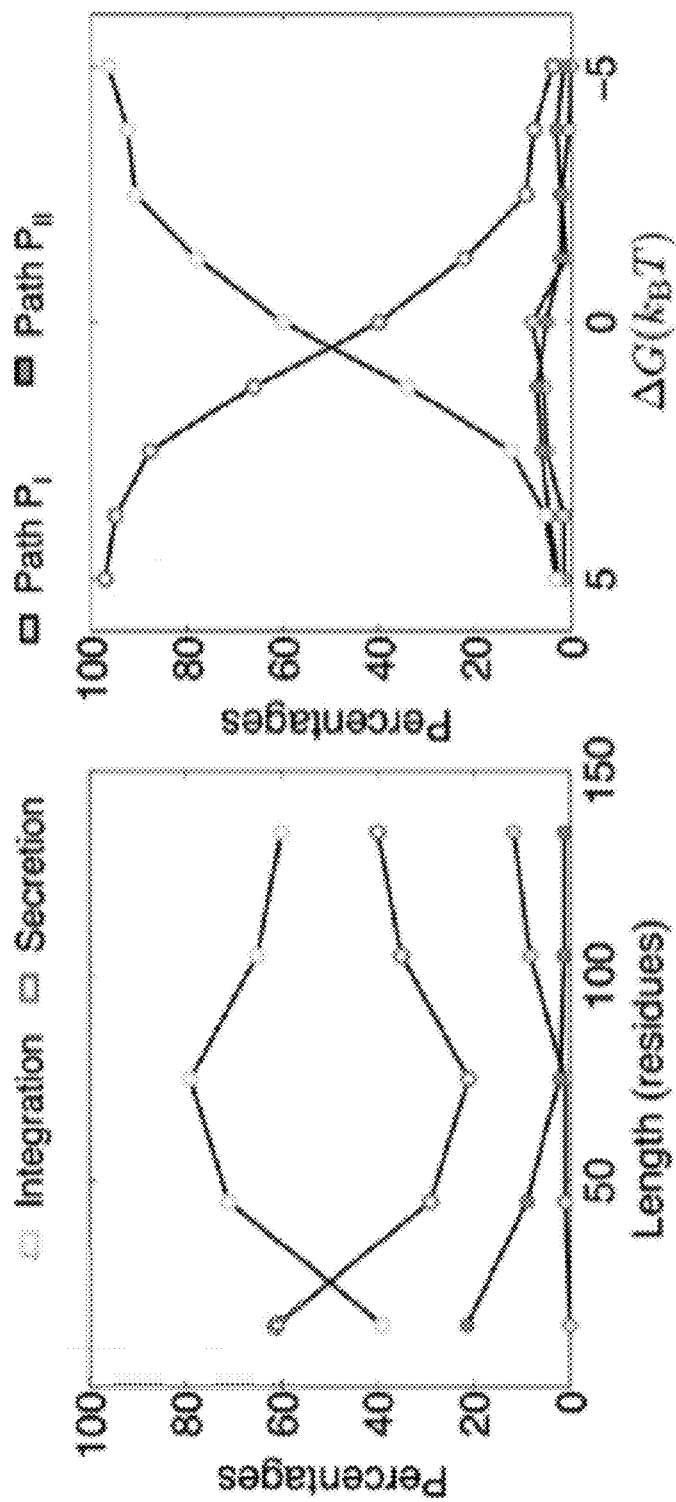

In addition to the dominant pathways depicted in FIG. 5, minor pathways for translocation and integration are observed for very short and very long CTL (FIG. 9A). Complete definitions for the states in FIG. 5 in terms of the coordinates of the simulation method are provided in FIGS. 8A-8B. It should be emphasized that trajectories do not irreversibly pass through the intermediate states in FIG. 5, as many trajectories backtrack repeatedly, starting down one pathway before finally proceeding down the other.

FIG. 6C presents the equilibrium transition rates among the states in FIG. 5, which are obtained from the frequency of inter-state transitions in long CG trajectories of a protein nascent chain with a 75 residue C-terminal domain tethered at its C terminus to the ribosome exit channel. The calculation is repeated for proteins with a range of values for the H-domain hydrophobicity, $\Delta G\Delta G$. It is clear from the figure that partitioning of the H-domain across the LG of the translocon (i.e., forward and reverse transitions between states b and c*) occurs on a faster timescale than most other transitions in the system. Furthermore, the rates $k_{bc^*}$ and $k_{c^*b}$ are strongly dependent on the hydrophobicity of the H-domain, whereas the other transition rates are only weakly dependent on $\Delta G\Delta G$.

The results in FIG. 6C (as well as the more extensive kinetic analysis of the CG trajectories in the 'Analytical Model for TMD Partitioning' section at pages S8-S10 of the above mentioned *Long-Timescale Dynamics and Regulation of Sec-Facilitated Protein Translocation*, B. Zhang and T. F. Miller, Cell Reports 2, 927-937 and S1-S24, Oct. 25 2012, incorporated herein by reference in its entirety) reveal the mechanistic origin of the observed sigmoidal dependence of TMD partitioning on H-domain hydrophobicity (FIGS. 6A-6B). The nascent protein H-domain achieves rapid, local equilibration (or partitioning) across the translocon LG; this partitioning is highly sensitive to the hydrophobicity of the H-domain, which gives rise to the characteristic sigmoidal dependence of the curves in FIGS. 6A-6B and determines the value of the parameter a. Moreover, rapid partitioning of the H-domain is kinetically uncoupled from slower steps in the mechanisms of integration and translocation, which leads to the insensitivity of a in fitting the various sets of data in FIGS. 6A-6B. Kinetic and CTL effects in TMD partitioning arise from competition among slower timescale processes in the secretion and integration pathways. These effects are manifest in parameter $\gamma$ and lead to lateral shifts of the sigmoidal curves in FIG. 6B.

It should be noted that a mechanism involving local equilibration of the H-domain between the translocon and membrane interiors is consistent with the interpretation of recent experimental studies of stop-transfer efficiency. However, the analysis presented in this disclosure additionally reconciles the roles of both kinetic and thermodynamic effects in governing stop-transfer efficiency, and provides a basis for understanding the lateral shifting of the sigmoidal curves both in FIG. 6B and in possible future experiments.

12. Kinetic and CTL Effects in TMD Partitioning

The direction of the lateral shifts of the curves in panels B1-B4 of FIG. 6B can also be understood from analysis of the CG trajectories. In panel B1, slowing the translation rate allows for better equilibration among the states d and c prior to release of the protein from the ribosome, leading to increased population of the thermodynamically favored state d and enhancement of the secretion product. FIGS. 9E-9F demonstrate the relative increase of the nonequilibrium population in state d upon slowed ribosomal translation. In panel B2 of FIG. 6B, the BiP motor enhances the secretion product by biasing against trajectories that backslide from state d. Panel B3 of FIG. 6B exhibits a combination of these two effects, with the elongated C-terminal domain allowing more time for the protein conformation to interconvert between states d and c prior to release from the ribosome (see FIGS. 9E-9F) and with a decreased rate of backsliding from state d with longer CTL (see FIG. 9G). Finally, panel B4 of FIG. 6B reveals that decreased hydrophobicity of the C-terminal domain residues leads to increased stop-transfer efficiency. Without hydrophobic patches, the C-terminal domain residues in the translocon channel do little to stabilize opening of the LG; therefore, once the system reaches state c along the pathway to membrane integration, it is less likely that the H-domain will return to the channel interior and then undergo secretion (see FIGS. 7A-7B).

FIG. 6D provides a more complete view of the connection between CTL, ribosomal translation rate, and stop-transfer efficiency. At relatively long CTL (≥75 res), stop-transfer efficiency decreases for longer proteins and for slower ribosomal translation, as was previously discussed in connection with panels B1 and B2 of FIG. 6B. However, at short CTL (≤50 res), stop-transfer efficiency increases for longer proteins and exhibits no dependence on the ribosomal translation rate. In the short-CTL regimen, slowing ribosomal translation affords little additional time for the protein conformation to interconvert between states d and c prior to release from the ribosome (FIGS. 9E-9F). There is thus no enhancement of the nonequilibrium population for state d and no corresponding change in stop-transfer efficiency. Previous experimental studies of stop-transfer efficiency involving relatively short CTL find no dependence of stop-transfer efficiency on translation rate, as it is consistent with the results in FIG. 6D. Experimental results for longer CTL that test the predicted kinetic effect upon slowing ribosomal translation would be of significant interest.

13. Additional Validation and Prediction for Stop-Transfer Efficiency

13A—Hydrophobic Patches in the C-Terminal Domain

FIG. 7A illustrates the dependence of the CG simulations of stop-transfer efficiency on hydrophobic patches in the C-terminal domain of the protein nascent chain. Removal of the hydrophobic patches leads to a shift in favor of increased membrane integration. Without hydrophobic patches, the C-terminal domain residues in the translocon channel do little to stabilize opening of the LG. Therefore, once the system reaches state c (FIG. 5) along the pathway to membrane integration, it is less likely that the H-domain will return to the channel interior and then undergo secretion. The result is an increase in membrane integration upon removal of the hydrophobic patches from the C-terminal domain. The inventors note that this interpretation is consistent with the observed enhancement of the nonequilibrium state population for state c, $P_c$, upon removal of the hydrophobic patches from the C-terminal domain (see FIG. 7B). Sensitivity of stop-transfer efficiency to C-terminal domain sequence has also been observed in experimental studies.

13B—Charged-Residue Mutations Flanking the H-Domain

Experimental studies have also found that charged residues flanking the nascent-protein H-domain affect stop-transfer efficiency. FIG. 7C illustrates this effect in the simulation method presented in this disclosure. The dashed line in the figure corresponds to the stop-transfer efficiency results reported in FIG. 6A. The dark data set is obtained using the same protein sequences, except that the three CG beads in the C-terminal domain that directly flank the nascent protein H-domain are mutated from being hydrophilic and neutral (Q-type) to being hydrophilic and positively charged (R-type).

As is seen in FIG. 7C, the charged-residue mutations lead to a substantial shift toward increased membrane integration of the nascent-protein H-domain. Analysis of the CG trajectories reveals the mechanistic basis for this trend. Whereas progress along the secretion pathway (state b to state d in FIG. 5) involves sacrificing the favorable electrostatic interaction between positively charged flanking beads on the nascent protein and the negatively changed bead on the translocon, progress along the integration pathway (state b to state c* to state c) allows this electrostatic contact to be preserved. In effect, the charged residues lead to enhancement of the nonequilibrium population of state c in favor of state d, which leads to an enhancement of the membrane integration product. These simulations suggest that the C-terminal positive charges enhance the stop-transfer efficiency of marginally hydrophobic TMD segments, which is consistent with experimental observation.

13C—Dependence of Protein Translocation Time on Nascent Protein Hydrophobicity

Previous stop-transfer experiments have concluded that hydrophobic nascent-protein segments exhibit stalling, or pausing, in the translocon channel. Protein translocation modeling has also led to the prediction that hydrophobic segments retard translocation due to lateral partitioning. FIG. 7D investigates this effect using the simulation method of the present disclosure. The average simulation time for trajectories to reach the secretion product is calculated. Trajectories that lead to the membrane integration product are not included in the average. The protein sequences and stop-transfer simulation protocols used to construct FIG. 7D are the same as those used to construct FIG. 6A.

For hydrophilic and amphiphilic H-domain sequences $\Delta G > -2k_BT$, the simulation method predicts relatively weak dependence of the protein translocation time on the H-domain hydrophobicity (FIG. 7D). However, for more strongly hydrophobic H-domain sequences, the translocation time is found to increase by a factor of 2-3. This increase in translocation time is in qualitative agreement with experimental studies. Furthermore, the results in FIG. 7D bear striking resemblance to the exponential increase in translocation time with H-domain hydrophobicity that is predicted in the literature. It is emphasized that any experimental or theoretical measurement of protein translation time should take care (as is done here) to avoid contamination due to the increased formation of membrane integration product with strongly hydrophobic H-domain sequences.

14. Model Parametrization and Validation

14A. CG Bead Transfer Free Energies and Charges

Transfer free energy (FE) values for bead-types R, E, L, Q, V, P used in the embodiments of the present application (see Table of FIG. 21) are comparable to experimental water-octanol transfer free energies for single Arg, Glu, Leu, Gln, Val, and Pro residues, respectively. Bead-types R and E, which are employed only in the topogenesis simulations in Signal Orientation and Protein Topogenesis in the main text, include charges of +2 and −2 to model the charged residues that flank the signal peptide (SP) in the engineered H1 ΔLeu22 protein considered in previous experimental work. The two positive charges correspond to the N-terminal Met residue and a neighboring Arg residue, and the two negative charges correspond to the two Glu residues at the opposite end of the SP. New bead types can be introduced in the current simulation method in a straightforward manner to describe distinct amino acid sequences as will be understood by a skilled person. Amino acid sequences can be directly mapped onto CG particles by summing the contributions to the hydrophobicity and charge of the individual amino acids of which the CG particle is comprised.

14B—Translocon Geometry and Charges

The positions of the CG beads that model the Sec translocon (see Table of FIG. 19 and FIGS. 8A-8B) reflect the hour-glass-shaped profile of the translocon from atomic-resolution crystal structures. At its cytosolic and lumenal mouths, the channel diameter widens to approximately 24 Å, and it narrows to approximately 8 Å in the membrane interior.

14C—Ribosome Geometry

Confinement effects due to the ribosome (or any protein inserter) are explicitly included in the simulation method (see FIG. 19 and FIGS. 8A-8B).

In particular, since the protein inserter is modeled as an enclosure of CG beads (as well as a point at which newly-translated CG beads of the nascent protein appear), then there are physical effects that are predicted by the simulation method as a result of the nature of this enclosure of the CG beads. Such effects are referred to as "confinement effects." For example, only so many CG beads of the nascent protein can fit in the ribosomal enclosure on the cytosolic side of the membrane.

Electron microscopy (EM) structures of the ribosome in complex with the translocon reveal a large lateral opening above the cytosolic cup of the translocon, which is about 20 Å wide. The simulation method likewise includes a ribosomal enclosure that is of comparable size with respect to the volume occupied by nascent chain residues in the CG representation. Near the translocon LG, the ribosomal enclosure is partially open to the cytosol, as is seen in the EM structures. This opening prevents steric hindrance of membrane integration in the simulation method and enables access of the protein nascent chain to the cytosolic exterior of the membrane. The description of this geometry in the 2-dimensional embodiment of the simulation method is provided in FIG. 19, the geometry can be described in a 3-dimensional embodiment of the simulation method in more accuracy by directly mapping the geometry from available structural data, as will be understood by a skilled individual.

14D—Timescale for LG Opening

The opening and closing of the translocon LG is modeled stochastically with rates defined in Equations in the text above. In these expressions, the parameter $\tau_{LG}$ corresponds to the timescale for attempting LG opening or closing events. As in classical rate theory, this attempt timescale is related to the timescale required for the system to transiently pass between the open and closed configurations for the LG, which has been observed in previous MD simulations of translocon/peptide substrate/membrane systems. In a previous work by the inventors, it was shown that spontaneous translocon LG closing in the presence of a peptide substrate occurs on the timescale of approximately 300-500 ns. To explore the robustness of the simulation method to this parameter, the dependence of the type II integration has been calculated as a function of MDL for the RL6E SP sequence (see FIG. 3B), using $\tau_{LG}$=250, 500, 1000, and 2000 ns. The results show no significant differences among the four data sets and suggest that the CG calculations are very robust with respect to $\tau_{LG}$. A value of $\tau_{LG}$=500 ns is employed throughout the embodiments of the disclosure.

14E—FE for LG Opening

In the simulation method according to the present disclosure, a simple relationship between LG energetics and substrate hydrophobicity is being used, as described in Equation 10 and as also described in pages S3-S4 of the paper *Long-Timescale Dynamics and Regulation of Sec-Facilitated Protein Translocation*, B. Zhang and T. F. Miller, Cell Reports 2, 927-937 and S1-S24, Oct. 25 2012, incorporated herein by reference in its entirety.

14F—CG Bead Diffusion Coefficient

The diffusion coefficient D for the CG beads of the protein nascent chain is parameterized to reproduce the experimentally observed timescale for protein diffusion across the Sec translocon. Specifically, the inventors consider the measurements by Rapoport and colleagues of posttranslational translocation times for the 165-residue pre-pro-a factor (ppaF) (Matlack et al., 1999) (15). In these experiments, the protein substrate is initially bound to the Sec translocon in proteoliposomes; translocation is initiated via addition of adenosine triphosphate (ATP) and binding immunoglobulin protein (BiP), and the fraction of translocated protein is monitored as a function of time.

Description of modeling of such experiment is provided at pages S5-S6 of the paper *Long-Timescale Dynamics and Regulation of Sec-Facilitated Protein Translocation*, B. Zhang and T. F. Miller, Cell Reports 2, 927-937 and S1-S24, Oct. 25 2012, incorporated herein by reference in its entirety.

15. Protocols

15A—Trajectory Initialization and Termination (Protein Topogenesis Simulations)

Ribosomal translation is directly modeled in the CG simulations via growth of the nascent chain at the ribosome exit channel (shown in FIG. 2). CG trajectories are initialized from equilibrated configurations for the peptide of nine beads long. Different initial random number seeds are used for each independent simulation. During translation, CG beads are introduced sequentially at the C terminus, such that then nascent chain elongates. During this elongation process, the bead at the C-terminal tail is held fixed at the ribosome exit channel, and all other protein and translocon degrees of freedom are simulated as described elsewhere in the present disclosure.

Upon completion of protein translation, the C terminus of the inserted protein detaches from the ribosome exit channel, and the small subunit of the ribosome releases from the cytosolic mouth of translocon. Experimentally observed leakage of small molecules across the translocon following this ribosomal release suggests that the ribosome no longer seals the cytosolic mouth of the translocon. Ribosomal release is thus modeled by eliminating interactions associated with the ribosome CG beads.

Membrane integration trajectories are terminated after full translation of the protein mature domain, either when the SP integrates into the membrane in the type III orientation and diffuses to a distance of 16 nm from the translocon (state d, FIG. 2) or when the SP integrates into the membrane in the type II orientation. To meet the distance criterion, the y-coordinate for each bead in the nascent protein SP should be greater than 16 nm, using the coordinate system illustrated in FIG. S7. For proteins in the type II orientation, rather than running the CG trajectories until the SP diffuses a distance of 16 nm from the translocon (state g, FIG. 2), trajectories are terminated when the trajectories reach state f, for which the SP is integrated into the membrane and the translocon LG is closed.

As shown in FIG. 4C, termination of the type II integration trajectories at state f accounts for the effect of BiP binding to the lumenally exposed portions of the protein nascent chain.

15B—Trajectory Initialization and Termination (Stop-Transfer Simulations)

As in the topogenesis simulations, ribosomal translation is modeled via addition of peptide residues to the nascent chain at the ribosomal exit channel (shown in FIG. 5). The stop-transfer trajectory is initialized from the ensemble of equilibrated configurations for the protein with only 15 residues of the C-terminal domain translated, with the H-domain residing in the ribosome translocon junction (FIG. 5, state a).

Unbinding of the ribosome at the end of translation is modeled as in the topogenesis simulations. Upon completion of translation, the constraint on the C terminus of the protein nascent chain is removed and interactions between the CG beads of the ribosome and protein nascent chain are eliminated.

Each CG trajectory is terminated after full translation of the protein C-terminal domain, either when the H-domain integrates into the membrane and diffuses a distance of 16 nm from the translocon (state f, FIG. 5) or when both the H-domain and the C-terminal domain fully translocate into the lumenal region (state e, FIG. 5). The N-terminal signal anchor of the protein is fixed at a distance of 20 nm from the translocon. The simulations thus assume that the H-domain membrane integration mechanism does not involve direct helix-helix contacts with the protein anchor domain.

15C—Definition of State c in FIG. 2 (Protein Topogenesis Simulations)

State c includes protein nascent chain configurations for which (i) the SP adopts the $N_{exo}/C_{cyt}$ orientation, (ii) all the hydrophobic beads in the SP occupy the membrane interior (FIGS. 8A-8B, Right, Region C), and (iii) the translocon LG is closed.

15D—Definition of States in FIG. 4 (Stop-Transfer Simulations)

For the purposes of quantitatively defining the states in FIG. 2, the configuration space for each CG bead is divided into four regions (FIG. 8B). These regions include the cytosolic region (Region A), the translocon region (Region B), the membrane region (Region C), and the lumenal region (Region D). State a (FIG. 5) is then defined to include configurations of the protein nascent chain for which all CG beads of the H-domain occupy the cytosolic region and for which no beads of the protein nascent chain (except those in the anchor domain) occupy the membrane region. State d includes configurations for which all CG beads of the H-domain occupy the lumenal region and for which no CG beads of the protein nascent chain (except those in the anchor domain) occupy the membrane region. State c includes configurations for which all three of the X-type CG beads of the H-domain occupy the membrane region and for which the translocon LG is in the closed state.

State b includes configurations for which the center-of-mass of the H-domain occupies the translocon region, while none of the three X-type beads occupies the membrane region. State c* includes configurations for which all three of the X-type beads occupies the membrane region, at least one of the other CG beads in the H-domain occupies the translocon region, and the translocon LG is the open state.

15E—Equilibrium Rate Calculations

The thermal rate constants reported in FIG. 6C are computed from long, equilibrium CG trajectories. Specifically, 100 independent CG trajectories are utilized, each of length T=40 s. The trajectories are performed with a fixed MDL for the protein nascent chain, and its C-terminal bead is held fixed at the ribosome exit channel. The ribosome remains in complex with the translocon throughout these equilibrium simulations. The equilibrium transition rates are obtained from the frequency of inter-state transitions in a long trajectory (Buchete and Hummer, 2008 (16); Sriraman et al., 2005 (17)), using $k_{ij}=N_{ij}/T_i$. Here, a transition from state i to state j is defined as an event in which the trajectory leaves state i and reaches state j before visiting any other state. The term Nij corresponds to the total number of transitions from state i to state j in a trajectory of length T. The term Ti corresponds to the amount of time that the system occupies state i during the trajectory. This estimate for $k_{ij}$ is obtained by averaging over estimates from the independent trajectories.

This protocol is repeated for the different values of ΔG reported in FIG. 6C.

The computational method of the present disclosure can be modified to improve the accuracy of the TABFs as compared to any given experimental data. The model can be changed to better match a set of constraints by changing parameters of the model such as the temperature, pressure, pH, electromagnetic fields and additional parameters affecting the TABF in the model. For example, growth temperature can have an effect on experimental TABFs for a protein expressed in a biological pathway. Therefore, changing the temperature parameter in the model can lead to model derived TABFs value that better match TABFs values from experiments performed with different growth temperatures. As an additional example, the model used in the experimental section as applied to IMP TatC can be modified by changing the number of amino acids represented by each bead to increase resolution, by modifying the protein inserter from ribosome to SecA to simulate post-translational translocation from co-translational translocation, by changing from a two dimensional projection to a three dimensional model to obtain a more representative model of the biological system, or by changing the physical properties of the membrane environment to simulate the physical properties of various biological membranes. In general modifications of the model can be performed to improve matching of the model derived TABF values with any set (e.g. predefined or experimentally derived) TABF values. Modifications of the model can also performed to change the computational difficulty of the TABF calculations (e.g. to simplify the difficulties and/or to increase the speed of the calculations). Exemplary modifications affecting computational difficult comprise changes of the model that result in a decrease of the amount of time required to calculate TABFs for any protein such as the use of a two dimensional projection instead of a three dimensional model and/or using CG beads with less than full atomistic resolution. Resolution of the model can also be increased or decreased to adjust the required time to determine TABFs or change the number of trajectories measured, which can also affect the accuracy of the TABFs derived from the model as compared to experimentally observed TABFs.

The present disclosure is also directed to a software package encompassing the features of the model in accordance with the present disclosure. Such a software package is useful in case a stand-alone product for performing the TABF modeling as such is desired. Such a software package can allow for a number of different inputs and outputs given set of constraints on either. By way of example, a software program can be realized in accordance with the teachings of the present disclosure, so that the program provides the TABF given the model as applied in the TatC examples of the present disclosure when given a protein primary structures. Additionally, a computer could be provided that contains such a software package.

Figure 22:
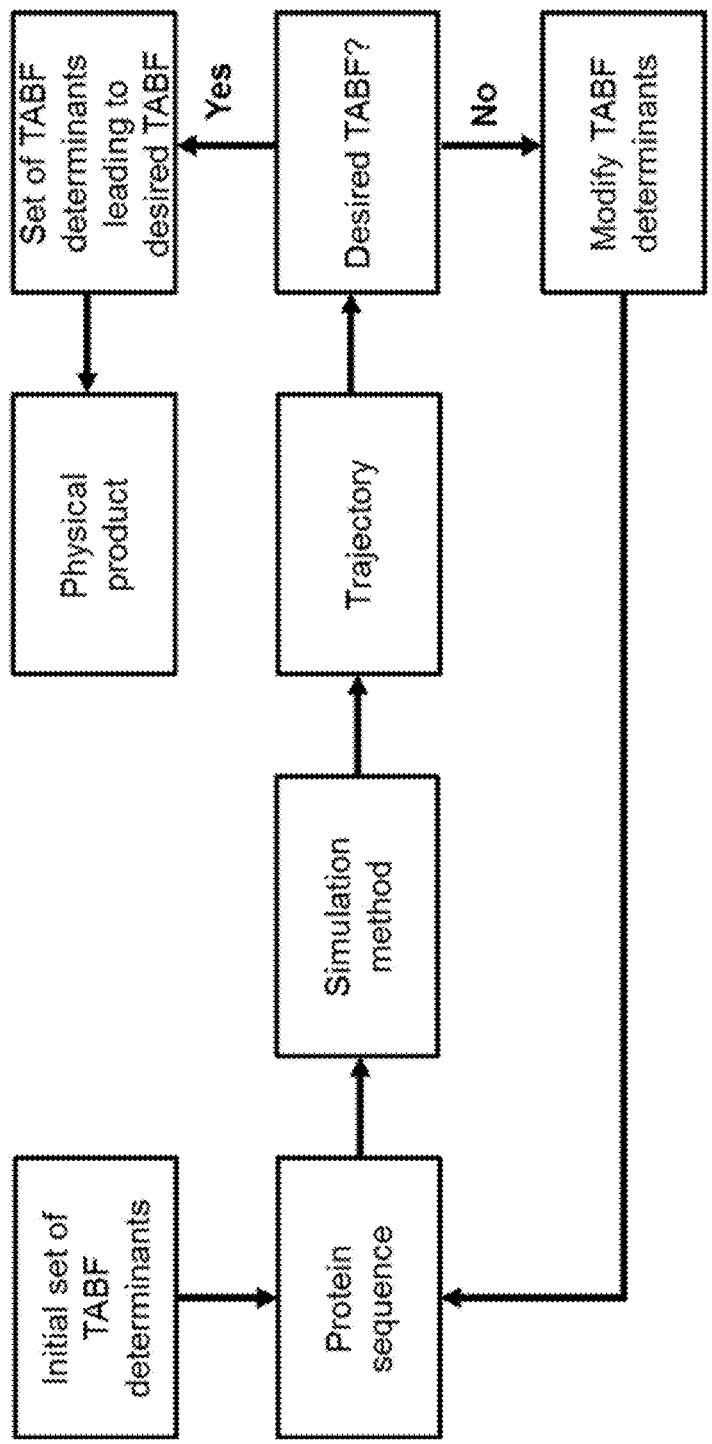
FIG. 22 shows a schematic representation of how the simulation methods claimed herein can be applied. Given an initial protein sequence, and a corresponding set of TABF determinants, as provided by the user, the simulation methods will provide a trajectory. This trajectory predicts a resulting TABF for the simulated system. The user can determine new TABF determinants as is described in the specific examples to optimize the TABF. The set of new TABF determinants is then included in the simulated system, and the updated system is again subjected to the simulation method. This cycle is repeated until a set of TABF determinants is identified that leads to the desired TABF.

In a further embodiment of the present disclosure, shown in FIG. 22, given a specific protein with desired TABF or set of TABF and possibly some constraints on TABF determinants, the TABF determinants can be modulated to provide the protein primary structure that leads to an optimal TABF. The TABF determinants can be changed by modifying the protein at the level of the primary structure or by modifying the system in which translocation occurs.

In particular, given a protein sequence or a set of protein sequences and desired a set of resulting TABFs, modifications to the TABF determinants for the simulation or the protein can be performed to affect the desired TABFs. This can be performed by changing the primary sequence of the protein to affect the TABF determinates for that protein. This can be done in a number of ways, including, but not limited to, randomly changing the sequence of the protein, changing the sequence of the protein to incorporate features seen in homologs, or using the TABF from the original sequence to find how the TABF differs and perform guided changed that rectify these particular TABF flaws. In each case the protein could be modified in ways such as by inserting, deleting, or changing individual natural or artificial amino acids, segments, and whole domains and proteins, adding post translational modifications such as glycosylation, and/or adding covalent bonds between amino acids such as by inserting cysteines. An example comprises that given the Mycobacterial TatC, which experimentally expresses poorly, the model would show that integration of the final TM is aberrant. Charged amino acids could be inserted into the protein sequence in a guided fashion until the desired TABF is returned from the model. This could also be performed by looking at TatC homolog distributions of charged residues after the final TM in TatC homologs and modifying the Mt TatC to add charges residues to the tail of the protein due to the presence of the charged residues on the tail of the other TatC proteins.

With reference to the predictions of the above embodiment, physical products (e.g. synthesized protein, plasmids and additional products identifiable by a skilled person.), see also related box in FIG. 22, based on these predictions can be fabricated.

In particular, the output of the above situation would be an ideal protein sequence or sequences. To produce any physical products desired there exist protocols for deriving them. The proteins sequence could be used to create any number of nucleotide sequences that code for the sequence. The protein sequence or sequences can be used to generate a number of physical products including an mRNA strand coding for the sequence, a DNA strand coding for the sequence, a plasmid containing a gene for the sequence, or the protein in a purified form. Short polynucleotides can be synthesized using techniques such as solid-phase oligonucleotide synthesis. Large polynucleotides could be created by connecting several short polynucleotides. Nucleotide sequences can be inserted into expression or any other vector using standard cloning procedures such as using a restriction enzyme to create complementary nucleotide overlaps between the vector and the inserted fragment followed by using a DNA ligase enzyme to covalently link the vector to the inserted fragment. Proteins can be provided by inserting a nucleotide sequence into an expression vector, expressing the protein in a suitable expression organism (such as E.Coli strains B121 Gold DE3 and Rosetta PLysS), and recovering and purifying the protein. An example would be that given the MtTatC sequence, the modifications of TABF determinants (e.g. values of each TABF determinant or a combination of values for a set of TABF determinants) that lead to the desired TABF can be inserted into an expression plasmid, such as pBAD containing the gene with the modification.

Figure 30:
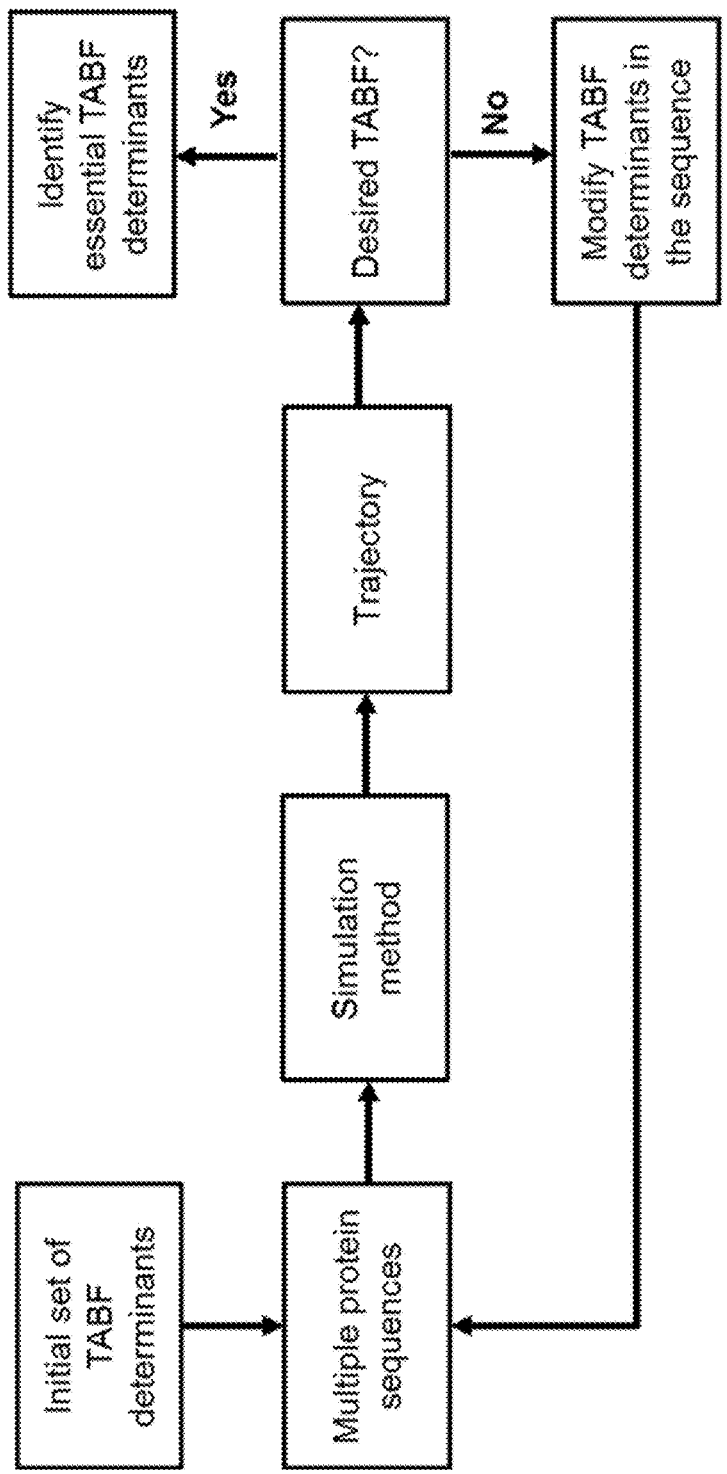

FIG. 30 shows a particular case of the embodiment of FIG. 22, where modifications only affect sequence-related TABF determinants. In particular, the modifications can be predicted by the model to lead to a desired TABFs. The expression plasmid can be transformed and expressed in an E.Coli strain optimized for protein expression.

Figure 31:
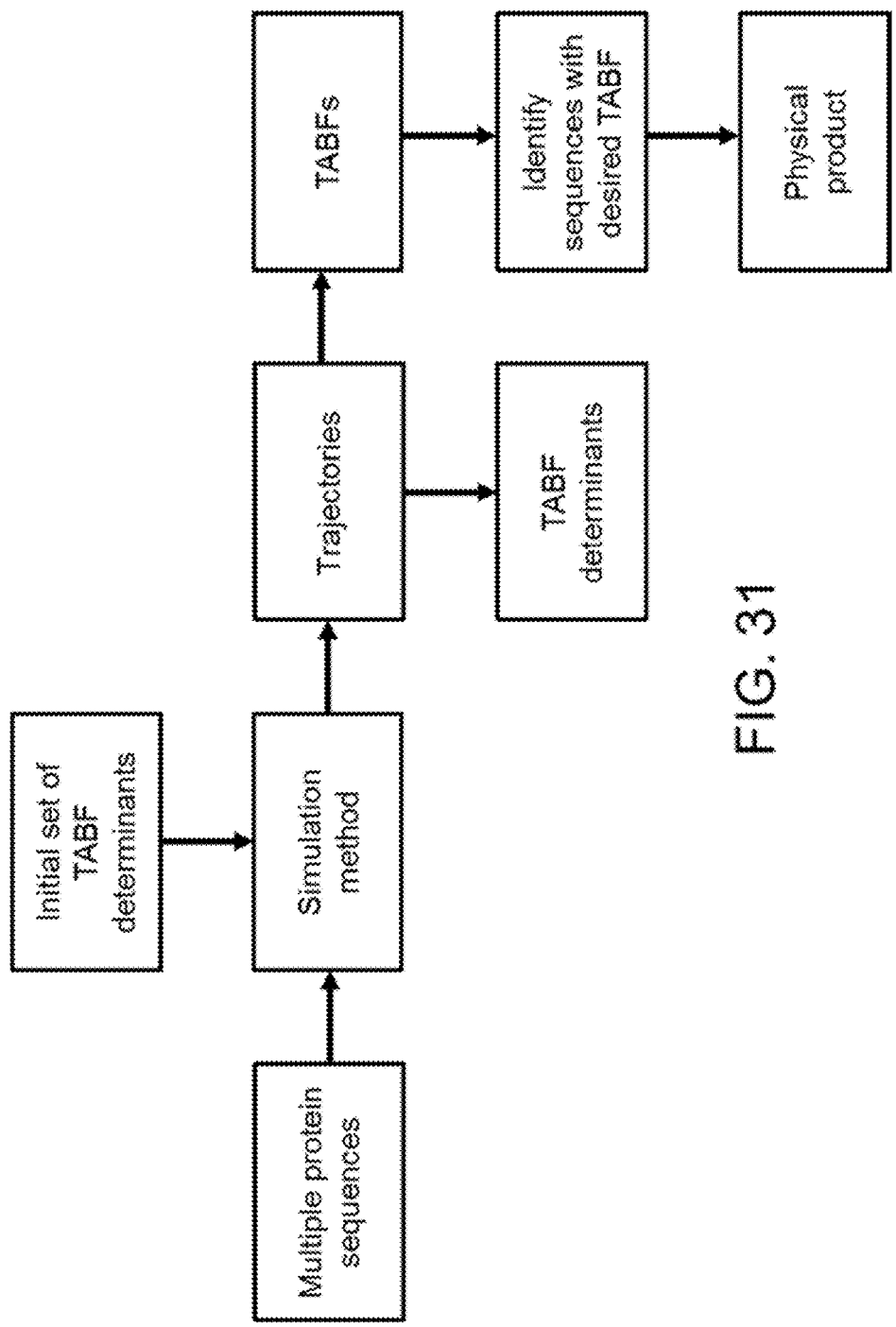

According to a further embodiment of the present disclosure, protein sequences can be screened from a class of proteins or a set of candidates, to identify those with desired TABF, as shown in FIG. 31.

In particular, given a set of protein sequences, the above described simulation method can be applied to all of the proteins in the set to find the protein sequence or sequences that produce TABFs that most closely match the desired TABF constraints. The set of proteins could be provided or could be found by searching for proteins that match a given a set of required traits. Additionally, if desired, the set of TABF determinants associated to the primary structure or primary structures that most closely match the desired TABF constraints can be provided, as also shown in FIG. 31. By way of example, given the need for any well expressed TatC, a variety of TatC homologs can be modeled until a well expressed TatC, such as Aa TatC, is identified, wherein the C-tail charge represent the TABF determinant, values thereof or combination thereof, identified in this specific example to mostly affect the specific TABFs considered (level of expression of TatC).

Physical products (e.g. synthesized protein, plasmids, and additional products identifiable by a skilled person.) can also be provided based on the predictions of the above embodiment, as also shown in a box of FIG. 31.

In particular, the output of the above situation would be an ideal protein sequence or sequences. To produce any physical products desired, protocols for deriving them exist. The proteins sequence could be used to create any number of nucleotide sequences that code for the sequence. The protein sequence or sequences can be used to generate a number of physical products including an mRNA strand coding for the sequence, a DNA strand coding for the sequence, a plasmid containing a gene for the sequence, or the protein in a purified form. Short polynucleotides can be synthesized using techniques such as solid-phase oligonucleotide synthesis. Large polynucleotides could be created by connecting several short polynucleotides. Nucleotide sequences can be inserted into expression or any other vector using standard cloning procedures such as using a restriction enzyme to create complementary nucleotide overlaps between the vector and the inserted fragment followed by using a DNA ligase enzyme to covalently link the vector to the inserted fragment. Proteins can be provided by inserting a nucleotide sequence into an expression vector, expressing the protein in a suitable expression organism (such as E.Coli strains B121 Gold DE3 and Rosetta PLysS), and recovering and purifying the protein. An example can be that given the need for any well expressed TatC, once a TatC that expresses well such as AaTatC is found it can be placed in an expression plasmid.

Figure 32:
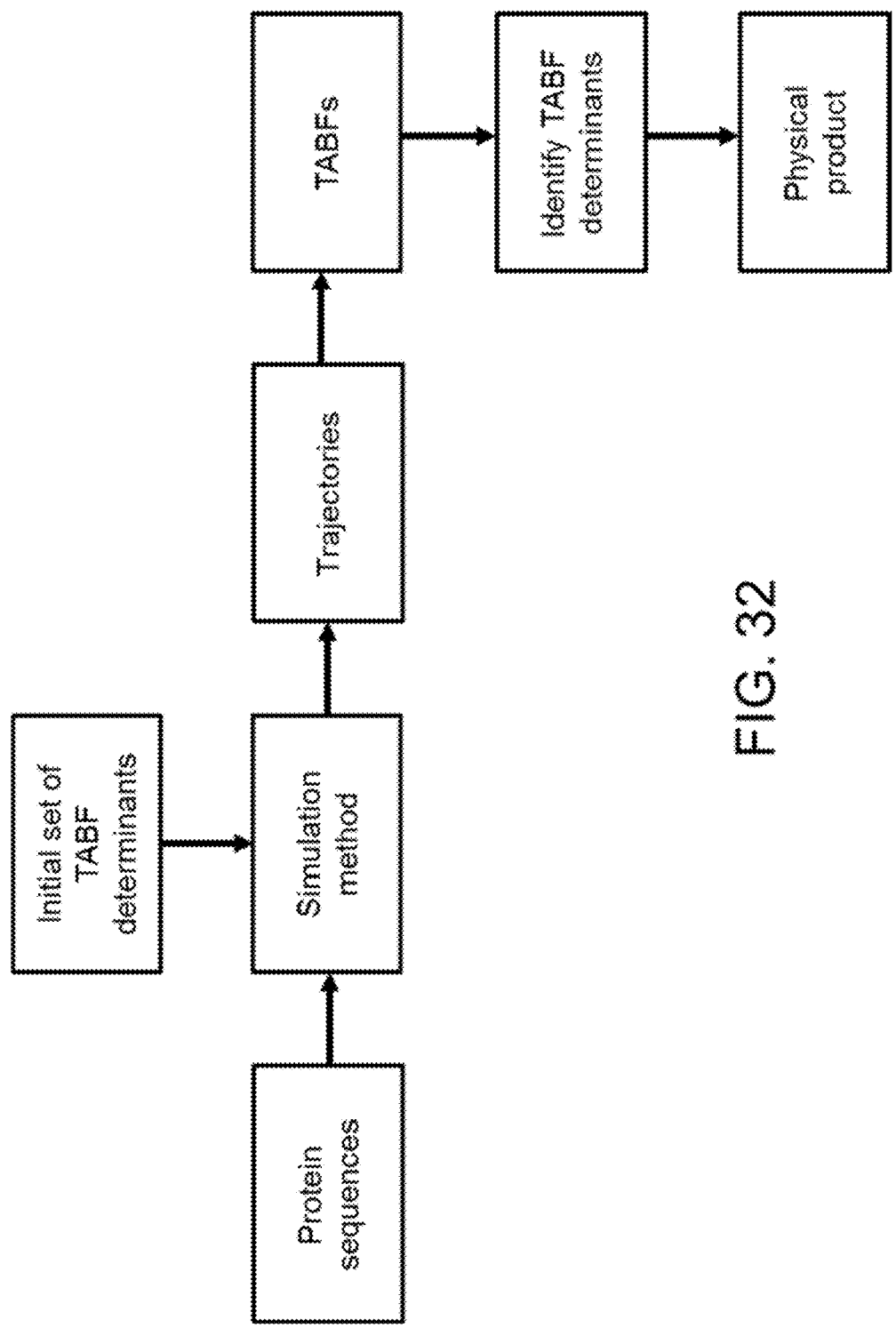
Figure 33:
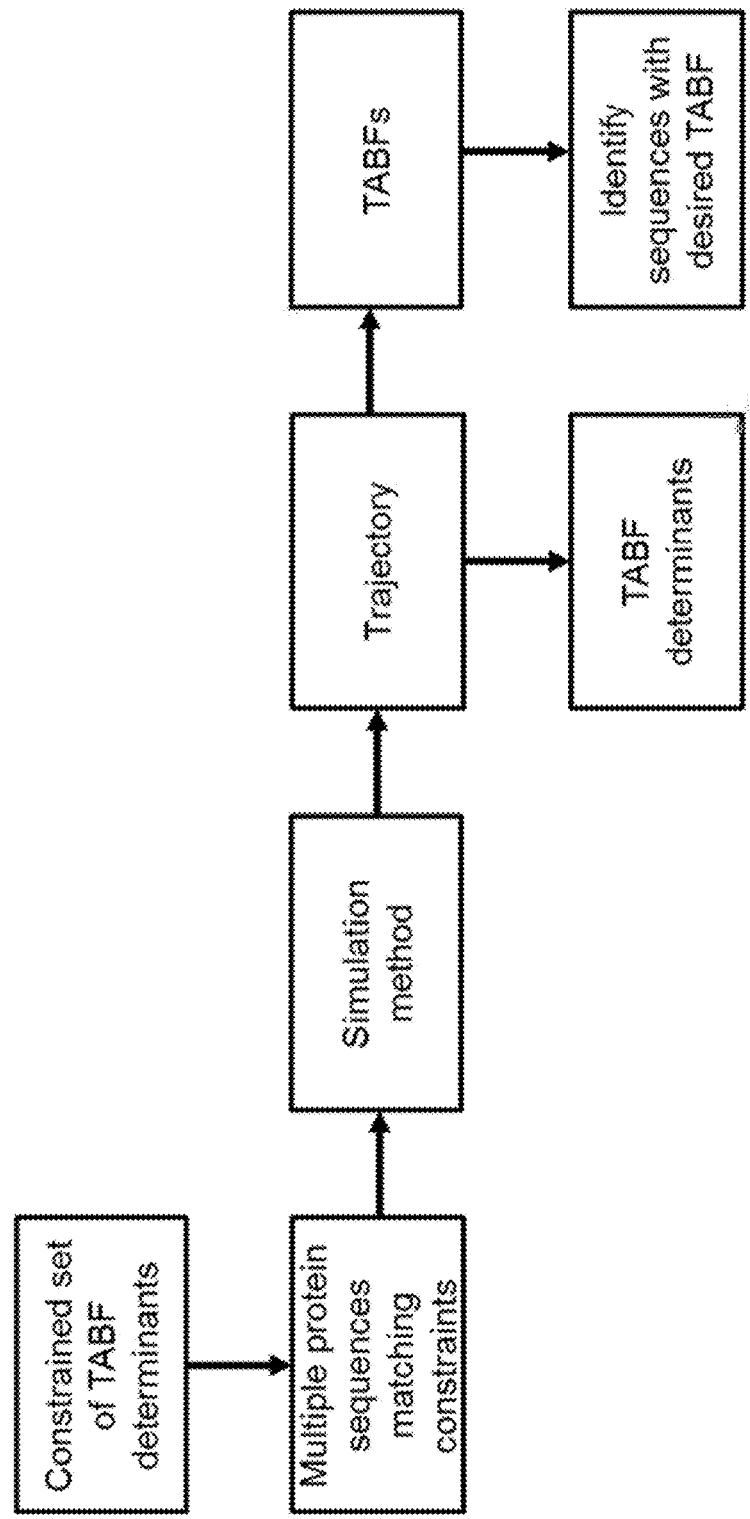

In accordance with yet another embodiment of the disclosure, protein sequences can be screened from a class of candidate expression systems and a given protein sequence or set of protein sequences, to identify the TABF determinant or determinants (e.g. an expression system or a sequence) that leads to desired TABF, as shown in FIG. 32.

By way of example, given a protein or a set of proteins and the desired TABFs, the method can be adjusted to simulate different candidate expression systems such as different expression hosts or expression conditions such as temperature. This can be done by changing physical constants associated with the model, changing the effect of the membrane to simulate different membranes among species, or modifying the inserter. An example would be to find the best organism for expressing AaTatC. The membrane environments for a variety of organisms could be replicated using the model. The membrane environment model variant that provides the desired TABF would inform which organism would be useful for expressing AaTatC.

In addition, physical products (e.g. synthesized protein, plasmids, and additional products identifiable by a skilled person.) can be provided based on the predictions of the above embodiment, as also shown in a box in FIG. 32.

In particular, the output of the above situation would be an ideal protein sequence or sequences. To produce any physical products desired there exist protocols for deriving them. The proteins sequence could be used to create any number of nucleotide sequences that code for the sequence. The protein sequence or sequences can be used to generate a number of physical products including an mRNA strand coding for the sequence, a DNA strand coding for the sequence, a plasmid containing a gene for the sequence, or the protein in a purified form. Short polynucleotides can be synthesized using techniques such as solid-phase oligonucleotide synthesis. Large polynucleotides could be created by connecting several short polynucleotides. Nucleotide sequences can be inserted into expression or any other vector using standard cloning procedures such as using a restriction enzyme to create complementary nucleotide overlaps between the vector and the inserted fragment followed by using a DNA ligase enzyme to covalently link the vector to the inserted fragment. Protein can be provided by inserting a nucleotide sequence into an expression vector, expressing the protein in a suitable expression organism (such as *E.Coli* strains B121 Gold DE3 and Rosetta PLysS), and recovering and purifying the protein. An example can be that given the AaTatC primary structure, AaTatC can be expressed in the organism corresponding to the membrane environment model that best fits the TABF, recovered and purified.

In accordance with a further embodiment of the disclosure, for a given protein sequence, constraints on the TABF determinants can be identified, that will ensure that TABF remain within targeted ranges.

In particular, given a protein primary structure or a set of protein primary structure and a range of desired TABFs, a protein primary structure can be modified to change their TABF determinants prior to applying the model to the sequences to determine to what extent changes to of a variety of TABF determinants can be modified still maintaining favorable TABFs, or those that cause the greatest change in TABFs. An example would be that provided the AaTatC primary structure and a desire to know how TABF determinants affect TABFs for AaTatC, the protein can be modified with a variety of changes such as adding or removing charged amino acids or increasing or decreasing TM length, which can have varying effects on the TABF. The TABF determinants changes based on the modifications that have the desired effect on AaTatC TABF, whether small or large or otherwise, can be identified.

In another embodiment of the disclosure, shown in FIG. 33, for a given set of constraints on the TABF determinants related to given protein sequences, protein sequences and/or expression systems (natural or otherwise) that lead to targeted TABFs are identified.

In particular, given a set of constraints on TABF determinants related to given protein sequences and a desired TABF, a variety of protein candidates such as representatives from each integral membrane protein pFam can be run through the model to find those that best meet the desired TABF. Additionally the model can be modulated to determine the expression system, natural or otherwise, and expression conditions that best meet the desired TABFs over all the proteins tested.

In a further embodiment, for a given protein sequence, new TABF determinants can be discovered from analysis of the predicted TABF levels, as shown in FIG. 34.

In particular, given a set of protein sequences, the resulting TABFs and the TABF determinants derived from these sequences could be analyzed to determine which TABF determinants correlate with each TABF. An example would be that given a set of TatC, the resulting TABFs could be used to determine that charge on the C-terminal tail correlates the most with TABFs. Therefore, the charge TABF determinant that is most helpful for determining TABFs for TatCs.

In yet another embodiment, given existing TABF experimental data, the simulation models can be used to provide explanations and interpretations for these data, as shown in FIG. 35.

In particular, given a protein sequence or set of proteins sequences and TABF experimental data, the proteins sequences could be run through the model after modifying the attributes of the model such as the inserter, the rate of translocation, and the membrane attributes. After running the sequences through the model with different modifications, those modifications that cause the TABFs to that most closely resemble the TABFs observed from the experimental data could be identified and used to provide explanations and interpretations of the experimental data. An example can be that given experimental data about the expression levels for a set of proteins, it could be determined that the modification to the model comprising slowing down the translocation rate that leads TABFs that correlate best to the experimental data are slowing down the rate at which amino acids are translocated by the inserter. If the mRNA sequences for the set of proteins all are enriched in rare codons, which is thought to slow translation by the ribosome, the presence of rare codons could be given as an explanation for the TABFs observed experimentally.In a further embodiment, for a given protein sequence and TABFs, modifications that do not affect TABF can be identified, as shown in FIG. 36.

In particular, given a protein sequence or a set of protein sequence, modifications to the protein sequence that affect TABF can be performed to determine which modifications do not substantially affect the TABF By way of example, a modification does not substantially affect a TABF when the difference between the TABF value before the modification and the TABF value after modification is not above a set threshold (e.g. a threshold considered indicative for the specific biological system where the translocation occurs).

By way of example, given the MtTatC sequence and a desire to include cysteine residues so that cross-linking with other proteins can be achieved, sequences with various cysteine insertions can be tested to determine which modifications least affect the TABF.

TABF determinants can be modified by changing the model itself or by changing the primary structure of the protein modeled. The TABF determinants that affect the model can be adjusted in a number of ways including changing values of single TABFs determinants such as a specific temperature, changing the characteristics of the membrane, changing the dynamics of the lateral gate opening, changing the inserter, modifying the inserter, increasing or decreasing translation rate, or explicitly modeling translocation cofactors. All of these modifications can be performed in parallel in corresponding experimental methods. For example, changing the translation rate can be performed experimentally by adding cycloheximide to the biological system where the translocation occurs. The temperature of the biological system can be changed by inducing expression of a protein in an organism at different temperatures of the related growth media. TABF determinants that affect the primary structure can be modified by changing the sequence of the protein modeled. Changes in the sequence of a protein can be performed by inserting, deleting, or modifying segments of the sequence, e.g. in a laboratory setting by modifying the sequence using any of a number of cloning or PCR based methods suitable for use by a skilled person. Therefore, many of the changes to TABF determinants performed in the model can be emulated experimentally. This allows the information derived from the simulations to be directly applied to a physical experiment. Using the information will allow for the TABFs observed using the model to be achieved experimentally.

Figure 29:
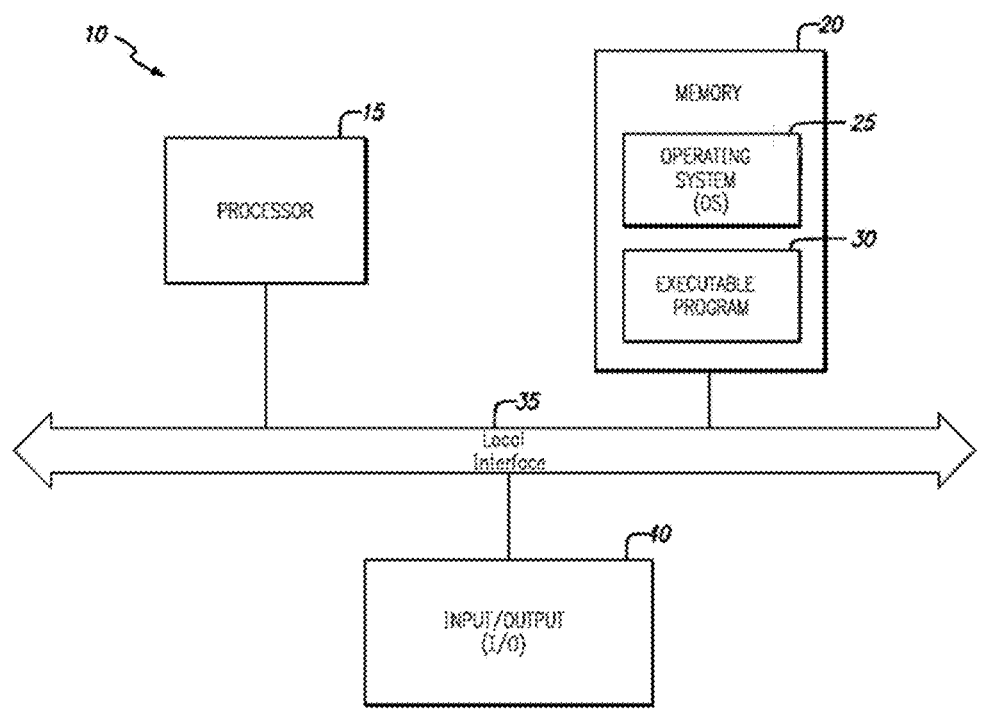

FIG. 29 shows a computer system (10) that may be used to implement the various computational embodiments described herein. It should be understood that certain elements may be additionally incorporated into computer system (10) and that the figure only shows certain basic elements (illustrated in the form of functional blocks). These functional blocks include a processor (15), memory (20), and one or more input and/or output (I/O) devices (40) (or peripherals) that are communicatively coupled via a local interface (35). The local interface (35) can be, for example, metal tracks on a printed circuit board, or any other forms of wired, wireless, and/or optical connection media. Furthermore, the local interface (35) is a symbolic representation of several elements such as controllers, buffers (caches), drivers, repeaters, and receivers that are generally directed at providing address, control, and/or data connections between multiple elements.

The processor (15) is a hardware device for executing software, more particularly, software stored in memory (20). The processor (15) can be any commercially available processor or a custom-built device. Examples of suitable commercially available microprocessors include processors manufactured by companies such as Intel, AMD, and Motorola.

The memory (20) can include any type of one or more volatile memory elements (e.g., random access memory (RAM, such as DRAM, SRAM, SDRAM, etc.)) and nonvolatile memory elements (e.g., ROM, hard drive, tape, CDROM, etc.). The memory elements may incorporate electronic, magnetic, optical, and/or other types of storage technology. It must be understood that the memory (20) can be implemented as a single device or as a number of devices arranged in a distributed structure, wherein various memory components are situated remote from one another, but each accessible, directly or indirectly, by the processor (15).

The software in memory (20) may include one or more separate programs, each of which comprises an ordered listing of executable instructions for implementing logical functions. In the example of FIG. 11, the software in the memory (20) includes an executable program (30) that can be executed to implement the translocon-associated protein trajectory simulations in accordance with the present disclosure. Memory (20) further includes a suitable operating system (OS) (25). The OS (25) can be an operating system that is used in various types of commercially-available devices such as, for example, a personal computer running a Windows® OS, an Apple® product running an Apple-related OS, or an Android OS running in a smart phone. The operating system (20) essentially controls the execution of executable program (30) and also the execution of other computer programs, such as those providing scheduling, input-output control, file and data management, memory management, and communication control and related services.

Executable program (30) is a source program, executable program (object code), script, or any other entity comprising a set of instructions to be executed in order to perform a functionality. When a source program, then the program may be translated via a compiler, assembler, interpreter, or the like, and may or may not also be included within the memory (20), so as to operate properly in connection with the OS (25).

The I/O devices (40) may include input devices, for example but not limited to, a keyboard, mouse, scanner, microphone, etc. Furthermore, the I/O devices (40) may also include output devices, for example but not limited to, a printer and/or a display. Finally, the I/O devices (40) may further include devices that communicate both inputs and outputs, for instance but not limited to, a modulator/demodulator (modem; for accessing another device, system, or network), a radio frequency (RF) or other transceiver, a telephonic interface, a bridge, a router, etc.

If the computer system (10) is a PC, workstation, or the like, the software in the memory (20) may further include a basic input output system (BIOS) (omitted for simplicity). The BIOS is a set of essential software routines that initialize and test hardware at startup, start the OS (25), and support the transfer of data among the hardware devices. The BIOS is stored in ROM so that the BIOS can be executed when the computer system (10) is activated.

When the computer system (10) is in operation, the processor (15) is configured to execute software stored within the memory (20), to communicate data to and from the memory (20), and to generally control operations of the computer system (10) pursuant to the software. The audio data spread spectrum embedding and detection system and the OS (25), in whole or in part, but typically the latter, are read by the processor (15), perhaps buffered within the processor (15), and then executed.

When the various embodiments described herein are implemented in software, it should be noted that the software can be stored on any computer readable storage medium for use by, or in connection with, any computer related system or method. In the context of this document, a computer readable storage medium is an electronic, magnetic, optical, or other physical device or means that can contain or store a computer program for use by, or in connection with, a computer related system or method.

The various embodiments described herein can be embodied in any computer-readable storage medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable storage medium" can be any non-transitory tangible means that can store, communicate, propagate, or transport the program for use by or in connection with the instruction execution system, apparatus, or device. The computer readable storage medium can be, for example but not limited to, an electronic, magnetic, optical, electromagnetic, infrared, or semiconductor system, apparatus, or device. More specific examples (a non-exhaustive list) of the computer-readable storage medium would include the following: a portable computer diskette, a random access memory (RAM), a read-only memory (ROM), an erasable programmable read-only memory (EPROM, EEPROM, or Flash memory) an optical disk such as a DVD or a CD.

In an alternative embodiment, where the various embodiments described herein are implemented in hardware, the hardware can implemented with any one, or a combination, of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The translocon associated protein trajectory simulations in accordance with the present disclosure have been performed on a variety of systems, including iMac® desktop machines, the Paso® system at Caltech, and the Hopper® and Carver® systems at the National Energy Research Supercomputing Center (NERSC).

In particular, Paso® is a cluster of 64 rack-mounted compute nodes with dual, quad-core 2.6 GHz Xeon Intel processors and 12 GB of memory per node. The nodes are connected via Gigabit Ethernet® and Infiniband®, with 9.6 TB of disk space. Hopper® is a peta-flop system, a Cray XE6®, with a peak performance of 1.28 Petaflops/sec, 153,216 compute cores for running scientific applications, 217 Terabytes of memory, and 2 Petabytes of online disk storage. Carver® is a liquid-cooled IBM iDataPlex system, having 1202 compute nodes (9,984 processor cores). This represents a theoretical peak performance of 106.5 Teraflops/sec. The above node count includes hardware that is dedicated to various strategic projects and experimental testbeds (e.g., Hadoop). As such, not all 1202 nodes will be available to all users at all times. All nodes are interconnected by 4×QDR InfiniBand® technology, providing 32 Gb/s of point-to-point bandwidth for high-performance message passing and I/O.

The translocon-associated protein trajectories can be, for example, generated using the code "TAPTgenerator" that is written in the FORTRAN90® programming language and that was fully written by the inventors. The "TAPTgenerator" code is comprised of a series of subroutines that evaluate the forces among the CG beads, evolve the positions of CG beads among subsequent timesteps of the translocon associated protein trajectory, describe the initialization and growth of the nascent chain from the exit channel of the protein inserter, and describe the opening/closing of the translocon lateral gate at each timestep in the trajectory.

An additional software component that can be used as part of the present disclosure is a script written in the Python programming language that performs the following analysis of the generated translocon associated protein trajectories: (1) Identification of the transmembrane segments of integral membrane proteins from the position of the nascent protein position along the trajectory; (2) Identification of the soluble loops of integral membrane proteins from the position of the nascent protein position along the trajectory; soluble loops are categorized as being positioned on the cytosolic side of the membrane, the lumenal side of the membrane, or in the interior of the membrane; (3) Identification whether and at what times a transmembrane segment underwent topology flipping (from Type II to Type III orientation) during the course of the generated trajectory; (4) Identification whether a given protein segment underwent "integration" vs. "secretion" vs. "retention".

A further software component that can be used as part of the present disclosure is a script written in the Python® programming language that translates a specific amino acid sequence into a sequence of CG beads. The CG beads so obtained are then simulated in the translocon associated protein trajectories.

In some embodiments, the model herein described can be used in methods and systems to provide a protein expressed through a co-translational translocation pathway with a set targeting and/or topology. In those embodiments computer generated trajectories can be obtained for one or candidate proteins and the related targeting and/or topologies relative to the translocon-nascent protein-ribosome system can be determined based on the kinetic pathways defined by the trajectories. The determined at least one targeting and/or topology for each of the one or more candidate proteins can be compared with the set targeting and/or topology to select a candidate protein among the one or more candidate proteins having the set targeting and/or topology. At least one targeting and/or topogenic determinant of the -translocon-nascent protein-ribosome system associated to the set targeting and/or topology for the protein based on the comparing can then be selected to produce the protein with the selected targeting and/or topology. In particular the protein can be produced by expressing the selected candidate through a co-translational translocation pathway with the selected at least one targeting and/or topogenic determinant of the -translocon-nascent protein-ribosome system.

Further effects and characteristics of the present disclosure will become more apparent hereinafter from the following detailed disclosure by way or illustration only with reference to an experimental section.

EXAMPLES

The methods and system herein described are further illustrated in the following examples, which are provided by way of illustration and are not intended to be limiting.

In particular, in the following examples a further a description of the methods and systems of the present disclosure and related engineered protein is provided with reference to TaTc protein, i.e. a protein expressed through a cotranslational translocation pathway which is a membrane protein. A person skilled in the art will appreciate the applicability of the features described in detail for TatC other membrane proteins and to other proteins expressed by way of a cotranslational translocation pathway. In particular, a skilled person reading the present disclosure will appreciate that TaTC is only one exemplary protein expressed through a cotranslational translocation pathway and that proteins expressed through a cotranslational translocation pathway can include other membrane proteins as well as additional proteins expressed through a cotranslational translocation pathway, such as proteins that are secretory, membrane-bound, or reside in the endoplasmic reticulum (ER), golgi or endosomes.

In the following examples, exemplary uses of the model herein described are provided with reference to TatC, a component of the bacterial twin-arginine translocase (6) and related chimeras. In particular correct targeting of TatC and related correlation with degree of expression in was simulated and verified experimentally according to exemplary steps of methods and systems of embodiments herein described.

Accordingly, the protocols and procedures utilized in the following examples provide exemplary procedures for a method for controlling the targeting herein described is further described and demonstrated with reference to exemplary embodiments where the protein is provided by TatC and related chimeras.

The protocols and procedures utilized in the following examples also provide exemplary procedures for a method to provide a protein expressed through a co-translational translocation pathway with a set targeting and/or topology, wherein the protein is provided by TatC, and the set targeting and/or topology is provided by a correct integration and folding within the cell membrane and wherein the TatC chimeras con provide related candidate proteins in accordance with mebodiments herein described as will be apparent to a skilled person.

The protocols and procedures utilized in the following examples further provide exemplary procedures for a method to engineer a protein expressed through a co-translational translocation pathway to obtain an engineered protein with a set targeting and/or topology wherein the protein is provided by TatC and the set targeting and/or topology is provided by a correct integration and folding within the cell membrane.

The following examples also provide further provide exemplary engineered proteins expressed through a co-translational translocation pathway with a set targeting and/or topology, wherein the protein is provided by TatC and the engineered proteins can be provided by the TatC chimeras.

Example 1: Cloning of TatC Constructs

In general, the PIPE cloning protocol was used (1). In short, TatC homologs wild type and chimeras were PCR amplified with the following primers:
AaTatc_PIPE-for (5'-GGTGAAAACCTGTACTTCCA-GAGCATGCCACTGACCGAACACC-3') (SEQ ID. NO: 12) AaTatc_PIPE-rev (5'-TGGTCCCTGAAACAAGACT-TCCAAAGCCTTCTGAATCTCCTTCTTTTTGC) (SEQ ID. NO:13) MtTatC_PIPE-for (5'-GGTGAAAACCTG-TACTTCCAGAGCTCTCTCGTAGACCACCTCAC-3') (SEQ ID. NO: 14) MtTatC_PIPE-rev (5'-TGGTCCCT-GAAACAAGACTTCCAAGTGAACACGCGCGATCTG-3') (SEQ ID. NO: 15).

The pETKat vectors were PCR amplified with vector PIPE-for (5'-TTGGAAGTCTTGTTTCAGGGACCA-3') (SEQ ID. NO: 16) and vector PIPE-rev (5'-GCTCTG-GAAGTACAGGTTTTCACC-3') (SEQ ID. NO: 17). 1-2 µl of insert and vector were combined on ice and 50 µl NovaBlue (Invitrogen) competent cells were added. PIPE cloning compatible vectors were generated based on a pET-33 vector (Novagen) containing a N-terminal 9× His-tag (pETKatN9) or a C terminal GFP and 8× His-tag (pETKatGFP). For better cloning efficacy a suicide cassette was also included, derived from pDest53 (Invitrogen). The TEV and 3C protease recognition sequences as PIPE cloning sites (vector maps in fig. S1A) was chosen.

Example 2: Designing and Cloning of TatC Chimeras

Figure 11C:
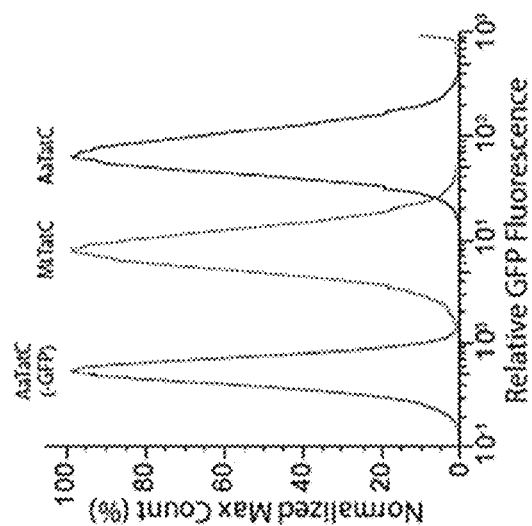
FIGS. 11A-11E show schematics and chats illustrating expression test and chimera definition.
Figure 11B:
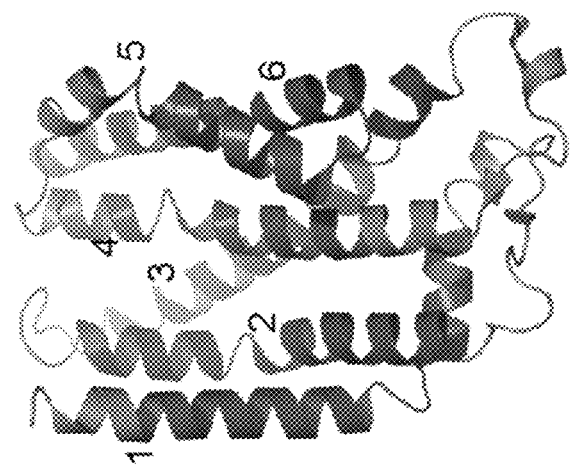
Figure 11A:
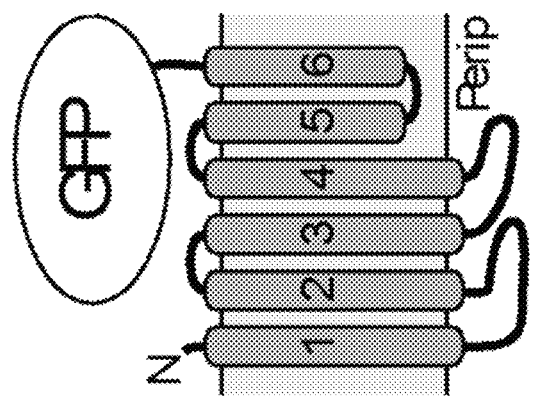
Figure 18A:
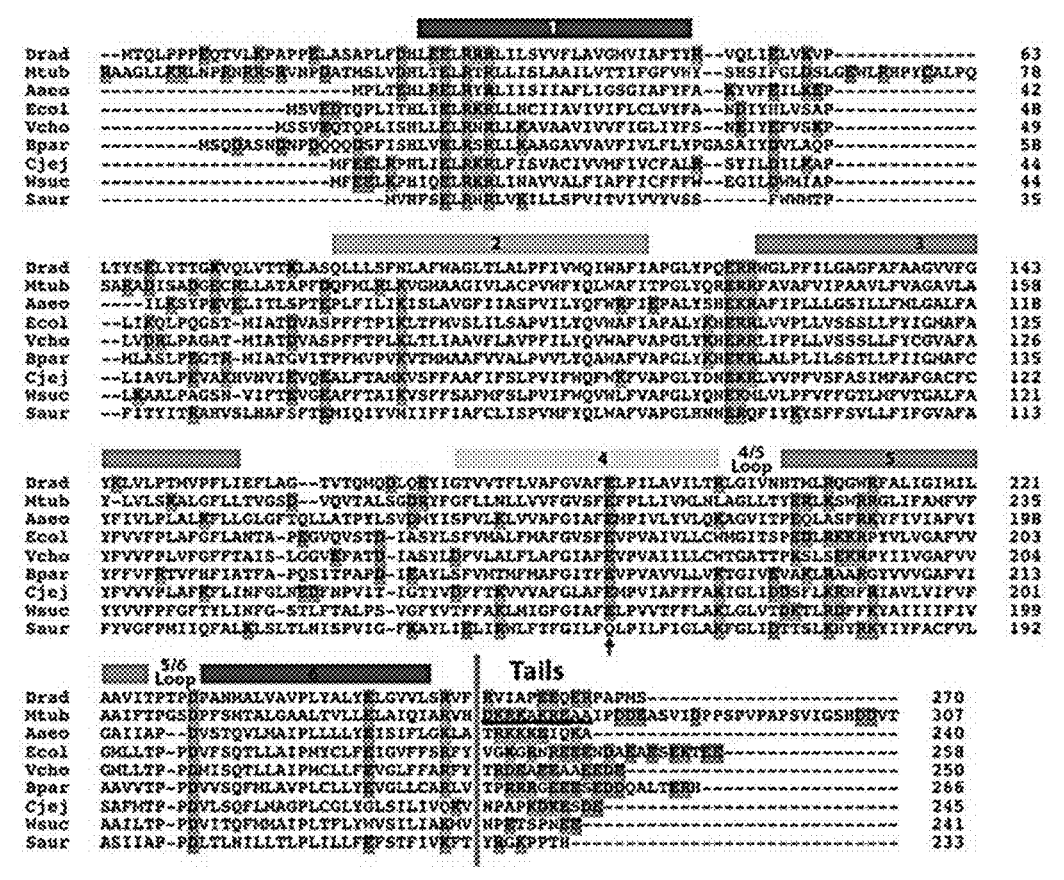
Figures 18B, 18C:
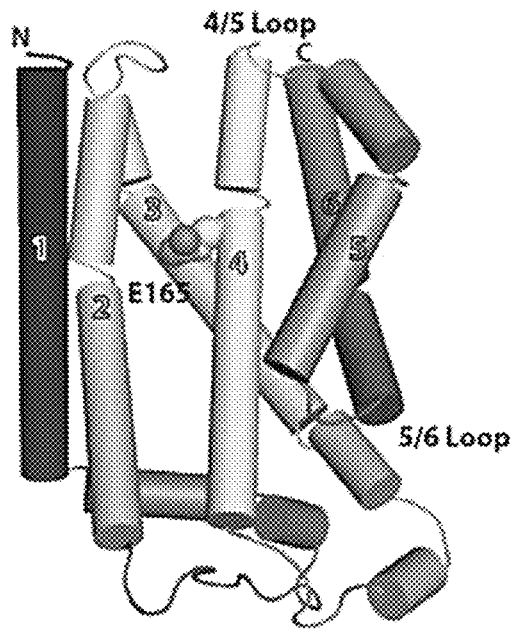

The wild type *M. tuberculosis* and *A. aeolicus* TatC genes were synthesized by primer extension as applied in DNA-Works http://helixweb.nih.gov/dnaworks/(2). TMD prediction was performed with HMMTMM2.0 (3). For TMD swaps, topology prediction as well as conserved flanking residues were taken into consideration (FIG. 11C and FIG. 18A). All constructs were cloned into the pETKatGFP or pETKatN9 vector for further analysis.

Example 3: Flow Cytometry

Constructs were transformed into BL21 Gold cells (Agilent technologies) and transferred onto LB-Kan plates. The next morning colonies were combined into a 5 ml 2×YT medium. After determination of $OD_{600}$ values, 50 ml 2×YT cultures were inoculated to a starting $OD_{600}$ of 0.01. Cultures were grown in an orbital shaker at 37° C. until they reached an $OD_{600}$ of approximately 0.2. The temperature of the orbital shaker was then reduced to 16° C. Upon reaching an $OD_{600}$ of 0.4, IPTG was added to final concentration of 1 mM to induce expression. Cultures were grown over night and 500 µl of each culture was harvested and centrifuged. The pellet was washed 3 times with 2 ml PBS, before re-suspending in 2 ml of PBS and dispensing 200 µl of each into a 96 well plate. In addition, a 2× dilution of the sample buffer in PBS was performed and 200 µl of this was plated into the 96-well plate.

GFP expression per cell was quantified using a MAC-SQuantl0 Analyzer (Miltenyi, Auburn, Calif.). This flow cytometry measures forward scattering, side scattering and total fluorescence at 488 nm. Both scattering plots give indication of cell size (FIG. 12B). To avoid aggregates, which would give artificially high per cell fluorescence, the measured cells were 'gated' to remove significant size outliers. From the remaining cells, a histogram was generated based on the total number of cells at a given fluorescence demonstrating the overall distribution, which was generally a simple Gaussian (FIG. 12B). A mean fluorescence was calculated for the total population and this is the value used in subsequent plots. For each independent expression experiment, expression of GFP and AaTatC alone were also measured as controls. For each sample, more than 30,000 cells were counted per run at a rate of 1000 events per second. All experiments were done in triplicate. Data analysis was performed with FloJo Software (TreeStar, Ashland, Oreg.).

Example 4: Protein Expression and Purification

To investigate whether the TatC chimera proteins were folded correctly, protein expression and purification was performed as previously described using a N-terminal His-tag variant (Ramasamy 2013) (18). In short, the procedure described above was scaled up to four 1l cultures of selected constructs. Cells were harvested and 10 g of wet cell mass was resuspended in 100 ml buffer A (300 mM NaCl, 10% glycerol, and 50 mM Tris pH=7.5). After homogenization the cells were lysed in a microfluidizer. The remainder of the lysate was centrifuged in a JA-17 fixed angle rotor (Beckman-Coulter) at 11,000 rpm for 30 minutes. The supernatants were then subjected to 30 minutes of centrifugation at 204526.3 g. Next the pellet was resuspended in 50 ml buffer B (Buffer A+1% DDM and 30 mM imidazole) and incubated at 4° C. under gentle shaking for 1 h. The membrane extract was obtained by a final centrifugation run with conditions identical to those described above. The supernatants containing the solubilized IMPs were mixed with 0.5 ml of NiNTA (Qiagen), that had been equilibrated with buffer B, and incubated at 4° C. under gentle shaking for 1 h. NiNTA was then isolated by 5 min centrifugation at 700 g, and resuspended in 20 ml of Buffer C (Buffer A+30 mM imidazole+0.03% DDM) for removal of unbound protein. NiNTA was isolated again as described above and the IMPs were eluted by resuspending the NiNTA in 5 ml buffer D (Buffer A+300 mM imidazole+0.03% DDM). After a final centrifugation step (5 minutes at 700 g) the supernatants were concentrated to a final volume of 0.5 ml using Amicon Ultra-4 (Millipore) concentrator with a 30 kDa cutoff membrane. The concentrated sample was then injected onto a 30 ml Superdex 200 column (GE Healthcare).

Example 5: Statistics

Statistical analysis was performed with Prism Graph Pad 6. An unpaired, two-tailed student T-test was employed to compare two groups. A p-value equal or lower than 0.05 was deemed statistically significant. For analysis of differences in expression of the different tail/linker MtTatC constructs. A one-way ANOVA was employed followed by the Dunnett's test. All were compared to MtTatC.

Example 6: Description of Simulation Method

Modeling of integral membrane protein (IMP) integration in the current example was performed using a 2-dimensional embodiment of the simulation method for the direct simulation of co-translational protein translocation and membrane integration. Ribosomal translation and membrane integration of nascent proteins are thus simulated on the minute timescale, enabling direct comparison between theory and experiment.

Here, the method was applied to verify the effect of IMP sequence on the membrane integration of various TatC and YidC homologues. The simulation method is employed with only minor modifications from the method described in the initial part of the present description and in the paper *Long-Timescale Dynamics and Regulation of Sec-Facilitated Protein Translocation*, B. Zhang and T. F. Miller, Cell Reports 2, 927-937 and S1-S24, Oct. 25 2012, which paper is incorporated herein by reference in its entirety, all of which modifications are specified below.

As described above and in such paper, the simulation method explicitly describes the configurational dynamics of the nascent-protein chain, conformational gating in the Sec translocon, and the slow dynamics of ribosomal translation. The nascent chain is represented as a freely jointed chain of beads, where each bead represents 3 amino acids and has a diameter of 8 Å, the typical Kuhn length for polypeptide chains. Bonding interactions between neighboring beads are described using the finite extension nonlinear elastic (FENE) potential(Equation 1), short-ranged nonbonding interactions are modeled using the Lennard-Jones potential (Equation 2), electrostatic interactions are modeled using the Debye-Huckel potential (Equations 3-4), and solvent interactions are described using a position-dependent potential based on the water-membrane transfer free energy for each CG bead (Equations 5-6). All parameters are as described in the specifications, unless otherwise stated.

Figure 14A:
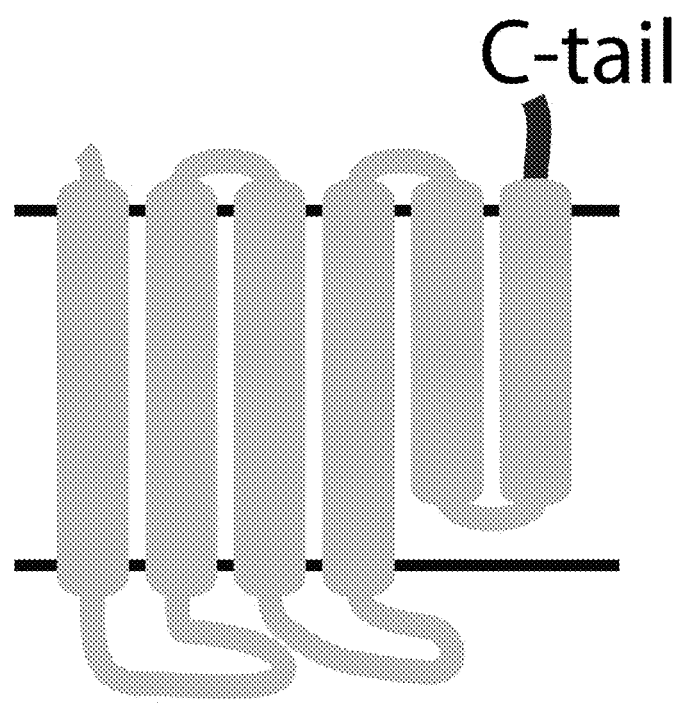
FIGS. 14A-14B show a diagram and charts illustrating expression using a simple tail swap. In particular.

The time evolution of the nascent protein is modeled using overdamped Brownian dynamics (Equation 7), with the CG beads confined to a two-dimensional plane that runs along the axis of the translocon channel and between the two helices of the lateral gate (LG). Conformational gating of the translocon LG is with the LG helices moving out of the plane of confinement for the CG beads, allowing the nascent chain to pass into the membrane bilayer. The rate of stochastic LG opening and closing is dependent on the sequence of the nascent protein CG beads that occupy the translocon channel (Equations 8-10). Ribosomal translation is directly simulated via growth of the nascent protein at the ribosome exit channel. Throughout translation, the C-terminus of the nascent protein is held fixed, and new beads are sequentially added at a rate of 24 residues per second. Upon completion of translation, the C-terminus is released from the ribosome, and the ribosome remains bound to the translocon. It has been confirmed by the inventors that the results herein are robust with respect to changes in the rate of ribosomal translation In the procedure reported in the present example, amino-acid sequences for the TatC homologs are mapped onto sequences of CG beads as follows. Each consecutive trio of amino acid residues in the nascent protein sequence is mapped to an associated CG bead. The water-membrane transfer free energy for each CG bead is taken to be the sum of the contributions from the individual amino acids; these values are taken from the experimental water-octanol transfer free energies for single residues. The charge for each CG bead is taken to be the sum of the contribution from the individual amino acids. As in the above mentioned paper, positively charged residues (Arginine and Lysine) were modeled with a +2 charge to capture significant effects on topology due to changes in the nascent protein. Histidine residues were modeled with only a +1 charge to account for the partial protonation of these residues, and negatively charged residues (Glutamate and Aspartate) were modeled with a change of −1. For the results in FIG. 16D, the charged residues appearing in the Aa-tail are scaled by a factor χ; all remaining charges in the protein sequence are left unaltered. This allowed us to isolate the effect of a specific TABF determinant, C-terminal charge, on the desired TABF, in this specific case the topology as shown in FIG. 14A.

Figure 27A:
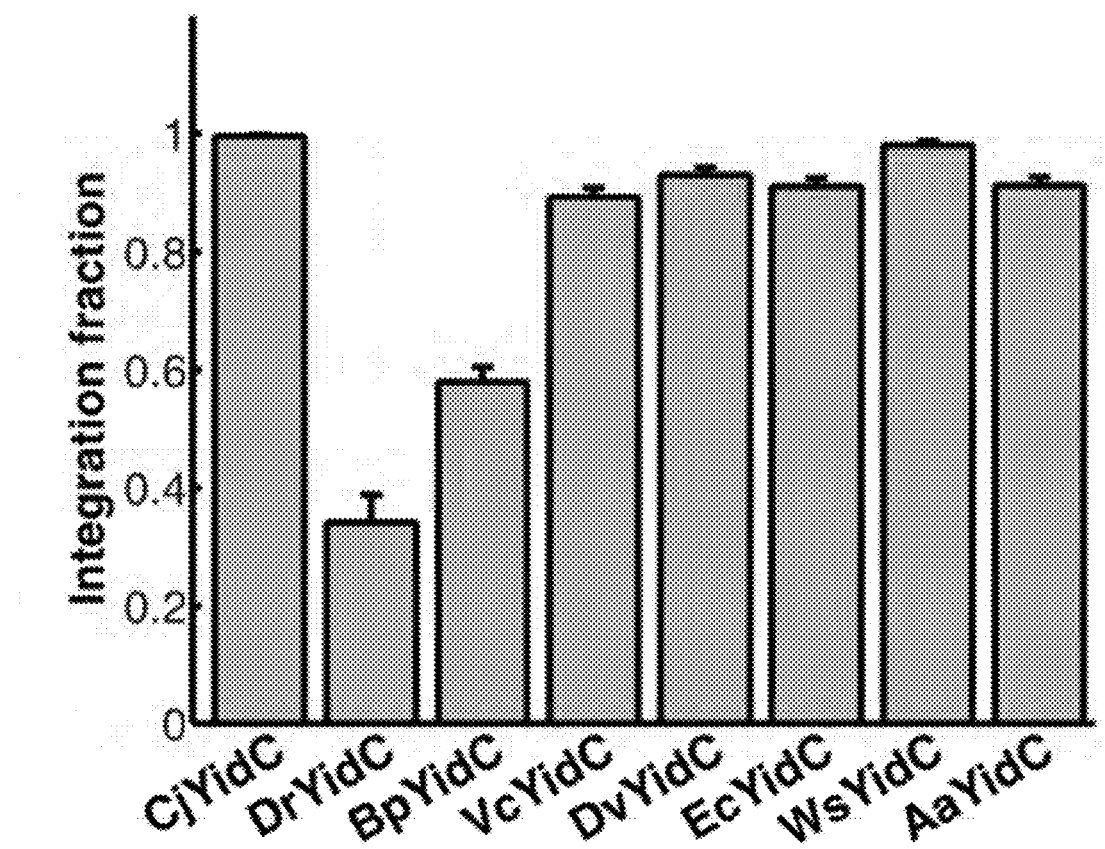
FIG. 27A shows an example application where the simulation method is used to screen an array of protein sequences, in this case homologs of the YidC protein. By comparing the final product as fully specified in the simulation trajectory to a desired TABF for 400 independent trajectories of each sequence a probability of observing the desired TABF is determined. It is observed that C with a same orientation one with respect to another. In particular some structural motifs (e.g. zinc fingers, a Greek key or helix-turn helix) are conserved in different proteins as will be understood by a skilled person.
Figure 27B:
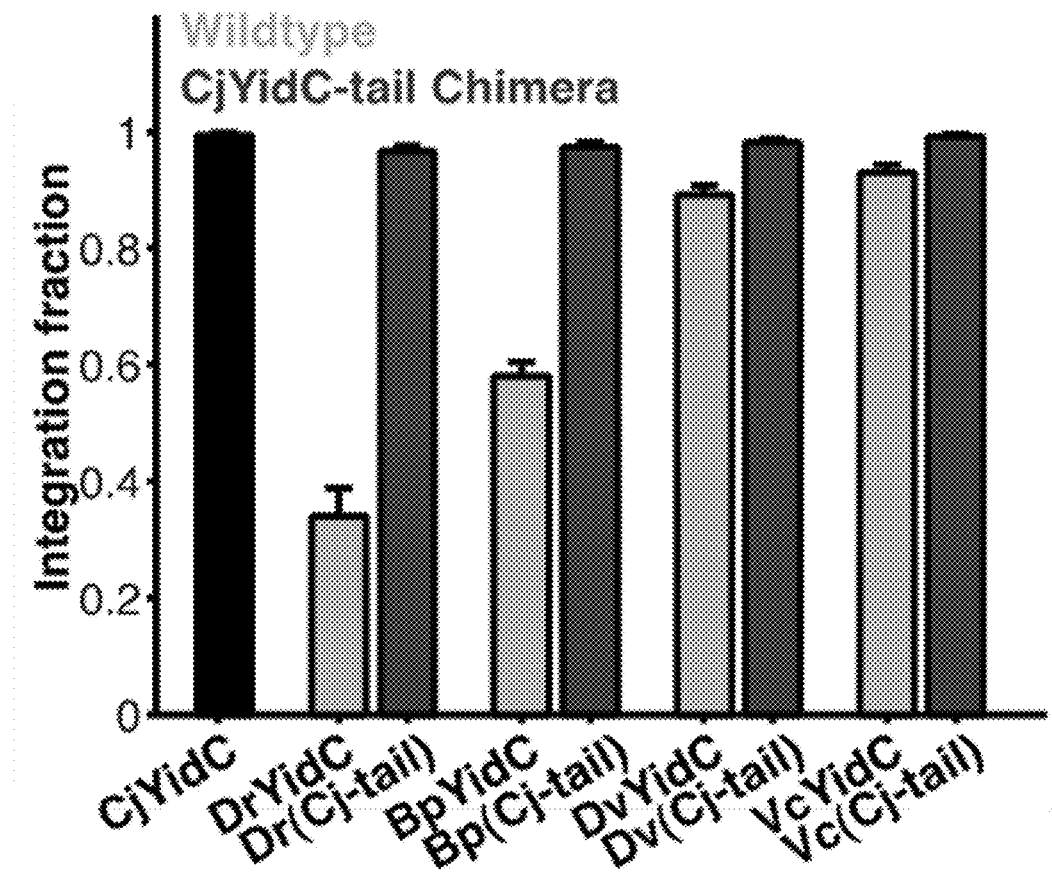

For the results in FIGS. 16A-C and FIG. 25, the co-translational membrane integration for each TatC sequence is simulated using 1200 independent CG trajectories. For the results in FIG. 17A and in all simulations involving YidC sequences (FIG. 27), each sequence is simulated using over 400 independent trajectories. As in the above reference each CG trajectory is performed with a timestep of 100 ns. All trajectories were terminated 30 s after the end of translation for the protein sequence. In this specific example 30 seconds was found to be the time it takes for translocon-associated biogenesis to complete.

To determine whether a given trajectory leads to correct integration of the TatC homolog in the correct multispanning topology, the following criteria were used. The topology of a nascent protein configuration is determined by the location of the soluble loops that connect the TMD. A collective variable $\lambda_i$ was defined for each loop, with i=1 corresponding to the loop that leads TMD 1 in the TatC sequence (i.e., the N-terminal sequence) and i=7 corresponding to the loop that follows TMD 6 (i.e., the C-tail). If loop i is in the cytosol, then $\lambda_i=1$; if loop i is in the periplasm, then $\lambda_i=-1$; otherwise, $\lambda_i=0$. The multi-spanning TatC topology corresponds to configurations for which $\lambda_i=1$ for i=1, 3, 5 and 7 and for which $\lambda_i=-1$ for i=2, 4, and 6. A given trajectory is determined to have reached correct IMP integration if a topology with the loops in the right orientation is sampled during a time window of 2.5 seconds taken 25 seconds after the end of translation, a time window was used to reduce noise due to loops temporarily entering the lipid membrane. The time window was taken 25 seconds after the end of translation, which was found sufficient to allow the nascent-protein to finish the integration/translocation of TMD 6.

The simulations revealed that only the integration of the final TMD was affected by sequence modifications in the C-terminal loop (FIGS. 25B-G). In sequences where the wildtype protein showed a high probability for misintegration due to translocation of the C-terminal loop (FIG. 25A) introduction of the Aa-tail lead to improved retention of the C-terminus in the cytosol, and thus a higher probability for integration in the correct multi-spanning topology. When assessing the effect of the Aa-tail on integration it is thus sufficient to only consider the effect on the integration of the last TMD. Consistent with this observation, in FIG. 16 and FIG. 17A correct integration is defined as the nascent protein integrating in the $C_{cyt}$ topology, without assessing the topology of the preceding loops. By excluding distal loops in the analysis according to the present disclosure, a clearer signal can be obtained, while the effect of the C-tail sequence on integration is the qualitatively the same as when analyzing the full topology.

Example 7: TatC Insertion Efficiency Simulations for TatC Variants

To determine the TatC insertion efficiency simulations were conducted using the CG model of Example 6.

1200 independent CG trajectories were calculated for *Aquifex* aeolicus TatC (Aa), *Mycobacterium* turberculosis TatC (Mt), *Bordetella parapertussis* (Bp), *Campylobacter jejuni* (Cj), *Deinococcus radiodurans* (Dr), *Staphylococcus aureus* (Sa), *Vibrio cholera* (Vc), and *Wolinella succinogenes* (Ws), both with and without the replacement of the native tail with the Aa tail.

The results for the fraction of trajectories ending in the correct topology calculated for *Aquifex* aeolicus TatC (Aa), *Mycobacterium* turberculosis TatC (Mt), and *Mycobacterium* turberculosis TatC with an *Aquifex* aeolicus tail is shown in FIG. 16A. The integration fraction calculated using the simulation method shows a striking agreement with experimentally determined expression levels shown in FIG. 14B, thus providing a specific example where the simulation method was utilized to predict protein expression levels.

Figure 35:
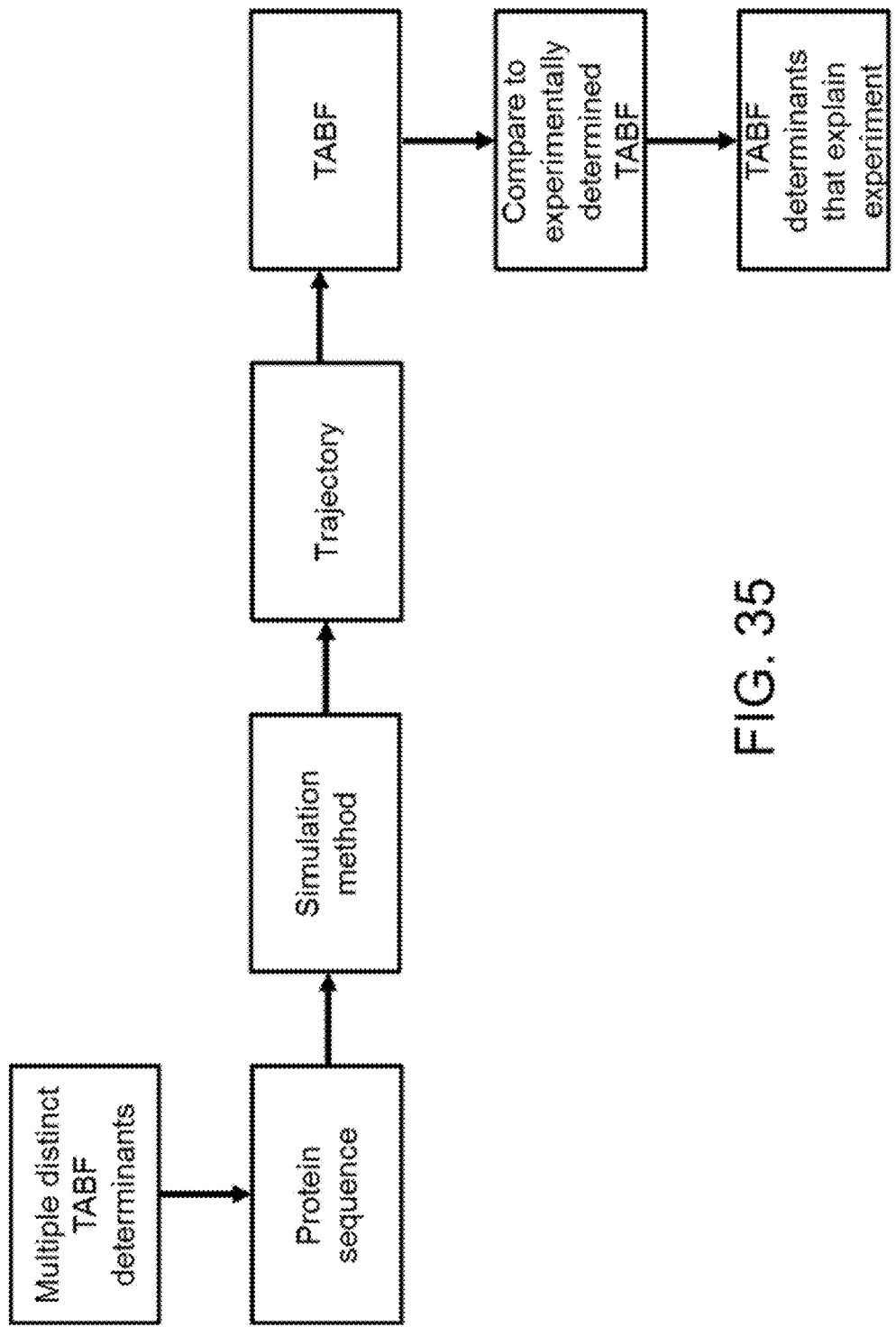
Figure 36:
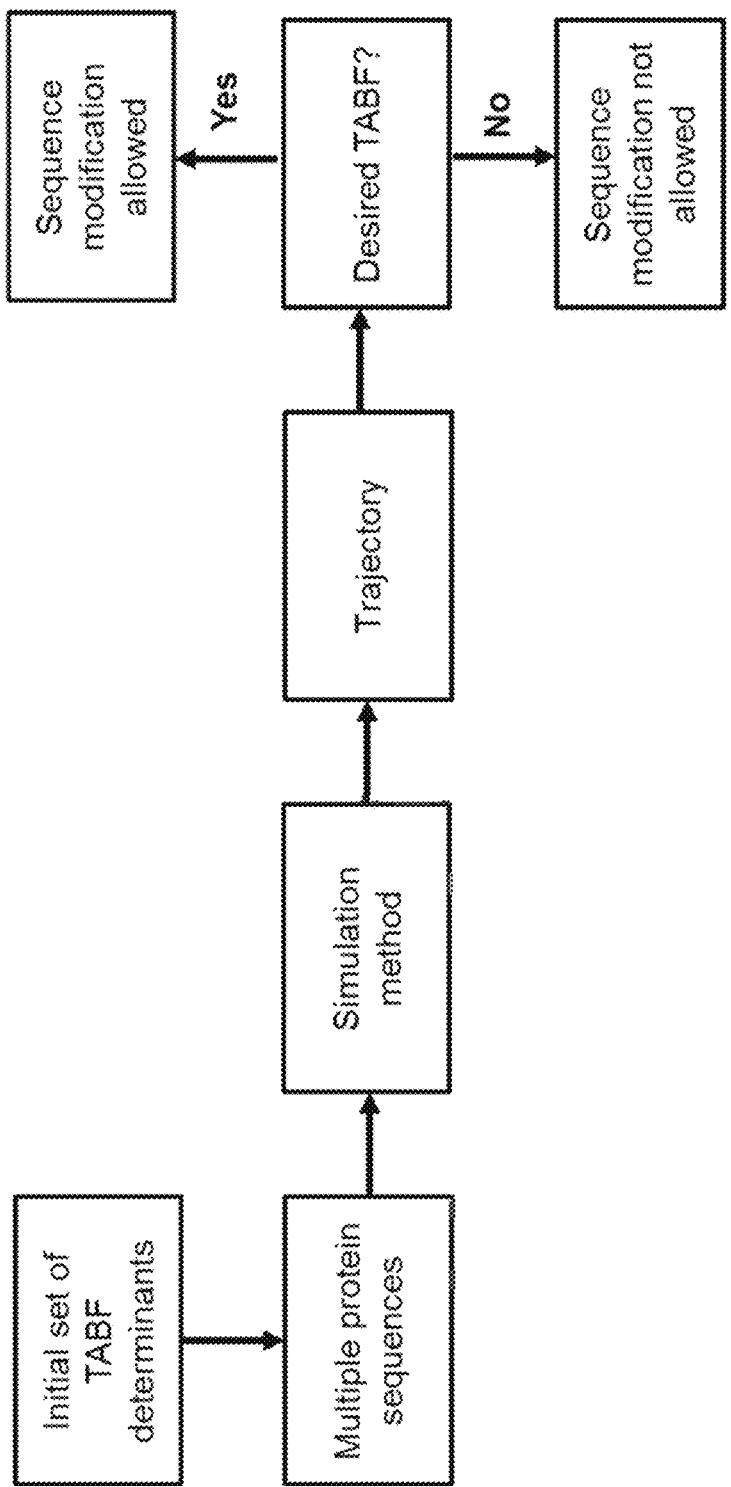

For TatCs from *Mycobacterium turberculosis* (Mt), *Bordetella parapertussis* (Bp), *Escherichia coli* (Ec), *Campylobacter jejuni* (Cj), *Deinococcus radiodurans* (Dr), *Staphylococcus aureus* (Sa), *Vibrio cholera* (Vc), and *Wolinella succinogenes* (Ws) with and without the replacement of the tail with the Aa-tail the fraction of simulations exhibiting the desired TABF, correct insertion of the TMDs in the topology shown in FIG. 14A, was calculated using the simulation method according to the present disclosure. The effect of the Aa-tail as a TABF determinant in these sequences was quantified by comparing the fraction of simulations exhibiting the desired TABF for a given sequence with and without the Aa-tail modification. For 6 out of 8 tested sequences the simulation method predicts that the Aa-tail can act as a TABF determinant that enhances the level of expression. This prediction agrees with experimental expression levels for all but the one of the tested TatCs, as shown in FIG. 16C, thus providing a specific example where the simulation method is able to identify a TABF determinant (as shown, for example, in the embodiment of FIG. 32) that can modulate protein expression levels., and providing an explanation for observed experimental data, as described, for example, in the embodiment shown in FIG. 35.

Figure 34:
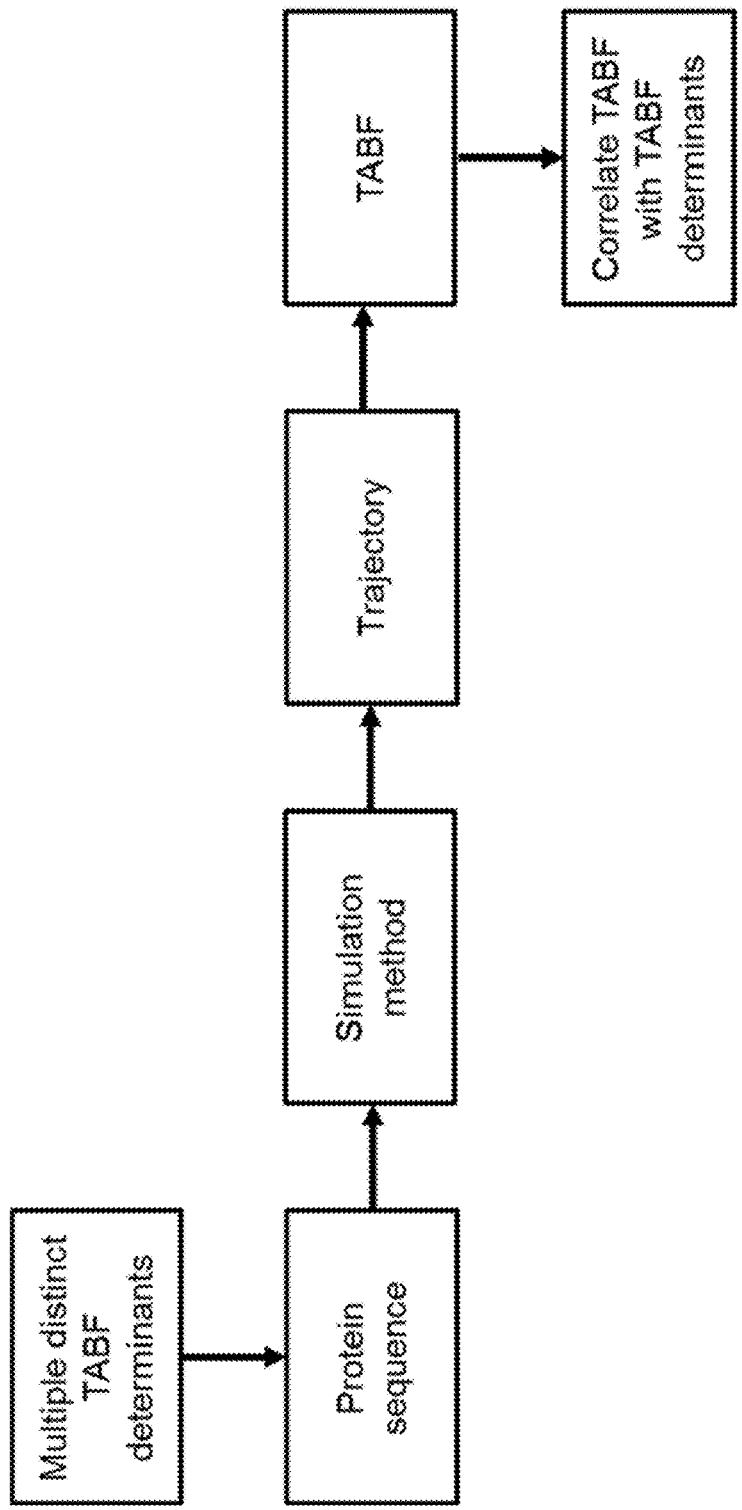

To identify the property of the Aa-tail sequence that acts as a TABF determinant in TatC further simulations were performed where the C-terminal charges were adjusted, leaving all other TABF determinants unchanged. This is similar to the embodiment shown schematically in FIG. 34. The results shown in FIG. 17A clearly identify the C-terminal charge as a TABF determinant. Scaling the charges in C-terminal residues directly correlates (R=0.98) with the fraction of desired TABF determined from the simulation trajectories. The C-terminal charge also correlates with experimentally observed expression levels, as shown in FIG. 17B, relating the experimentally observed expression levels to calculated TABFs.

Example 8: Cloning TatC Variants

In order to verify that the computations simulations can reasonably predict protein expression, TatCs from *Aquifex aeolicus* (Aa), *Mycobacterium turberculosis* (Mt), *Bordetella parapertussis* (Bp), *Campylobacter jejuni* (Cj), *Deinococcus radiodurans* (Dr), *Staphylococcus aureus* (Sa), *Vibrio cholera* (Vc), *Escherichia coli* (Ec), and *Wolinella succinogenes* (Ws), with and wihotu the native tail replaced with the Aa tail were cloned into the pETKatGFP expression constructs preceding the GFP domain. When thse constructs express the cloned gene with a TEV cleave site attached to the N-terminus and a 3C cleave site followed by an eGFP molecule and a 6×Histidine tag attached to the C-terminus.

In general, the PIPE cloning protocol was used (1). In short, TatC homologs wild type and chimeras were PCR amplified with the following primers: AaTatc_PIPE-for (SEQ ID. NO: 12); AaTatc_PIPE-rev (SEQ ID. NO: 13); MtTatC_PIPE-for (SEQ ID. NO: 14); and MtTatC_PIPE-rev (SEQ ID. NO: 15).

The pETKat vectors were PCR amplified with vector PIPE-for (SEQ ID. NO: 16) and vector PIPE-rev (SEQ ID. NO: 17). 1-2 µl of insert and vector were combined on ice and 50 µl NovaBlue (Invitrogen) competent cells were added. PIPE cloning compatible vectors.

The expression constructs used are based on a pET-33 vector (Novagen) containing a N-terminal 9× His-tag (pET-KatN9) or a C terminal GFP and 8× His-tag (pETKatGFP). For better cloning efficacy a suicide cassette was also included, derived from pDest53 (Invitrogen). TEV and 3C protease recognition sequences were chosen as PIPE cloning sites (vector maps in FIG. 12A).

Figure 12A:
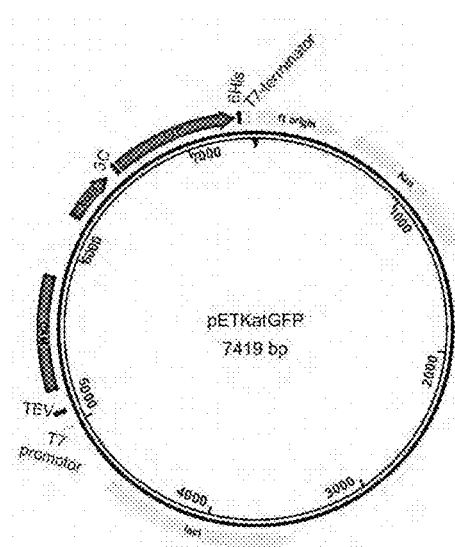
FIGS. 12A-12C show schematics and charts illustrating experimental set-up for expression tests. In particular.
Figure 12B:
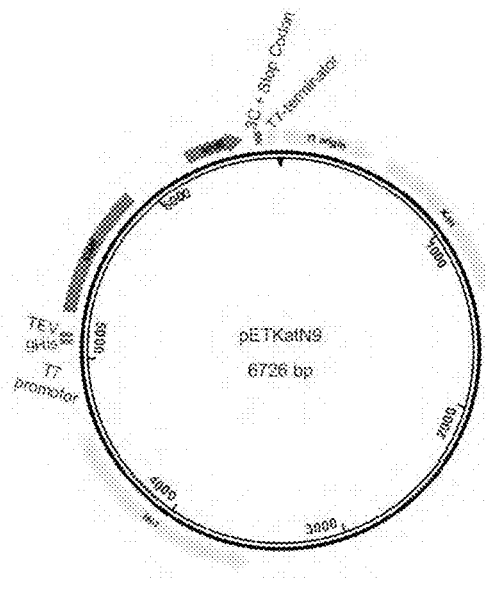

A map of pETKatGFP, a PIPE cloning vector based on pET33 can be seen in FIG. 12A. Parts that are modified from the original vector are highlighted in dark gray. The multiple cloning site was replaced by a chloramphenicol resistance gene and the suicide gene ccdB, which are flanked by TEV and 3C protease sites to allow for common primers to clone into each vector. Immediately after the 3C site is the gfp gene with an octa-histidine tag.

A map of pETKatN9, is shown in FIG. 12B, which is similar to pETKatGFP without the C-terminal GFP tag and a N-terminal nona-histidine tag instead.

The wild type *M. tuberculosis* and *A. aeolicus* TatC genes were synthesized by primer extension as applied in DNA-Works http://helixweb.nih.gov/dnaworks/. TMD prediction was performed with HMMTMM2.0. For TMD swaps, topology prediction as well as conserved flanking residues were taken into consideration (FIG. 11C and FIG. 18A). All constructs were cloned into the pETKatGFP or pETKatN9 vector for further analysis.

Sequencing results indicated successful integration of the TatC homologs into their respective vectors.

Example 9: Expression Analysis of TatC Variants

In order to verify the computational simulations ability to predict protein expression TatCs from *Aquifex aeolicus* (Aa), *Mycobacterium turberculosis* (Mt), *Bordetella parapertussis* (Bp), *Campylobacter jejuni* (Cj), *Deinococcus radiodurans* (Dr), *Staphylococcus aureus* (Sa), *Vibrio cholerae* (Vc), *Escherichia coli* (Ec), and *Wolinella succinogenes* (Ws) and their *Aquifex Aeolicus* tails swaps in the pETKat-GFP constructs and the *Aquifex* Aeolics Tatc and solube GFP in independent pETKatN9 constructs were expressed.

Constructs were transformed into BL21 Gold cells (Agilent Technologies) and transferred onto LB-Kan plates. The next morning colonies were combined into a 5 ml 2×YT medium.

After determination of OD600 values, 50 ml 2×YT cultures were inoculated to a starting OD600 of 0.01. Cultures were grown in an orbital shaker at 37° C. until they reached an OD600 of approximately 0.2. The temperature of the orbital shaker was then reduced to 16° C. Upon reaching an OD600 of 0.4, IPTG was added to final concentration of 1 mM to induce expression of the fusion proteins. Cultures were grown over night and 500 µl of each culture was harvested and centrifuged. The supernatant was discarded and the pellet was washed 3 times with 2 ml PBS, before re-suspending in 2 ml of PBS and dispensing 200 µl of each into a 96 well plate.

Figure 12C:
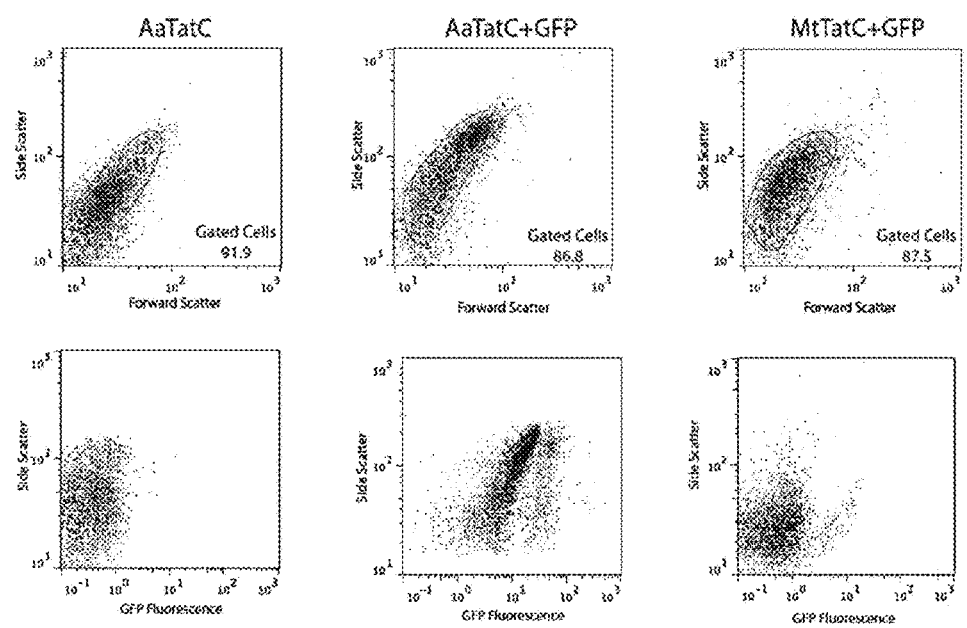
Figure 13A:
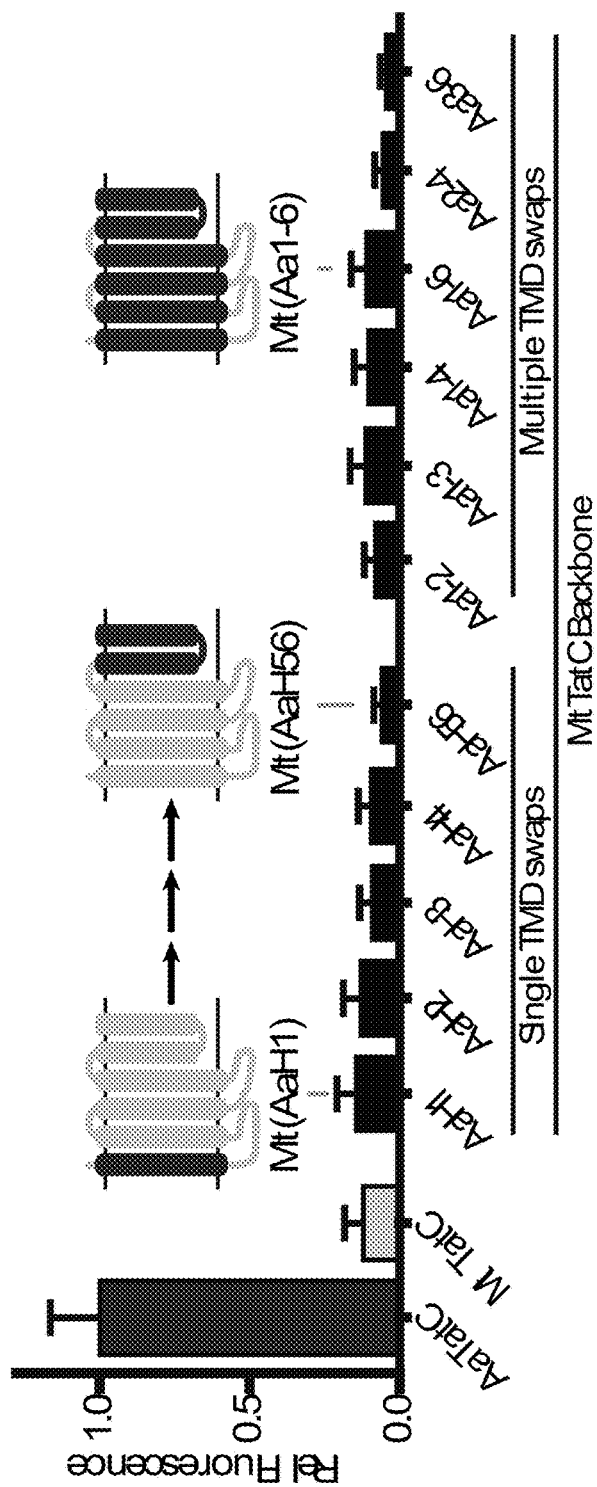
FIGS. 13A-13B show the relative expression for the experimentally tested AaTatC/MtTatC chimera proteins. In particular.
Figure 13B:
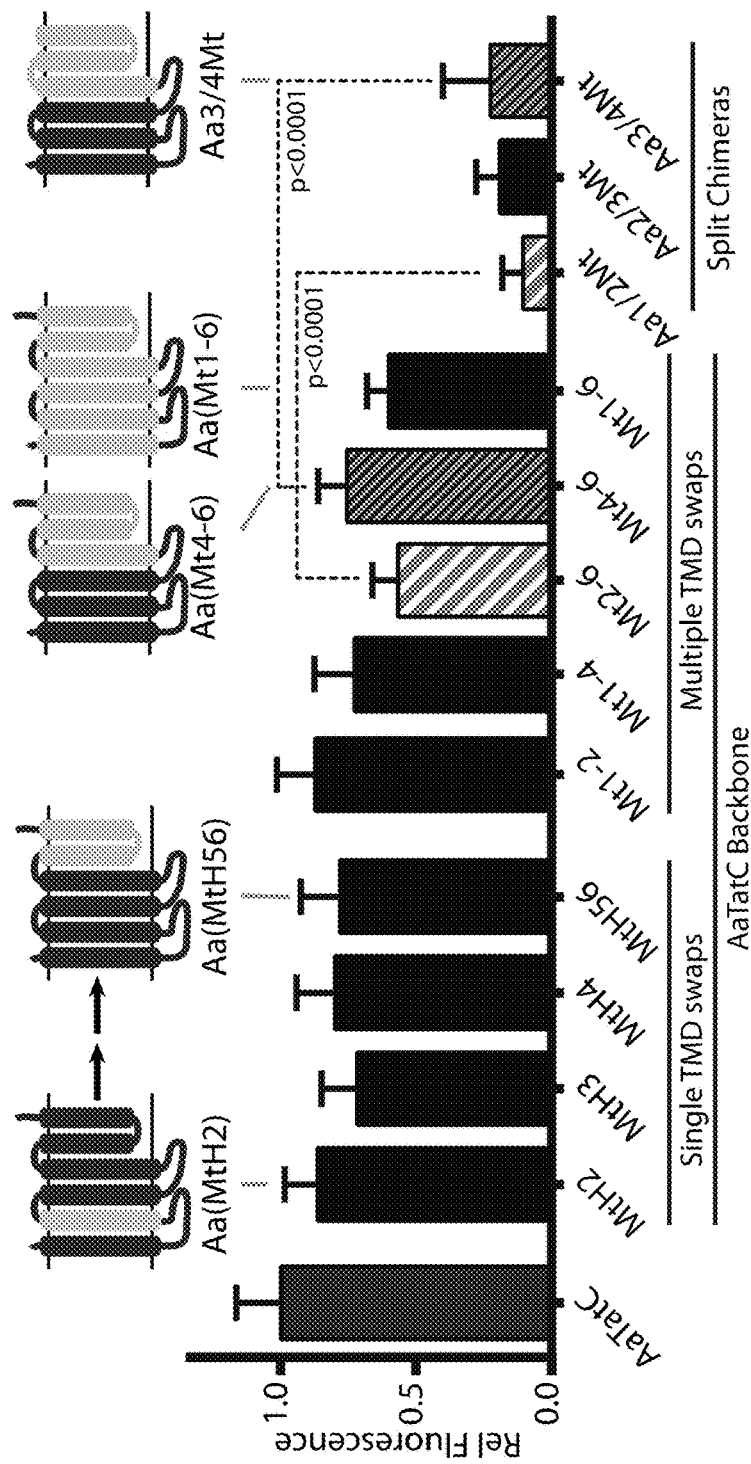

TatC-GFP fusion protein expression per cell was quantified using a MACSQuant10 Analyzer (Miltenyi, Auburn, Calif.) flow cytometer. This flow cytometer measures forward scattering, side scattering and fluorescence at 488 nm of particles passing through the detector. Both scattering plots give indication of cell size (FIG. 12C). The flow cytometer was calibrated to establish a trigger voltage such that only cells were recorded as individual event. The measured cells were 'gated' to remove significant size outliers. From the remaining cells, a histogram was generated based on the total number of cells at a given fluorescence and the logarithm of total cell fluorescence on the opposite axis, which generally displayed a Gaussian shape (FIG. 11C). The mean fluorescence intensity per cell was calculated for the total population. This value is shown in the plots that give fluorescence values. For each independent expression experiment, expression of soluble GFP and AaTatC alone were used as controls for high and low fluorescence, respectively. All experiments were perfomed in independent triplicates. These independent data points were used to establish standard deviations between replicate samples. Analysis of the flow cytometry data was performed with FloJo® Software (TreeStar, Ashland, Oreg.).

FIG. 12C shows representative flow cytometry results of AaTatC, AaTatC+GFP, and MtTatC+GFP. The top panel shows side scatter plotted versus forward scatter to give an indication of the size of the particles measured by the flow cytometer. The red lines indicate the gated region with cells outside this line excluded from the mean fluorescence measurements. The lower panel is a plot of side scatter versus GFP fluorescence.

Figures 11D, 11E:
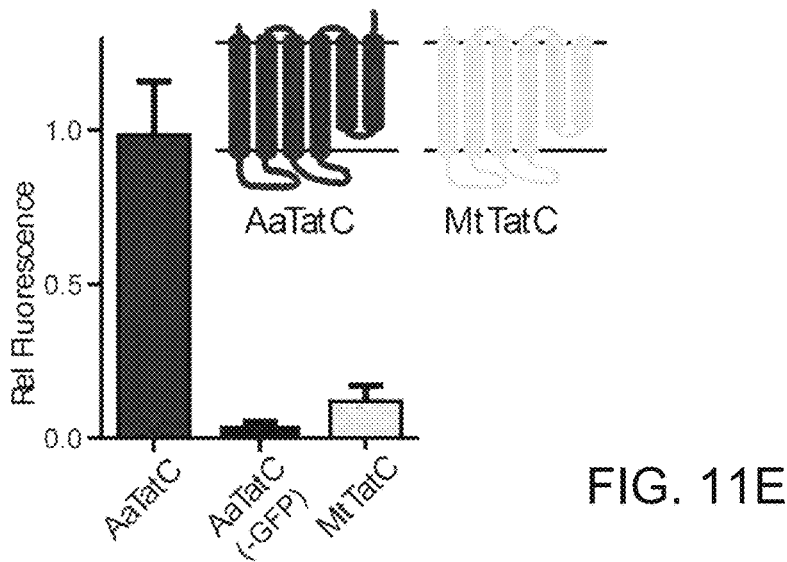
Figure 14B:
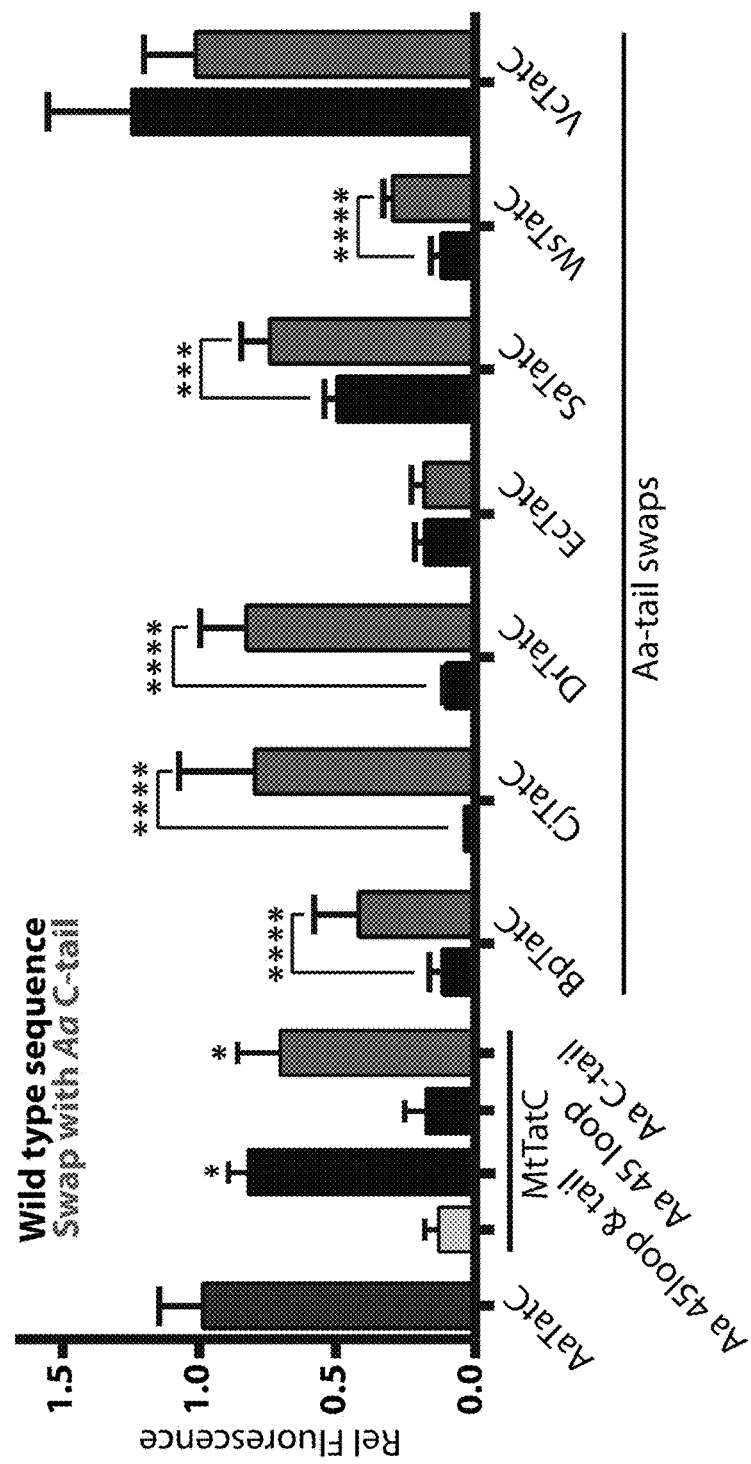
Figure 15:
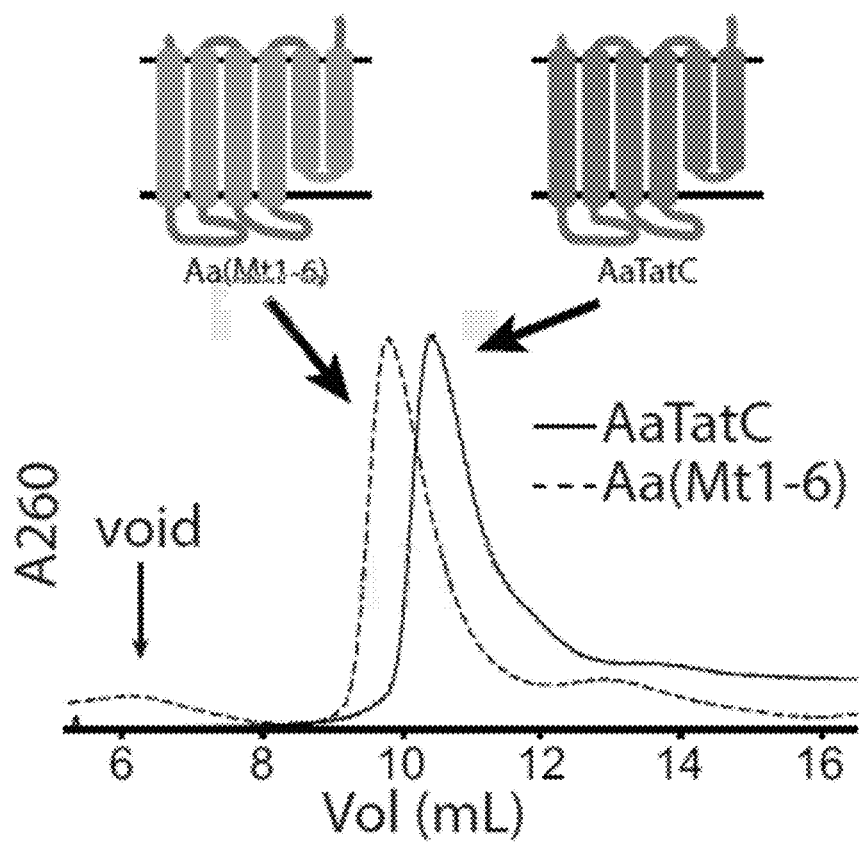
FIG. 15 shows a chart and diagram illustrating SEC of AaTatC and Aa(Mtl-6) Size-exclusion chromatograms of two separate runs for his-tagged AaTatC and the full swap chimera Aa(Mtl-6). The void volume is highlighted.

Expression tests comparing various TatC homologs with their native tail and with their tails replaced with the Aa tails are shown in FIG. 11E and FIG. 14B. An unpaired two-tailed student T-test was performed for genes with and without replacement of their tails with the Aa tail. Statistically significant differences are indicated by asterisks (* p=0.0003; ** p<0.0001), while no asterisk indicates no significant difference.

As shown in the expression tests various tail combinations and variants of TatC result in dramatically different expression.

Example 10: Analysis of Insertion Efficiency Simulations and Expression Analysis of TatC Variants Simulation results from the procedure of Example 7, and expression results from the experiments of Example 9 were compared.

The fraction of AaTatC, MtTatC, and Mt(Aa C-tail) simulation trajectories that yield the correct membrane topology, normalized with respect to the AaTatC wild type as shown in FIG. 16A. Comparison of the fraction of correct integration, determined by simulation, and the rate of experimentally observed expression was evaluated as shown in FIG. 16B. For each of the tested sequences, the relative expression levels of the homologs wild type and is plotted on the y-axis against the ratio for integration of the wild type and its C-tail swap chimera on the x-axis. The values, excluding the outlier for Vc, are fit by linear regression with a correlation (R) of 0.5. The fraction of Mt(Aa-tail) simulation trajectories that yield the desired membrane topology as a function of the charge on the tail is shown in FIG. 16D. The values are normalized with respect to theMt(Aa-tail) sequence without scaled charges. The values are fit by linear regression with a correlation (R) of 0.98. FIG. 16E shows the correlation of the ratio of expression of the TatC homologs with the tails replaced with the Aa tail relative to wild type Aa tail versus the charge magnitude of each homolog (see also FIG. 18C). The values are fit by linear regression with a correlation (R) of 0.88. Error bars are calculated from the standard error of the mean.

Figure 25A:
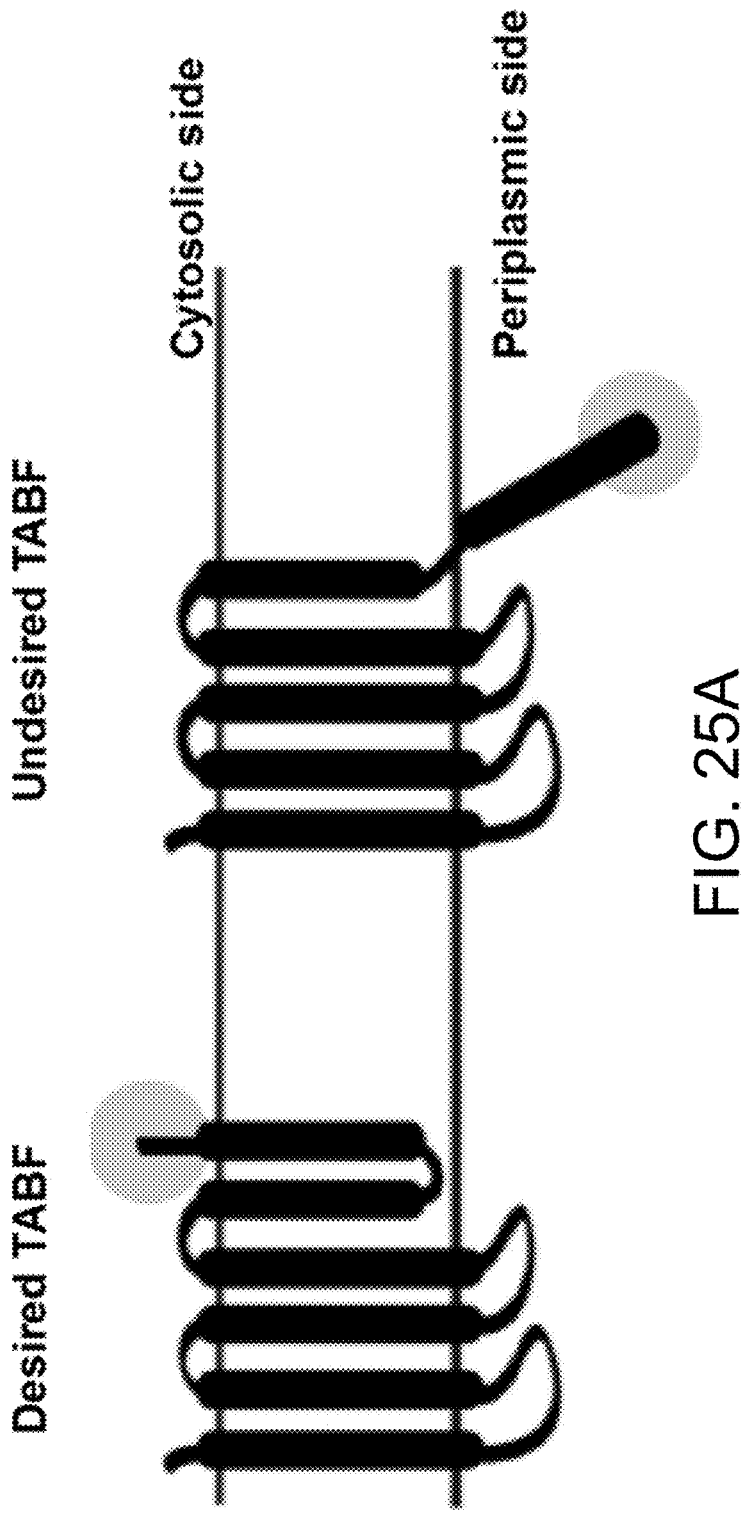
FIGS. 25A-25G provides an example for the claim that the simulation method can quantify the suitability of IMP loops as TABF determinants, and be used to design sequences with a higher yield of desired TABF.
Figure 25B:
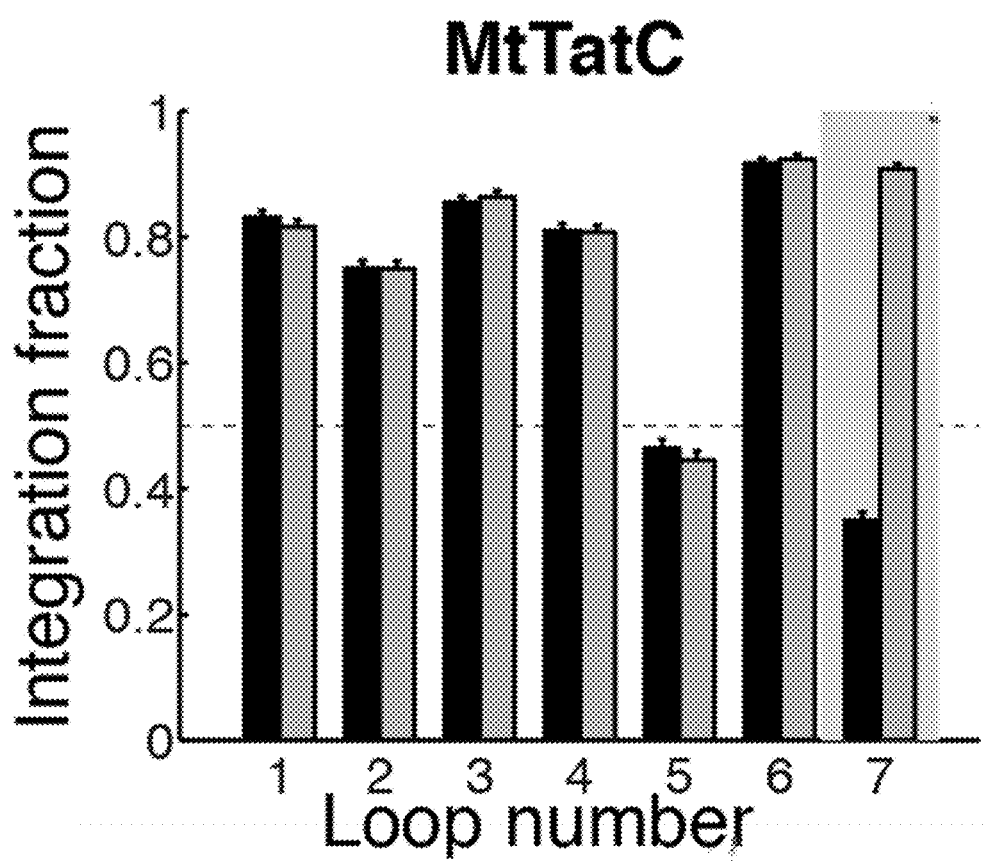
Figure 25C:
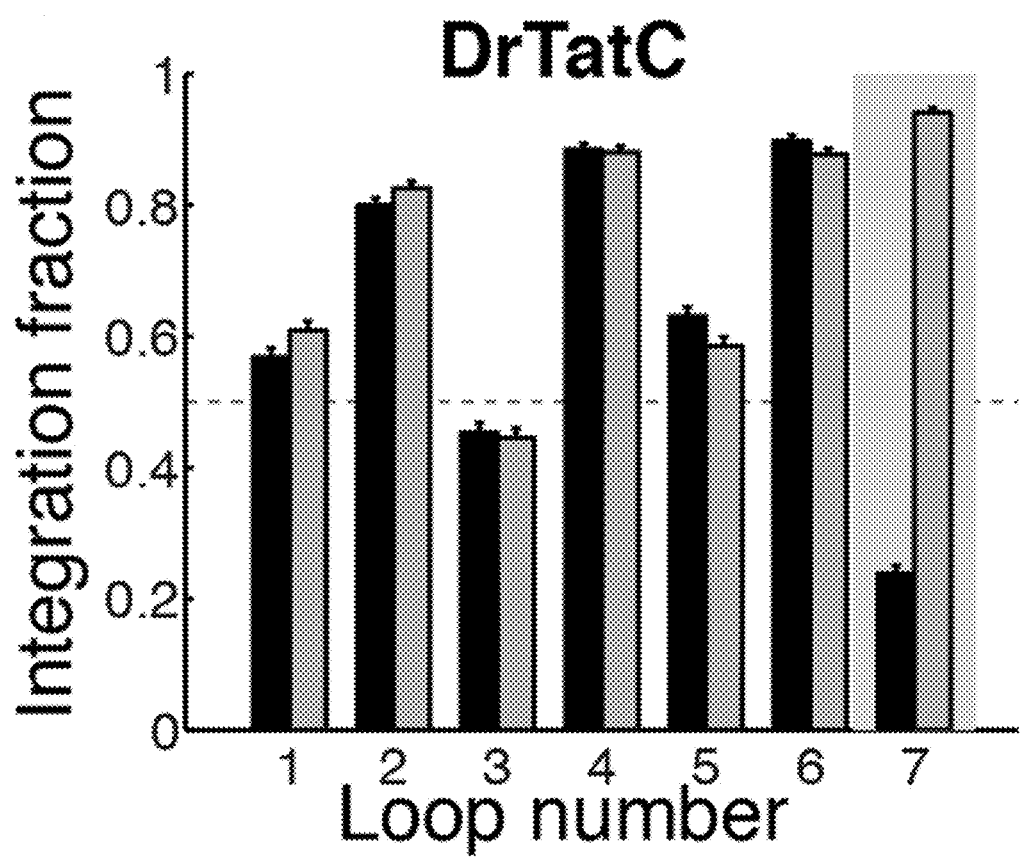
Figure 25D:
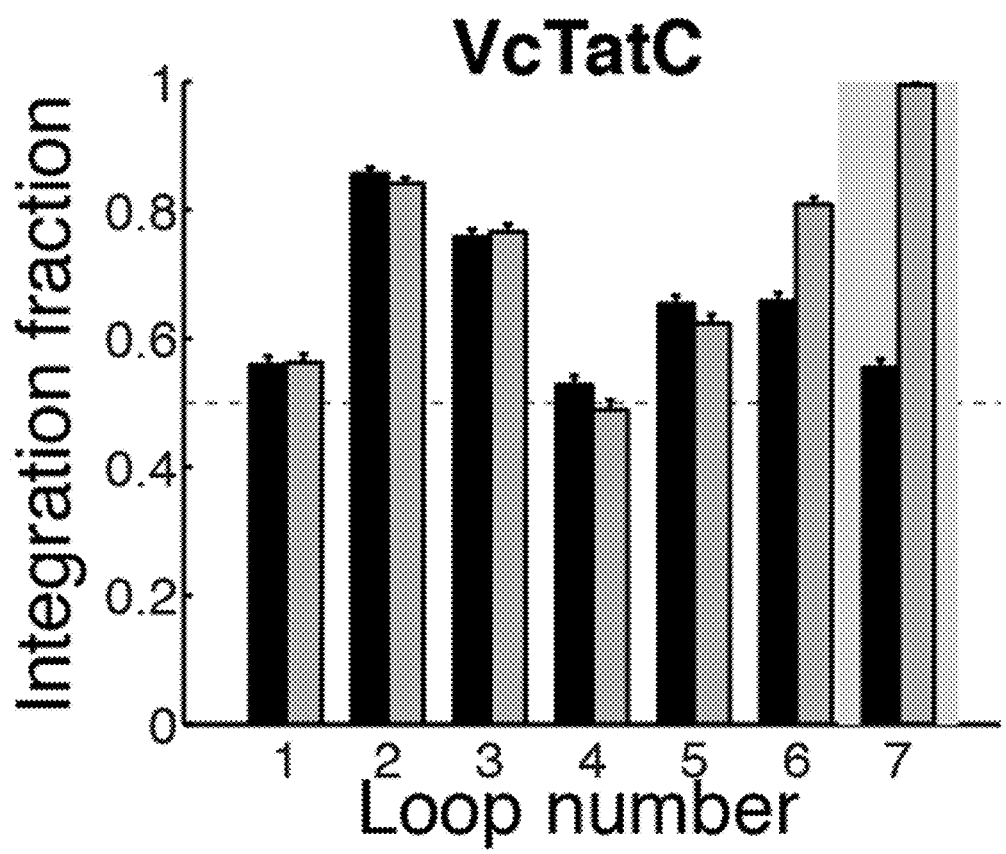
Figure 25E:
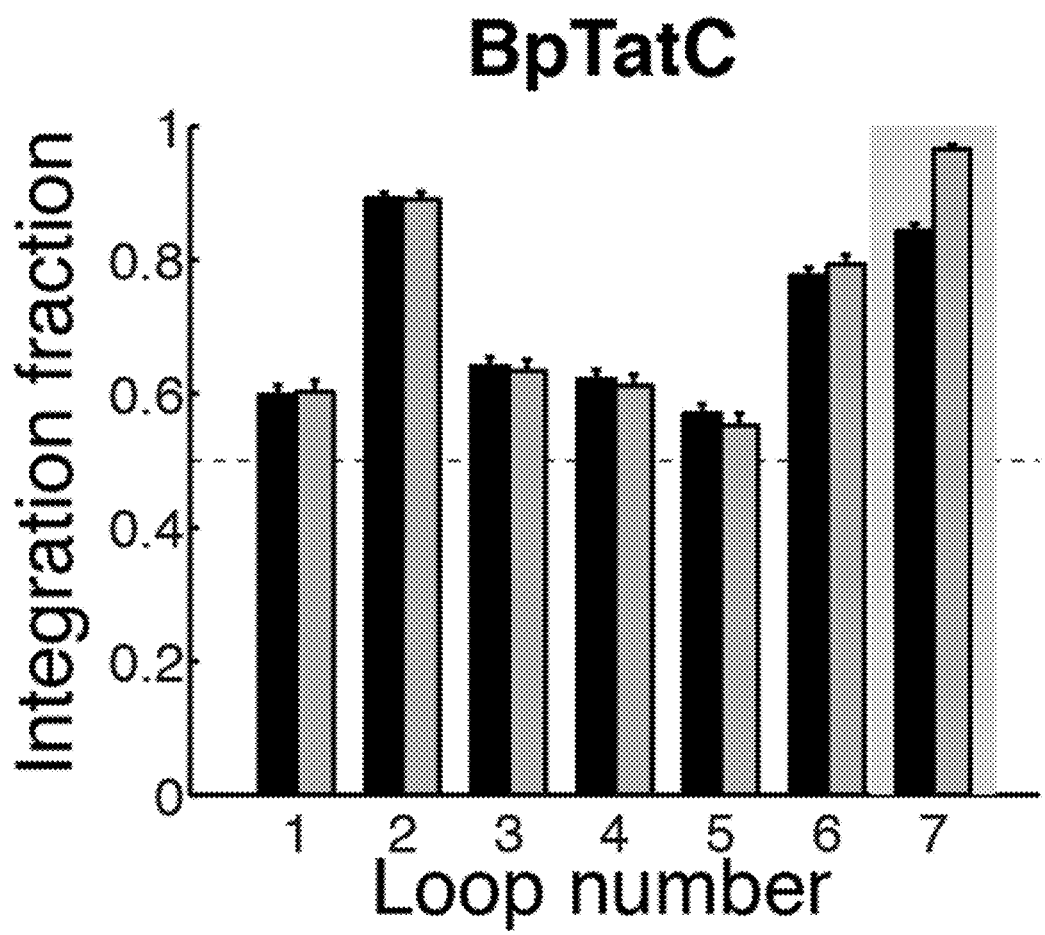
Figure 25F:
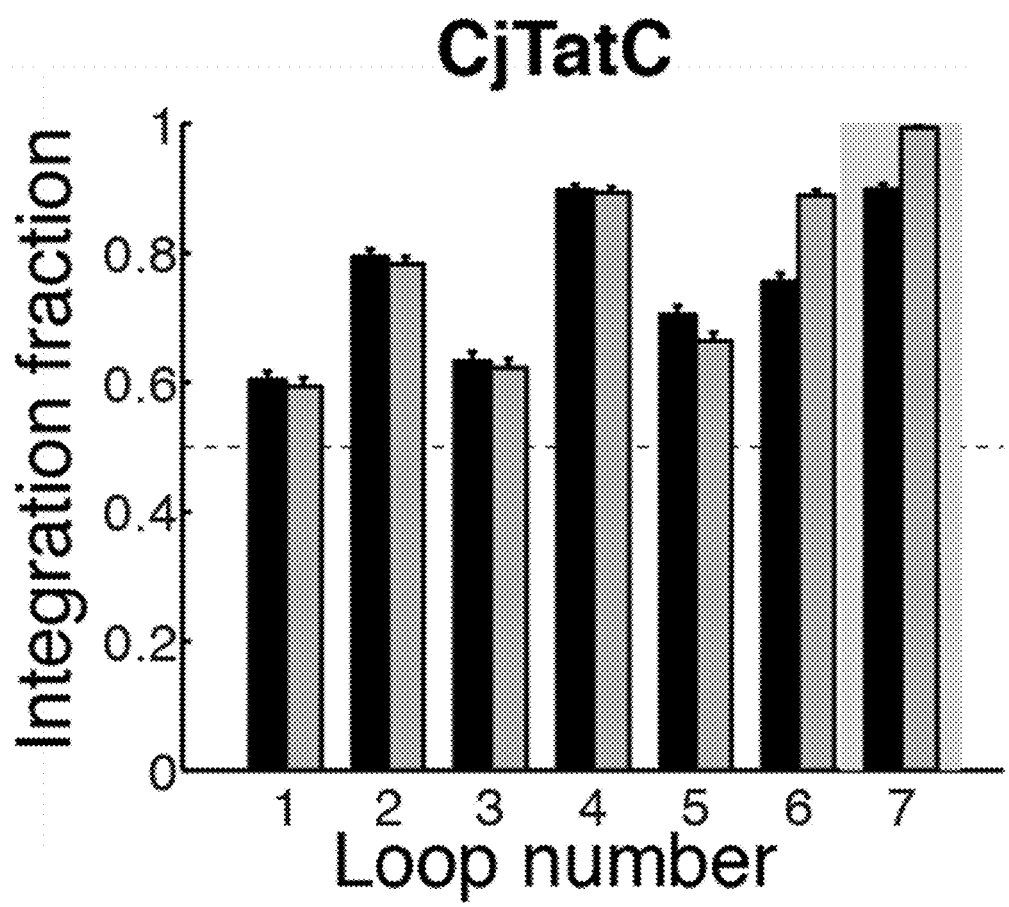
Figure 25G:
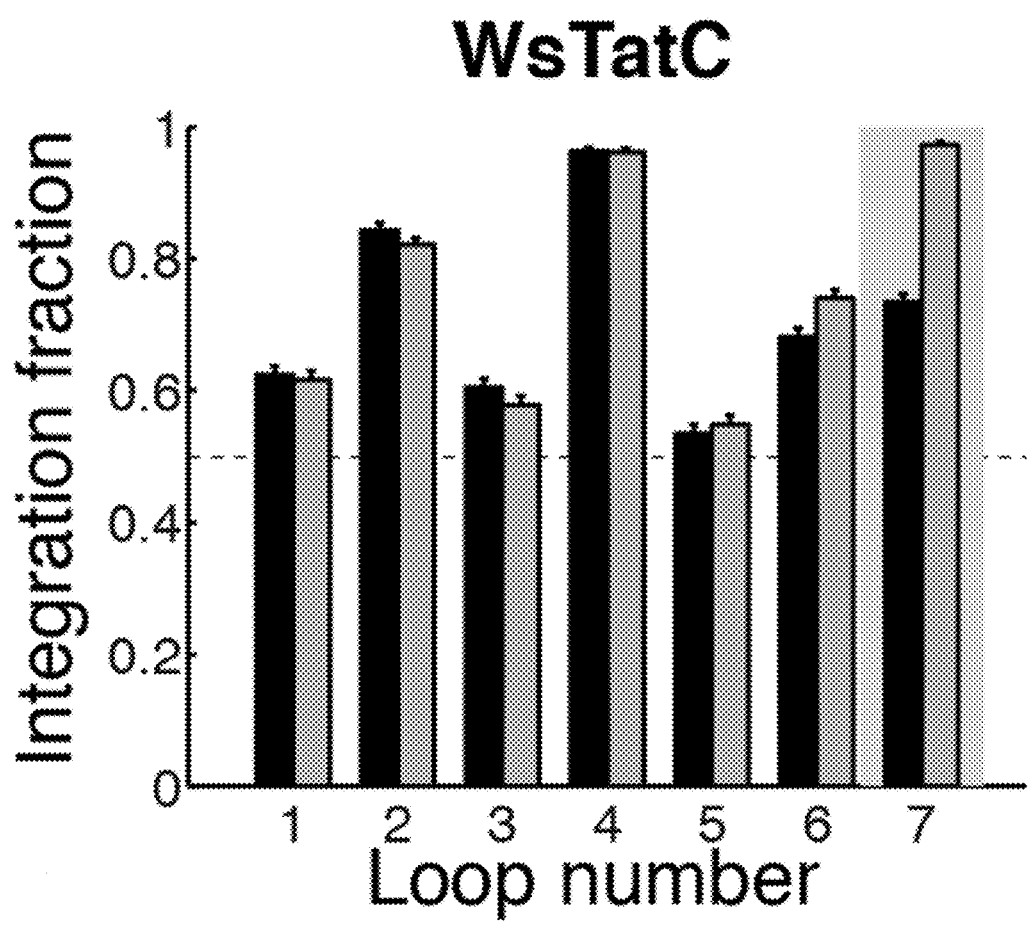
Figure 26:
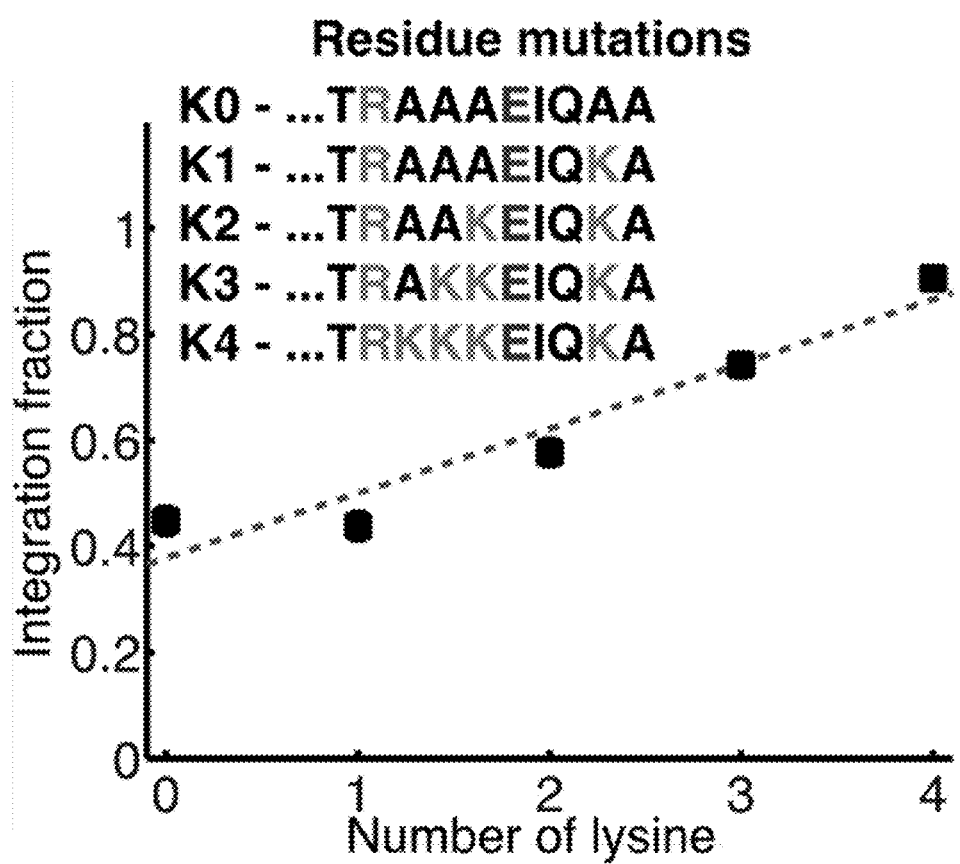
FIG. 26 shows the probability of observing the desired TABF for TatC can be improved by increasing the C-terminal charge. Compared to the result in FIG. 17A here, instead of scaling the charges, the effect of lysine to alanine mutations in the AaTatC C-terminal sequence is investigated; the inset shows the C-terminal loop sequences used, plotted is the integration fraction against the number of lysine residues retained in the C-terminal loop. Sequences with more lysine residues, and thus a higher absolute charge, integrate with higher efficiency.

The results show that simulations of the integration correlate well with the actual expression levels. In addition, the simulations provide an explanation for the experimentally observed expression levels (see, by way of example, the embodiment of FIG. 35) namely that without sufficient positive charge on the C-terminal loop the protein will integrate in an undesired topology as shown in FIG. 25A.

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, Examples and List of References is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the computer readable form of the sequence listing of the ASCII text file P1470-US-Sequences_ST25 being filed concurrently with the present paper is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims

REFERENCES

1. Zhang B, Miller T F, 3rd: Long-timescale dynamics and regulation of Sec-facilitated protein translocation. *Cell Rep.* 2012, 2:927-937.
2. Hessa T, White S H, von Heijne G: Membrane insertion of a potassium-channel voltage sensor. *Science.* 2005, 307:1427.
3. Hessa T, Meindl-Beinker N M, Bernsel A, et al.: Molecular code for transmembrane-helix recognition by the Sec61 translocon. *Nature.* 2007, 450:1026-1030.
4. Hanke F, Serr A, Kreuzer H J, Netz R R: Stretching single polypeptides: The effect of rotational constraints in the backbone. *EPL.* 2010, 92.
5. Staple D B, Payne S H, Reddin A L C, Kreuzer H J: Model for stretching and unfolding the giant multidomain muscle protein using single-molecule force spectroscopy. *Phys Rev Lett.* 2008, 101:248301.
6. Kremer K, Grest G S: Dynamics of entangled linear polymer melts: A molecular-dynamics simulation. *J Chem Phys.* 1990, 92:5057-5086.
7. Weeks J D, Chandler D, Andersen H C: Role of repulsive forces in determining the equilibrium structure of simple liquids. *J Chem Phys.* 1971, 54:5237-5247.
8. Plath K, Mothes W, Wilkinson B M, Stirling C J, Rapoport T A: Signal sequence recognition in posttranslational protein transport across the yeast E R membrane. *Cell.* 1998, 94:795-807.
9. Stoer J, Bulirsch R: *Introduction to numerical analysis*: Springer, 2002.
10. Bilgin N, Claesens F, Pahverk H, Ehrenberg M: Kinetic properties of *Escherichia coli* ribosomes with altered forms of S12. *J Mol Biol.* 1992, 224:1011-1027.
11. Boehlke K W, Friesen J D: Cellular content of ribonucleic acid and protein in *Saccharomyces cerevisiae* as a function of exponential growth rate: calculation of the apparent peptide chain elongation rate. *J Bacteriol.* 1975, 121:429-433.
12. Abou Elela S, Nazar R N: Role of the 5.8S rRNA in ribosome translocation. *Nucleic Acids Res.* 1997, 25:1788-1794.
13. Goder V, Spiess M: Molecular mechanism of signal sequence orientation in the endoplasmic reticulum. *EMBO* 1 2003, 22:3645-3653.
14. Brodsky J L, Goeckeler J, Schekman R: BiP and Sec63p are required for both co- and posttranslational protein translocation into the yeast endoplasmic reticulum. *Proc Natl Acad Sci USA.* 1995, 92:9643-9646.
15. Matlack K E, Misselwitz B, Plath K, Rapoport T A: BiP acts as a molecular ratchet during posttranslational transport of prepro-alpha factor across the E R membrane. *Cell.* 1999, 97:553-564.
16. Buchete N V, Hummer G: Coarse master equations for peptide folding dynamics. *J Phys Chem B.* 2008, 112:6057-6069.
17. Sriraman S, Kevrekidis L G, Hummer G: Coarse master equation from Bayesian analysis of replica molecular dynamics simulations. *Journal of Physical Chemistry B.* 2005, 109:6479-6484.
18. Ramasamy S, Abrol R, Suloway C J, Clemons Jr W M: The glove-like structure of the conserved membrane protein TatC provides insight into signal sequence recognition in twin-arginine translocation. *Structure.* 2013, 21:777-788.

The invention claimed is:

1. A computerized trajectory-based method to represent translocon-associated protein trajectories, comprising:
   i) representing, by a processor, amino acids corresponding to a protein and an associated translocon as a plurality of coarse grain particles;
   ii) representing, by a processor, confinement and driving force effects of an active protein inserter;
   iii) representing, by a processor, interactions between the coarse grain particles;
   iv) calculating, by a processor, evolution of a chain of the coarse grain particles corresponding to the protein in the translocon as a function of time, with a translation rate of at least 6 res/s;
   v) based on steps i)-iv), building, by a processor, translocon-associated protein trajectories; and
   vi) providing, by a processor, spatial representation of the translocon-associated protein trajectories to a user.

2. The method of claim 1, wherein the interactions comprise one or more of bonded, non-bonded, electrostatic, and solvation interactions.

3. The method of claim 1, wherein the active protein inserter is a ribosome or a SecA.

4. The method of claim 1, wherein the protein trajectories comprise protein integration trajectories and protein translocation trajectories.

5. The method of claim 1, wherein each coarse grain particle corresponds to a single atom or multiple atoms of the protein or translocon.

6. The method of claim 1, further comprising:
   calculating, by a processor, stochastic transitions of the coarse grain particles corresponding to the lateral gate helices between an open and closed state for building the trajectories, wherein in the open state of the lateral gate helices the coarse grain particles corresponding to the lateral gate helices do not interact with the coarse grain particles corresponding to the protein, and in the closed state of the lateral gate helices the coarse grain particles corresponding to the lateral gate helices interact with the coarse grain particles corresponding to the protein; and based on the spatial representation of the translocon-associated protein trajectories, providing, by a processor, translocon associated biogenesis features to the user.

7. The method of claim 1, further comprising:
   calculating, by a processor, lumenal biasing factors for building the trajectories.

8. The method of claim 7, wherein the lumenal biasing factors include BiP.

9. The method of claim 1, wherein the coarse grain particles are constrained to a plane bisecting the translocon.

10. The method of claim 9, wherein the plane coincides with a transmembrane axis of the translocon and bisects lateral gate helices.

11. The method of claim 1, wherein the coarse grain particles have an adjustable level of coarseness by having each particle correspond to a controllable amount of amino acids of the protein.

12. The method of claim 6, wherein the translocon associated biogenesis features comprise one or more of: partitioning between protein integration and protein secretion, topology of the protein, and expression level of the protein.

13. The method of claim 12, wherein the partitioning comprises representation, for at least one segment of a trajectory, if the segment was secreted, retained or integrated.

14. The method of claim 12, wherein the topology of the protein represents, for at least one segment of the protein, if the segment has a type II topology, a type III topology or a different type of topology.

15. The method of claim 12, wherein the expression level of the protein represents a percentage of the protein to be expressed according to a desired topology.

16. A non-transitory digital medium comprising instructions that, when executed on a computer, perform the method of claim 1.

17. A computer comprising the non-transitory digital medium of claim 16.

* * * * *

SEQUENCE LISTING

<160> NUMBER OF SEQ ID NOS: 17

<210> SEQ ID NO 1
<211> LENGTH: 284
<212> TYPE: PRT
<213> ORGANISM: Mycobacterium tuberculosis

<400> SEQUENCE: 1

```
Met Ser Leu Val Asp His Leu Thr Glu Leu Arg Thr Arg Leu Leu Ile
1               5                   10                  15

Ser Leu Ala Ala Ile Leu Val Thr Thr Ile Phe Gly Phe Val Trp Tyr
            20                  25                  30

Ser His Ser Ile Phe Gly Leu Asp Ser Leu Gly Glu Trp Leu Arg His
        35                  40                  45

Pro Tyr Cys Ala Leu Pro Gln Ser Ala Arg Ala Asp Ile Ser Ala Asp
    50                  55                  60

Gly Glu Cys Arg Leu Leu Ala Thr Ala Pro Phe Asp Gln Phe Met Leu
65                  70                  75                  80

Arg Leu Lys Val Gly Met Ala Ala Gly Ile Val Leu Ala Cys Pro Val
                85                  90                  95

Trp Phe Tyr Gln Leu Trp Ala Phe Ile Thr Pro Gly Leu Tyr Gln Arg
            100                 105                 110

Glu Arg Arg Phe Ala Val Ala Phe Val Ile Pro Ala Val Leu Phe
        115                 120                 125

Val Ala Gly Ala Val Leu Ala Tyr Leu Val Leu Ser Lys Ala Leu Gly
    130                 135                 140

Phe Leu Leu Thr Val Gly Ser Asp Val Gln Val Thr Ala Leu Ser Gly
145                 150                 155                 160

Asp Arg Tyr Phe Gly Phe Leu Leu Asn Leu Leu Val Val Phe Gly Val
                165                 170                 175

Ser Phe Glu Phe Pro Leu Leu Ile Val Met Leu Asn Leu Ala Gly Leu
            180                 185                 190

Leu Thr Tyr Glu Arg Leu Lys Ser Trp Arg Arg Gly Leu Ile Phe Ala
        195                 200                 205

Met Phe Val Phe Ala Ala Ile Phe Thr Pro Gly Ser Asp Pro Phe Ser
    210                 215                 220

Met Thr Ala Leu Gly Ala Ala Leu Thr Val Leu Leu Glu Leu Ala Ile
225                 230                 235                 240

Gln Ile Ala Arg Val His Asp Lys Arg Lys Ala Lys Arg Glu Ala Ala
                245                 250                 255

Ile Pro Asp Asp Glu Ala Ser Val Ile Asp Pro Pro Ser Pro Val Pro
            260                 265                 270

Ala Pro Ser Val Ile Gly Ser His Asp Asp Val Thr
        275                 280
```

<210> SEQ ID NO 2
<211> LENGTH: 240
<212> TYPE: PRT
<213> ORGANISM: Aquifex aeolicus

<400> SEQUENCE: 2

```
Met Pro Leu Thr Glu His Leu Arg Glu Leu Arg Tyr Arg Leu Ile Ile
1               5                   10                  15

Ser Ile Ile Ala Phe Leu Ile Gly Ser Gly Ile Ala Phe Tyr Phe Ala
            20                  25                  30

Lys Tyr Val Phe Glu Ile Leu Lys Glu Pro Ile Leu Lys Ser Tyr Pro
```

```
                35                  40                  45
Glu Val Glu Leu Ile Thr Leu Ser Pro Thr Glu Pro Leu Phe Ile Leu
 50                  55                  60

Ile Lys Ile Ser Leu Ala Val Gly Phe Ile Ile Ala Ser Pro Val Ile
 65                  70                  75                  80

Leu Tyr Gln Phe Trp Arg Phe Ile Glu Pro Ala Leu Tyr Ser His Glu
                 85                  90                  95

Lys Arg Ala Phe Ile Pro Leu Leu Gly Ser Ile Leu Leu Phe Met
                100                 105                 110

Leu Gly Ala Leu Phe Ala Tyr Phe Ile Val Leu Pro Leu Ala Leu Lys
                115                 120                 125

Phe Leu Leu Gly Leu Gly Phe Thr Gln Leu Leu Ala Thr Pro Tyr Leu
130                 135                 140

Ser Val Asp Met Tyr Ile Ser Phe Val Leu Lys Leu Val Val Ala Phe
145                 150                 155                 160

Gly Ile Ala Phe Glu Met Pro Ile Val Leu Tyr Val Leu Gln Lys Ala
                165                 170                 175

Gly Val Ile Thr Pro Glu Gln Leu Ala Ser Phe Arg Lys Tyr Phe Ile
                180                 185                 190

Val Ile Ala Phe Val Ile Gly Ala Ile Ile Ala Pro Asp Val Ser Thr
                195                 200                 205

Gln Val Leu Met Ala Ile Pro Leu Leu Leu Tyr Glu Ile Ser Ile
210                 215                 220

Phe Leu Gly Lys Leu Ala Thr Arg Lys Lys Lys Glu Ile Gln Lys Ala
225                 230                 235                 240

<210> SEQ ID NO 3
<211> LENGTH: 240
<212> TYPE: PRT
<213> ORGANISM: Aquifex aeolicus

<400> SEQUENCE: 3

Met Pro Leu Thr Glu His Leu Arg Glu Leu Arg Tyr Arg Leu Ile Ile
 1               5                  10                  15

Ser Ile Ile Ala Phe Leu Ile Gly Ser Gly Ile Ala Phe Tyr Phe Ala
                 20                  25                  30

Lys Tyr Val Phe Glu Ile Leu Lys Glu Pro Ile Leu Lys Ser Tyr Pro
                 35                  40                  45

Glu Val Glu Leu Ile Thr Leu Ser Pro Thr Glu Pro Leu Phe Ile Leu
 50                  55                  60

Ile Lys Ile Ser Leu Ala Val Gly Phe Ile Ile Ala Ser Pro Val Ile
 65                  70                  75                  80

Leu Tyr Gln Phe Trp Arg Phe Ile Glu Pro Ala Leu Tyr Ser His Glu
                 85                  90                  95

Lys Arg Ala Phe Ile Pro Leu Leu Gly Ser Ile Leu Leu Phe Met
                100                 105                 110

Leu Gly Ala Leu Phe Ala Tyr Phe Ile Val Leu Pro Leu Ala Leu Lys
                115                 120                 125

Phe Leu Leu Gly Leu Gly Phe Thr Gln Leu Leu Ala Thr Pro Tyr Leu
130                 135                 140

Ser Val Asp Met Tyr Ile Ser Phe Val Leu Lys Leu Val Val Ala Phe
145                 150                 155                 160

Gly Ile Ala Phe Glu Met Pro Ile Val Leu Tyr Val Leu Gln Lys Ala
                165                 170                 175
```

```
Gly Val Ile Thr Pro Glu Gln Leu Ala Ser Phe Arg Lys Tyr Phe Ile
            180                 185                 190

Val Ile Ala Phe Val Ile Gly Ala Ile Ile Ala Pro Asp Val Ser Thr
        195                 200                 205

Gln Val Leu Met Ala Ile Pro Leu Leu Leu Leu Tyr Glu Ile Ser Ile
    210                 215                 220

Phe Leu Gly Lys Leu Ala Thr Arg Lys Lys Lys Glu Ile Gln Lys Ala
225                 230                 235                 240

<210> SEQ ID NO 4
<211> LENGTH: 266
<212> TYPE: PRT
<213> ORGANISM: Bordetella parapertussis

<400> SEQUENCE: 4

Met Ser Gln Asp Ala Ser Asn Asp Asn Pro Asp Gln Gln Gln Asp Ser
1               5                   10                  15

Phe Ile Ser His Leu Val Glu Leu Arg Ser Arg Leu Leu Lys Ala Ala
            20                  25                  30

Gly Ala Val Val Ala Val Phe Ile Val Leu Phe Leu Tyr Pro Gly Ala
        35                  40                  45

Ser Ala Ile Tyr Asp Val Leu Ala Gln Pro Met Leu Ala Ser Leu Pro
    50                  55                  60

Glu Gly Thr Arg Met Ile Ala Thr Gly Val Ile Thr Pro Phe Met Val
65                  70                  75                  80

Pro Val Lys Val Thr Met Met Ala Ala Phe Val Val Ala Leu Pro Val
                85                  90                  95

Val Leu Tyr Gln Ala Trp Ala Phe Val Ala Pro Gly Leu Tyr Lys His
            100                 105                 110

Glu Lys Arg Leu Ala Leu Pro Leu Ile Leu Ser Ser Thr Leu Leu Phe
        115                 120                 125

Ile Ile Gly Met Ala Phe Cys Tyr Phe Phe Val Phe Arg Thr Val Phe
    130                 135                 140

His Phe Ile Ala Thr Phe Ala Pro Gln Ser Ile Thr Pro Ala Pro Asp
145                 150                 155                 160

Ile Glu Ala Tyr Leu Ser Phe Val Met Thr Met Phe Met Ala Phe Gly
                165                 170                 175

Ile Thr Phe Glu Val Pro Val Ala Val Val Leu Leu Val Lys Thr Gly
            180                 185                 190

Ile Val Glu Val Ala Lys Leu Arg Ala Ala Arg Gly Tyr Val Val Val
        195                 200                 205

Gly Ala Phe Val Ile Ala Ala Val Val Thr Pro Pro Asp Val Val Ser
    210                 215                 220

Gln Phe Met Leu Ala Val Pro Leu Cys Leu Leu Tyr Glu Val Gly Leu
225                 230                 235                 240

Leu Cys Ala Arg Leu Val Thr Pro Arg Arg Arg Gly Glu Glu Glu Ser
                245                 250                 255

Glu Asp Asp Gln Ala Leu Thr Glu Arg His
            260                 265

<210> SEQ ID NO 5
<211> LENGTH: 245
<212> TYPE: PRT
<213> ORGANISM: Campylobacter jejuni

<400> SEQUENCE: 5
```

```
Met Phe Glu Glu Leu Arg Pro His Leu Ile Glu Leu Arg Lys Arg Leu
1               5                   10                  15

Phe Ile Ser Val Ala Cys Ile Val Val Met Phe Ile Val Cys Phe Ala
            20                  25                  30

Leu Arg Ser Tyr Ile Leu Asp Ile Leu Lys Ala Pro Leu Ile Ala Val
        35                  40                  45

Leu Pro Glu Val Ala Lys His Val Asn Val Ile Glu Val Gln Glu Ala
    50                  55                  60

Leu Phe Thr Ala Met Lys Val Ser Phe Phe Ala Ala Phe Ile Phe Ser
65              70                  75                  80

Leu Pro Val Ile Phe Trp Gln Phe Trp Lys Phe Val Ala Pro Gly Leu
                85                  90                  95

Tyr Asp Asn Glu Lys Arg Leu Val Val Pro Phe Val Ser Phe Ala Ser
            100                 105                 110

Ile Met Phe Ala Phe Gly Ala Cys Phe Cys Tyr Phe Val Val Val Pro
        115                 120                 125

Leu Ala Phe Lys Phe Leu Ile Asn Phe Gly Leu Asn Glu Asp Phe Asn
    130                 135                 140

Pro Val Ile Thr Ile Gly Thr Tyr Val Asp Phe Phe Thr Lys Val Val
145                 150                 155                 160

Val Ala Phe Gly Leu Ala Phe Glu Met Pro Val Ile Ala Phe Phe Phe
                165                 170                 175

Ala Lys Ile Gly Leu Ile Asp Asp Ser Phe Leu Lys Arg His Phe Arg
            180                 185                 190

Ile Ala Val Leu Val Ile Phe Val Phe Ser Ala Phe Met Thr Pro Pro
        195                 200                 205

Asp Val Leu Ser Gln Phe Leu Met Ala Gly Pro Leu Cys Gly Leu Tyr
    210                 215                 220

Gly Leu Ser Ile Leu Ile Val Gln Lys Val Asn Pro Ala Pro Lys Asp
225                 230                 235                 240

Lys Glu Ser Asp Glu
            245

<210> SEQ ID NO 6
<211> LENGTH: 270
<212> TYPE: PRT
<213> ORGANISM: Deinococcus radiodurans

<400> SEQUENCE: 6

Met Thr Gln Leu Pro Pro Pro Glu Gln Thr Val Leu Lys Pro Ala Pro
1               5                   10                  15

Pro Glu Leu Ala Ser Ala Pro Leu Phe Asp His Leu Glu Glu Leu Arg
            20                  25                  30

Arg Arg Leu Ile Leu Ser Val Val Phe Leu Ala Val Gly Met Val Ile
        35                  40                  45

Ala Phe Thr Tyr Arg Val Gln Leu Ile Glu Leu Val Lys Val Pro Leu
    50                  55                  60

Thr Tyr Ser Glu Leu Tyr Thr Thr Gly Lys Val Gln Leu Val Thr Thr
65              70                  75                  80

Lys Leu Ala Ser Gln Leu Leu Ser Phe Asn Leu Ala Phe Trp Ala
                85                  90                  95

Gly Leu Thr Leu Ala Leu Pro Phe Ile Val Trp Gln Ile Trp Ala Phe
            100                 105                 110

Ile Ala Pro Gly Leu Tyr Pro Gln Glu Arg Arg Trp Gly Leu Pro Phe
        115                 120                 125
```

```
Ile Leu Gly Ala Gly Phe Ala Phe Ala Ala Gly Val Val Phe Gly Tyr
        130                 135                 140

Lys Leu Val Leu Pro Thr Met Val Pro Phe Leu Ile Glu Phe Leu Ala
145                 150                 155                 160

Gly Thr Val Thr Gln Met Gln Asp Leu Gln Glu Tyr Ile Gly Thr Val
                165                 170                 175

Val Thr Phe Leu Val Ala Phe Gly Val Ala Phe Glu Leu Pro Ile Leu
                180                 185                 190

Ala Val Ile Leu Thr Arg Leu Gly Ile Val Asn His Thr Met Leu Arg
            195                 200                 205

Gln Gly Trp Arg Phe Ala Leu Ile Gly Ile Met Ile Leu Ala Ala Val
        210                 215                 220

Ile Thr Pro Thr Pro Asp Pro Ala Asn Met Ala Leu Val Ala Val Pro
225                 230                 235                 240

Leu Tyr Ala Leu Tyr Glu Leu Gly Val Val Leu Ser Arg Val Phe Arg
                245                 250                 255

Val Ile Ala Pro Glu Glu Gln Glu Arg Pro Ala Pro Met Ser
                260                 265                 270

<210> SEQ ID NO 7
<211> LENGTH: 258
<212> TYPE: PRT
<213> ORGANISM: Escherichia coli

<400> SEQUENCE: 7

Met Ser Val Glu Asp Thr Gln Pro Leu Ile Thr His Leu Ile Glu Leu
1               5                   10                  15

Arg Lys Arg Leu Leu Asn Cys Ile Ile Ala Val Ile Val Ile Phe Leu
            20                  25                  30

Cys Leu Val Tyr Phe Ala Asn Asp Ile Tyr His Leu Val Ser Ala Pro
        35                  40                  45

Leu Ile Lys Gln Leu Pro Gln Gly Ser Thr Met Ile Ala Thr Asp Val
    50                  55                  60

Ala Ser Pro Phe Phe Thr Pro Ile Lys Leu Thr Phe Met Val Ser Leu
65                  70                  75                  80

Ile Leu Ser Ala Pro Val Ile Leu Tyr Gln Val Trp Ala Phe Ile Ala
                85                  90                  95

Pro Ala Leu Tyr Lys His Glu Arg Arg Leu Val Val Pro Leu Leu Val
            100                 105                 110

Ser Ser Ser Leu Leu Phe Tyr Ile Gly Met Ala Phe Ala Tyr Phe Val
        115                 120                 125

Val Phe Pro Leu Ala Phe Gly Phe Leu Ala Asn Thr Ala Pro Glu Gly
    130                 135                 140

Val Gln Val Ser Thr Asp Ile Ala Ser Tyr Leu Ser Phe Val Met Ala
145                 150                 155                 160

Leu Phe Met Ala Phe Gly Val Ser Phe Glu Val Pro Val Ala Ile Val
                165                 170                 175

Leu Leu Cys Trp Met Gly Ile Thr Ser Pro Glu Asp Leu Arg Lys Lys
            180                 185                 190

Arg Pro Tyr Val Leu Val Gly Ala Phe Val Val Gly Met Leu Leu Thr
        195                 200                 205

Pro Pro Asp Val Phe Ser Gln Thr Leu Leu Ala Ile Pro Met Tyr Cys
    210                 215                 220

Leu Phe Glu Ile Gly Val Phe Phe Ser Arg Phe Tyr Val Gly Lys Gly
```

```
                225                 230                 235                 240
Arg Asn Arg Glu Glu Asn Asp Ala Glu Ala Glu Ser Glu Lys Thr
                    245                 250                 255
Glu Glu

<210> SEQ ID NO 8
<211> LENGTH: 233
<212> TYPE: PRT
<213> ORGANISM: Staphylococcus aureus

<400> SEQUENCE: 8

Met Val His Phe Ser Glu Leu Arg His Arg Leu Val Lys Ile Leu Leu
1               5                   10                  15

Ser Phe Val Ile Thr Val Ile Val Tyr Val Ser Ser Phe Trp Trp
                20                  25                  30

Met Thr Pro Phe Ile Thr Tyr Ile Thr Arg Ala His Val Ser Leu His
                35                  40                  45

Ala Phe Ser Phe Thr Glu Met Ile Gln Ile Tyr Val Met Ile Ile Phe
        50                  55                  60

Phe Ile Ala Phe Cys Leu Ile Ser Pro Val Met Phe Tyr Gln Leu Trp
65                  70                  75                  80

Ala Phe Val Ala Pro Gly Leu His Asn Asn Glu Arg Gln Phe Ile Tyr
                85                  90                  95

Lys Tyr Ser Phe Phe Ser Val Leu Leu Phe Ile Phe Gly Val Ala Phe
                100                 105                 110

Ala Phe Tyr Val Gly Phe Pro Met Ile Ile Gln Phe Ala Leu Lys Leu
                115                 120                 125

Ser Leu Thr Leu Asn Ile Ser Pro Val Ile Gly Phe Lys Ala Tyr Leu
        130                 135                 140

Ile Glu Leu Ile Arg Trp Leu Phe Thr Phe Gly Ile Leu Phe Gln Leu
145                 150                 155                 160

Pro Ile Leu Phe Ile Gly Leu Ala Lys Phe Gly Leu Ile Asp Thr Thr
                165                 170                 175

Ser Leu Lys His Tyr Arg Lys Tyr Ile Tyr Phe Ala Cys Phe Val Leu
                180                 185                 190

Ala Ser Ile Ile Ala Pro Pro Asp Leu Thr Leu Asn Ile Leu Leu Thr
                195                 200                 205

Leu Pro Leu Ile Leu Leu Phe Glu Phe Ser Thr Phe Ile Val Lys Phe
        210                 215                 220

Thr Tyr Arg Gly Lys Pro Pro Thr His
225                 230

<210> SEQ ID NO 9
<211> LENGTH: 250
<212> TYPE: PRT
<213> ORGANISM: Vibrio cholerae

<400> SEQUENCE: 9

Met Ser Ser Val Glu Gln Thr Gln Pro Leu Ile Ser His Leu Leu Glu
1               5                   10                  15

Leu Arg Asn Arg Leu Leu Lys Ala Val Ala Val Ile Val Val Phe
                20                  25                  30

Ile Gly Leu Ile Tyr Phe Ser Asn Glu Ile Tyr Glu Phe Val Ser Lys
        35                  40                  45

Pro Leu Val Asp Arg Leu Pro Ala Gly Ala Thr Met Ile Ala Thr Asp
        50                  55                  60
```

```
Val Ala Ser Pro Phe Phe Thr Pro Leu Lys Leu Thr Leu Ile Ala Ala
 65                  70                  75                  80

Val Phe Leu Ala Val Pro Phe Ile Leu Tyr Gln Val Trp Ala Phe Val
                 85                  90                  95

Ala Pro Gly Leu Tyr Lys His Glu Arg Arg Leu Ile Phe Pro Leu Leu
            100                 105                 110

Val Ser Ser Leu Leu Phe Tyr Cys Gly Val Ala Phe Ala Tyr Phe
        115                 120                 125

Val Val Phe Pro Leu Val Phe Gly Phe Thr Ala Ile Ser Leu Gly
130                 135                 140

Gly Val Glu Phe Ala Thr Asp Ile Ala Ser Tyr Leu Asp Phe Val Leu
145                 150                 155                 160

Ala Leu Phe Leu Ala Phe Gly Ile Ala Phe Glu Val Pro Val Ala Ile
                165                 170                 175

Ile Leu Leu Cys Trp Thr Gly Ala Thr Thr Pro Lys Ser Leu Ser Glu
            180                 185                 190

Lys Arg Pro Tyr Ile Ile Val Gly Ala Phe Val Gly Met Leu Leu
        195                 200                 205

Thr Pro Pro Asp Met Ile Ser Gln Thr Leu Leu Ala Ile Pro Met Cys
210                 215                 220

Leu Leu Phe Glu Val Gly Leu Phe Phe Ala Arg Phe Tyr Thr Arg Asp
225                 230                 235                 240

Glu Ala Glu Glu Ala Ala Glu Glu Asp Glu
                245                 250

<210> SEQ ID NO 10
<211> LENGTH: 241
<212> TYPE: PRT
<213> ORGANISM: Wolinella succinogenes

<400> SEQUENCE: 10

Met Phe Glu Glu Leu Lys Pro His Ile Gln Leu Arg Lys Arg Leu
1               5                   10                  15

Ile Asn Ala Val Val Ala Leu Phe Ile Ala Phe Phe Ile Cys Phe Phe
                20                  25                  30

Phe Trp Glu Gly Ile Leu Asp Trp Met Ile Ala Pro Leu Lys Ala Ala
            35                  40                  45

Leu Pro Ala Gly Ser Asn Val Ile Phe Thr Glu Val Gly Glu Ala Phe
        50                  55                  60

Phe Thr Ala Ile Lys Val Ser Phe Ser Ala Phe Met Phe Ser Leu
65                  70                  75                  80

Pro Val Ile Phe Trp Gln Val Trp Leu Phe Val Ala Pro Gly Leu Tyr
                85                  90                  95

Gln Asn Glu Lys Met Leu Val Leu Pro Phe Val Phe Gly Thr Leu
            100                 105                 110

Met Phe Val Thr Gly Ala Leu Phe Ala Tyr Tyr Val Val Phe Pro Phe
        115                 120                 125

Gly Phe Thr Tyr Leu Ile Asn Phe Gly Ser Thr Leu Phe Thr Ala Leu
130                 135                 140

Pro Ser Val Gly Phe Tyr Val Thr Phe Ala Lys Leu Met Ile Gly
145                 150                 155                 160

Phe Gly Ile Ala Phe Glu Leu Pro Val Val Thr Phe Phe Leu Ala Lys
                165                 170                 175

Leu Gly Leu Val Thr Asp Lys Thr Leu Arg Asp Phe Phe Lys Tyr Ala
```

```
            180                 185                 190
Ile Ile Ile Ile Phe Ile Val Ala Ala Ile Leu Thr Pro Pro Asp Val
            195                 200                 205
Ile Thr Gln Phe Met Met Ala Ile Pro Leu Thr Phe Leu Tyr Trp Val
            210                 215                 220
Ser Ile Leu Ile Ala Lys Met Val Asn Pro Glu Thr Ser Pro Asn Glu
225                 230                 235                 240
Glu

<210> SEQ ID NO 11
<211> LENGTH: 307
<212> TYPE: PRT
<213> ORGANISM: Mycobacterium tuberculosis

<400> SEQUENCE: 11

Arg Ala Ala Gly Leu Leu Lys Arg Leu Asn Pro Arg Asn Arg Arg Ser
1               5                   10                  15
Arg Val Asn Pro Asp Ala Thr Met Ser Leu Val Asp His Leu Thr Glu
            20                  25                  30
Leu Arg Thr Arg Leu Leu Ile Ser Leu Ala Ala Ile Leu Val Thr Thr
        35                  40                  45
Ile Phe Gly Phe Val Trp Tyr Ser His Ser Ile Phe Gly Leu Asp Ser
50                  55                  60
Leu Gly Glu Trp Leu Arg His Pro Tyr Cys Ala Leu Pro Gln Ser Ala
65                  70                  75                  80
Arg Ala Asp Ile Ser Ala Asp Gly Glu Cys Arg Leu Leu Ala Thr Ala
                85                  90                  95
Pro Phe Asp Gln Phe Met Leu Arg Leu Lys Val Gly Met Ala Ala Gly
            100                 105                 110
Ile Val Leu Ala Cys Pro Val Trp Phe Tyr Gln Leu Trp Ala Phe Ile
        115                 120                 125
Thr Pro Gly Leu Tyr Gln Arg Glu Arg Arg Phe Ala Val Ala Phe Val
    130                 135                 140
Ile Pro Ala Ala Val Leu Phe Val Ala Gly Ala Val Leu Ala Tyr Leu
145                 150                 155                 160
Val Leu Ser Lys Ala Leu Gly Phe Leu Leu Thr Val Gly Ser Asp Val
                165                 170                 175
Gln Val Thr Ala Leu Ser Gly Asp Arg Tyr Phe Gly Phe Leu Leu Asn
            180                 185                 190
Leu Leu Val Val Phe Gly Val Ser Phe Glu Pro Leu Leu Ile Val
        195                 200                 205
Met Leu Asn Leu Ala Gly Leu Leu Thr Tyr Glu Arg Leu Lys Ser Trp
    210                 215                 220
Arg Arg Gly Leu Ile Phe Ala Met Phe Val Phe Ala Ala Ile Phe Thr
225                 230                 235                 240
Pro Gly Ser Asp Pro Phe Ser Met Thr Ala Leu Gly Ala Ala Leu Thr
                245                 250                 255
Val Leu Leu Glu Leu Ala Ile Gln Ile Ala Arg Val His Asp Lys Arg
            260                 265                 270
Lys Ala Lys Arg Glu Ala Ala Ile Pro Asp Asp Glu Ala Ser Val Ile
        275                 280                 285
Asp Pro Pro Ser Pro Val Pro Ala Pro Ser Val Ile Gly Ser His Asp
    290                 295                 300
Asp Val Thr
```

```
<210> SEQ ID NO 12
<211> LENGTH: 43
<212> TYPE: DNA
<213> ORGANISM: Artificial sequence
<220> FEATURE:
<223> OTHER INFORMATION: Synthetic Polynucleotide

<400> SEQUENCE: 12
ggtgaaaacc tgtacttcca gagcatgcca ctgaccgaac acc           43

<210> SEQ ID NO 13
<211> LENGTH: 50
<212> TYPE: DNA
<213> ORGANISM: Artificial sequence
<220> FEATURE:
<223> OTHER INFORMATION: Synthetic Polynucleotide

<400> SEQUENCE: 13
tggtccctga acaagactt ccaaagcctt ctgaatctcc ttcttttgc       50

<210> SEQ ID NO 14
<211> LENGTH: 44
<212> TYPE: DNA
<213> ORGANISM: Artificial sequence
<220> FEATURE:
<223> OTHER INFORMATION: Synthetic Polynucleotide

<400> SEQUENCE: 14
ggtgaaaacc tgtacttcca gagctctctc gtagaccacc tcac          44

<210> SEQ ID NO 15
<211> LENGTH: 42
<212> TYPE: DNA
<213> ORGANISM: Artificial sequence
<220> FEATURE:
<223> OTHER INFORMATION: Synthetic Polynucleotide

<400> SEQUENCE: 15
tggtccctga acaagactt ccaagtgaac acgcgcgatc tg             42

<210> SEQ ID NO 16
<211> LENGTH: 24
<212> TYPE: DNA
<213> ORGANISM: Artificial sequence
<220> FEATURE:
<223> OTHER INFORMATION: Synthetic Polynucleotide

<400> SEQUENCE: 16
ttggaagtct tgtttcaggg acca                                24

<210> SEQ ID NO 17
<211> LENGTH: 24
<212> TYPE: DNA
<213> ORGANISM: Artificial sequence
<220> FEATURE:
<223> OTHER INFORMATION: Synthetic Polynucleotide

<400> SEQUENCE: 17
gctctggaag tacaggtttt cacc                                24
```